(12) United States Patent
Ammann et al.

(10) Patent No.: US 8,409,209 B2
(45) Date of Patent: Apr. 2, 2013

(54) METHOD AND APPARATUS FOR PERFORMING AN OPEN WEDGE, HIGH TIBIAL OSTEOTOMY

(75) Inventors: Kelly Ammann, Boulder, CO (US); Vincent P. Novak, Longmont, CO (US); Robert Schneider, Erie, CO (US)

(73) Assignee: Arthrex, Inc., Naples, FL (US)

( * ) Notice: Subject to any disclaimer, the term of this patent is extended or adjusted under 35 U.S.C. 154(b) by 404 days.

(21) Appl. No.: 11/986,444

(22) Filed: Nov. 21, 2007

(65) Prior Publication Data
US 2008/0208199 A1    Aug. 28, 2008

Related U.S. Application Data

(60) Provisional application No. 60/860,595, filed on Nov. 22, 2006.

(51) Int. Cl.
*A61F 2/28* (2006.01)
(52) U.S. Cl. .................................................. 606/88
(58) Field of Classification Search ............ 606/60, 606/86 R, 87, 88, 105; 623/16.11, 17.11, 623/20.14, 20.32, 20.34, 20.35, 20.36
See application file for complete search history.

(56) References Cited

U.S. PATENT DOCUMENTS

| | | |
|---|---|---|
| 2,737,724 A | 3/1956 | Herz |
| 3,579,777 A | 5/1971 | Milewski |
| 3,750,652 A | 8/1973 | Sherwin |
| 4,349,018 A | 9/1982 | Chambers |
| 4,421,112 A | 12/1983 | Mains et al. |
| 4,501,268 A | 2/1985 | Comparetto |
| 4,523,587 A | 6/1985 | Frey |
| 4,563,489 A | 1/1986 | Urist |
| 4,565,191 A | 1/1986 | Slocum |
| 4,750,481 A | 6/1988 | Reese |
| 4,769,040 A | 9/1988 | Wevers |
| 4,817,794 A | 4/1989 | Workman |
| 4,851,005 A | 7/1989 | Hunt et al. |
| 4,852,558 A | 8/1989 | Outerbridge |
| 4,892,093 A | 1/1990 | Zarnowski et al. |
| 4,936,844 A | 6/1990 | Chandler et al. |
| 4,961,740 A | 10/1990 | Ray et al. |
| 5,053,039 A | 10/1991 | Hofmann et al. |
| 5,254,119 A | 10/1993 | Schreiber |
| 5,275,603 A | 1/1994 | Ferrante et al. |
| 5,297,538 A | 3/1994 | Daniel |
| 5,306,276 A | 4/1994 | Johnson et al. |

(Continued)

FOREIGN PATENT DOCUMENTS

| | | |
|---|---|---|
| CN | 1132067 | 10/1996 |
| CN | 1181696 | 5/1998 |

(Continued)

OTHER PUBLICATIONS

Oliver C. Kessler et al., Avoidance of Medial Cortical Fracture in High Tibial Osteotomy: Improved Technique, Clinical Orthopaedics and Related Research, Feb. 2002, pp. 180-185, No. 395.

(Continued)

*Primary Examiner* — Eduardo C Robert
*Assistant Examiner* — David Comstock
(74) *Attorney, Agent, or Firm* — Dickstein Shapiro LLP

(57) ABSTRACT

An osteotomy implant for disposition in a wedge-shaped osteotomy opening in a bone, the implant comprising a body for disposition within the wedge-shaped osteotomy opening in the bone and supporting the bone while healing occurs; at least one key formed integral with the body for stabilizing the body relative to the adjacent bone while healing occurs; and at least one fenestration extending through the body for permitting bone growth through the implant.

23 Claims, 64 Drawing Sheets

U.S. PATENT DOCUMENTS

| | | | |
|---|---|---|---|
| 5,352,229 A | 10/1994 | Goble et al. | |
| 5,413,579 A | 5/1995 | Du Toit | |
| 5,445,640 A | 8/1995 | Johnson et al. | |
| 5,451,228 A | 9/1995 | Johnson et al. | |
| 5,540,695 A | 7/1996 | Levy | |
| 5,569,250 A | 10/1996 | Sarver et al. | |
| 5,601,565 A | 2/1997 | Huebner | |
| 5,609,635 A | 3/1997 | Michelson | |
| 5,613,969 A | 3/1997 | Jenkins, Jr. | |
| 5,620,448 A | 4/1997 | Puddu | |
| 5,640,813 A | 6/1997 | Glazik et al. | |
| 5,662,655 A | 9/1997 | Laboureau et al. | |
| 5,669,909 A | 9/1997 | Zdeblick et al. | |
| 5,674,296 A | 10/1997 | Bryan et al. | |
| 5,681,316 A | 10/1997 | DeOrio et al. | |
| 5,722,978 A | 3/1998 | Jenkins, Jr. | |
| 5,733,290 A | 3/1998 | McCue et al. | |
| 5,749,875 A | 5/1998 | Puddu | |
| 5,766,251 A | 6/1998 | Koshino | |
| 5,843,085 A | 12/1998 | Graser | |
| 5,888,223 A | 3/1999 | Bray, Jr. | |
| 5,911,724 A | 6/1999 | Wehrli | |
| 5,980,526 A | 11/1999 | Johnson et al. | |
| 6,008,433 A | 12/1999 | Stone | |
| 6,027,504 A | 2/2000 | McGuire | |
| 6,039,761 A | 3/2000 | Li et al. | |
| 6,086,593 A | 7/2000 | Bonutti | |
| 6,099,531 A | 8/2000 | Bonutti | |
| 6,102,950 A | 8/2000 | Vaccaro | |
| 6,190,390 B1 | 2/2001 | McAllister | |
| 6,200,347 B1 | 3/2001 | Anderson et al. | |
| 6,203,546 B1 | 3/2001 | MacMahon | |
| 6,214,007 B1 | 4/2001 | Anderson | |
| 6,224,599 B1 | 5/2001 | Baynham et al. | |
| 6,264,694 B1 | 7/2001 | Weiler | |
| 6,277,149 B1 | 8/2001 | Boyle et al. | |
| 6,287,308 B1 | 9/2001 | Betz et al. | |
| 6,379,361 B1 | 4/2002 | Beck, Jr. et al. | |
| 6,423,063 B1 | 7/2002 | Bonutti | |
| 6,461,359 B1 | 10/2002 | Tribus et al. | |
| 6,478,800 B1 | 11/2002 | Fraser et al. | |
| 6,565,570 B2 | 5/2003 | Sterett et al. | |
| 6,575,982 B1 | 6/2003 | Bonutti | |
| 6,699,252 B2 | 3/2004 | Farr, II et al. | |
| 6,743,255 B2 | 6/2004 | Ferree | |
| 6,755,841 B2 | 6/2004 | Fraser et al. | |
| 6,796,986 B2 | 9/2004 | Duffner | |
| 6,823,871 B2 | 11/2004 | Schmieding | |
| 2002/0010513 A1 | 1/2002 | Schmieding | |
| 2002/0029084 A1 | 3/2002 | Paul et al. | |
| 2002/0095156 A1 | 7/2002 | Kuras et al. | |
| 2003/0028197 A1 | 2/2003 | Hanson et al. | |
| 2003/0105526 A1 | 6/2003 | Bryant et al. | |
| 2003/0171757 A1 | 9/2003 | Coon et al. | |
| 2003/0195516 A1 | 10/2003 | Sterett et al. | |
| 2003/0199881 A1 | 10/2003 | Bonutti | |
| 2004/0039387 A1 | 2/2004 | Gause et al. | |
| 2004/0249377 A1 | 12/2004 | Kaes et al. | |
| 2005/0075641 A1 | 4/2005 | Singhatat et al. | |
| 2005/0216090 A1 | 9/2005 | O'Driscoll et al. | |
| 2005/0228498 A1 | 10/2005 | Andres | |
| 2005/0251147 A1 | 11/2005 | Novak | |
| 2005/0273114 A1 | 12/2005 | Novak | |
| 2005/0273115 A1 | 12/2005 | Coon et al. | |
| 2006/0106396 A1 | 5/2006 | Justin et al. | |
| 2006/0122617 A1 | 6/2006 | Lavallee et al. | |
| 2006/0129163 A1 | 6/2006 | McGuire | |
| 2006/0149274 A1 | 7/2006 | Justin et al. | |
| 2006/0149275 A1 | 7/2006 | Cadmus | |
| 2006/0217808 A1 | 9/2006 | Novak et al. | |
| 2006/0241636 A1 | 10/2006 | Novak et al. | |
| 2007/0016209 A1 | 1/2007 | Ammann et al. | |

FOREIGN PATENT DOCUMENTS

| | | |
|---|---|---|
| EP | 1 099 428 | 5/2001 |
| EP | 1669033 | 6/2006 |
| FR | 2741525 | 5/1997 |
| FR | 2 764 183 | 12/1998 |
| WO | WO 96/14802 | 5/1996 |
| WO | WO 99/52473 | 10/1999 |
| WO | WO 2005/048888 | 6/2005 |
| WO | WO 2006/107800 | 10/2006 |

OTHER PUBLICATIONS

Sohn, Meniscus Transplantation: Current Concepts, The Journal of Knee Surgery, Apr. 2008, pp. 163-172, vol. 21, No. 2.

TOP VIEW

LATERAL VIEW

LATERAL VIEW

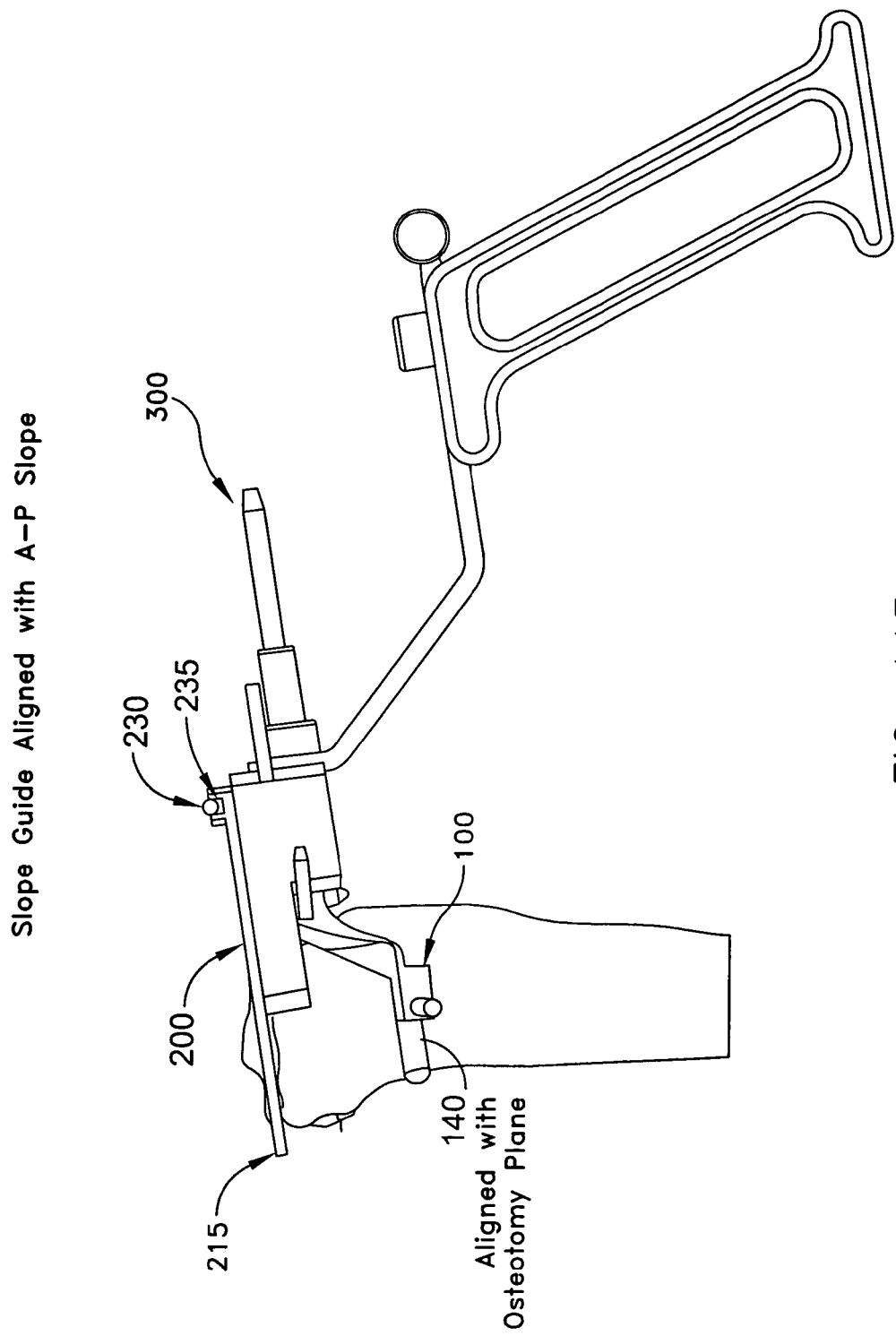

METHOD AND APPARATUS FOR PERFORMING AN OPEN WEDGE, HIGH TIBIAL OSTEOTOMY

REFERENCE TO PENDING PRIOR PATENT APPLICATIONS

This patent application claims benefit of prior U.S. Provisional Patent Application Ser. No. 60/860,595, filed Nov. 22, 2006 by Kelly Ammann et al. for METHOD AND APPARATUS FOR PERFORMING AN OPEN WEDGE, HIGH TIBIAL OSTEOTOMY.

The above-identified patent application is hereby incorporated herein by reference.

FIELD OF THE INVENTION

This invention relates to surgical methods and apparatus in general, and more particularly to surgical methods and apparatus for performing open wedge, high tibial osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to relatively unaffected portions of the joint.

Knee osteotomies are also an important technique for addressing abnormal knee geometries, e.g., due to birth defect, injury, etc.

Most knee osteotomies are designed to modify the geometry of the tibia, so as to adjust the manner in which the load is transferred across the knee joint.

There are essentially two ways in which to adjust the orientation of the tibia: (i) the closed wedge technique; and (ii) the open wedge technique.

With the closed wedge technique, a wedge of bone is removed from the upper portion of the tibia, and then the tibia is manipulated so as to close the resulting gap, whereby to reorient the lower portion of the tibia relative to the tibial plateau and hence adjust the manner in which load is transferred from the femur to the tibia.

With the open wedge technique, a cut is made into the upper portion of the tibia, the tibia is manipulated so as to open a wedge-like opening in the bone, and then the bone is secured in this position (e.g., by screwing metal plates to the bone or by inserting a wedge-shaped implant into the opening in the bone), whereby to reorient the lower portion of the tibia relative to the tibial plateau and hence adjust the manner in which load is transferred from the femur to the tibia.

While both closed wedge osteotomies and open wedge osteotomies provide substantial benefits to the patient, they are procedurally challenging for the surgeon. Among other things, with respect to open wedge osteotomies, it can be difficult to create the wedge-like opening in the bone with the necessary precision and with a minimum of trauma to the surrounding tissue (e.g., the neurological and vascular structures at the back of the knee). Furthermore, with open wedge osteotomies, it can be difficult to stabilize the upper and lower portions of the tibia relative to one another and to maintain them in this position while healing occurs.

The present invention is directed to open wedge, high tibial osteotomies of the knee, and is intended to provide increased precision and reduced trauma when creating the wedge-shaped opening in the bone, and to provide increased stability to the upper and lower portions of the tibia while healing occurs.

SUMMARY OF THE INVENTION

The present invention comprises a novel method and apparatus for performing an open wedge, high tibial osteotomy. More particularly, the present invention comprises the provision and use of a novel method and apparatus for forming an appropriate osteotomy cut into the upper portion of the tibia, manipulating the tibia so as to open an appropriate wedge-like opening in the tibia, and then inserting an appropriate wedge-shaped implant into the wedge-like opening in the tibia, so as to stabilize the tibia with the desired orientation, whereby to reorient the lower portion of the tibia relative to the tibial plateau and hence adjust the manner in which load is transferred from the femur to the tibia.

In one preferred form of the present invention, there is provided apparatus for performing an open wedge, high tibial osteotomy, the apparatus comprising:

a wedge-shaped implant for disposition in a wedge-shaped opening created in the tibia, wherein the wedge-shaped implant comprises at least two keys, laterally offset from one another, for disposition in corresponding keyholes formed in the tibia adjacent to the wedge-shaped opening created in the tibia.

In another form of the present invention, there is provided a method for performing an open wedge, high tibial osteotomy, the method comprising:

cutting the bone along a cutting plane, with the cut terminating at a boundary line, and forming at least two keyholes in the tibia adjacent to the cut, wherein the two keyholes are laterally offset from one another;

moving the bone on either side of the cut apart so as to form a wedge-like opening in the bone; and positioning a wedge-shaped implant in the wedge-shaped opening created in the tibia, wherein the wedge-shaped implant comprises at least two keys, laterally offset from one another, and further wherein the at least two keys are disposed in the at least two keyholes formed in the tibia.

In another form of the present invention, there is provided apparatus for performing an open wedge, high tibial osteotomy, the apparatus comprising:

a wedge-shaped implant for disposition in a wedge-shaped opening created in the tibia, wherein the wedge-shaped implant comprises at least two keys, vertically offset from one another, for disposition in corresponding keyholes formed in the tibia adjacent to the wedge-shaped opening created in the tibia, and a shear rib, laterally offset from the at least two keys, for disposition in a corresponding shear rib keyhole formed in the tibia adjacent to the wedge-shaped opening created in the tibia.

In another form of the present invention, there is provided a method for performing an open wedge, high tibial osteotomy, the method comprising:

cutting the bone along a cutting plane, with the cut terminating at a boundary line, and forming at least two keyholes in the tibia adjacent to the cut, wherein the two keyholes are vertically offset from one another, and forming a shear rib keyhole in the tibia adjacent to the cut, wherein the shear rib keyhole is laterally offset from the at least two keyholes;

moving the bone on either side of the cut apart so as to form a wedge-like opening in the bone; and positioning a wedge-shaped implant in the wedge-shaped opening created in the tibia, wherein the wedge-shaped implant comprises at least two keys, vertically offset from one another, and a shear rib, laterally offset from the at least two keys, and further wherein the at least two keys are disposed in the at least two keyholes formed in the tibia, and the shear rib is disposed in the shear rib keyhole formed in the tibia.

In another form of the present invention, there is provided a shear rib end mill comprising:

a shaft having a distal end and a proximal end, and a relief area formed on the shaft proximal to the distal end;

a cutting edge formed on the shaft distal to relief area, and a flute communicating with the cutting edge and extending into relief area; and a stop formed on the shaft, proximal to the relief area.

In yet another form of the present invention, there is provided an osteotomy implant for disposition in a wedge-shaped osteotomy opening in a bone, the implant comprising:

a body for disposition within the wedge-shaped osteotomy opening in the bone and supporting the bone while healing occurs;

at least one key formed integral with the body for stabilizing the body relative to the adjacent bone while healing occurs; and at least one fenestration extending through the body for permitting bone growth through the implant.

In still another form of the present invention, there is provided an osteotomy implant for disposition in a wedge-shaped osteotomy opening in a bone, the implant comprising:

a body for disposition within the wedge-shaped osteotomy opening in the bone and supporting the bone while healing occurs; and at least one key formed integral with the body for stabilizing the body relative to the adjacent bone while healing occurs;

wherein at least a portion of the body and the at least one key are formed out of a relatively strong, load-bearing material whereby to stabilize the bone during healing;

and further wherein at least a portion of the body is formed out of a bone growth-promoting material whereby to enhance bone healing across the osteotomy opening in the bone.

In another form of the present invention, there is provided a method for performing an open wedge, high tibial osteotomy, the method comprising:

providing an osteotomy implant, the osteotomy implant comprising:

a body for disposition within the wedge-shaped osteotomy opening in the bone and supporting the bone while healing occurs;

at least one key formed integral with the body for stabilizing the body relative to the adjacent bone while healing occurs; and at least one fenestration extending through the body for permitting bone growth through the implant;

cutting the tibia along a cutting plane, with the cut terminating at a boundary line, and forming at least one keyhole in the tibia adjacent to the cut;

moving the bone on either side of the cut apart so as to form a wedge-shaped osteotomy opening in the bone; and positioning the osteotomy implant in the wedge-shaped osteotomy opening in the tibia, wherein the body of the osteotomy implant is disposed within the wedge-shaped osteotomy opening in the tibia and the at least one key is disposed in the at least one keyhole formed in the tibia.

In yet another form of the present invention, there is provided a method for performing an open wedge, high tibial osteotomy, the method comprising:

providing an osteotomy implant, the osteotomy implant comprising:

a body for disposition within the wedge-shaped osteotomy opening in the bone and supporting the bone while healing occurs; and at least one key formed integral with the body for stabilizing the body relative to the adjacent bone while healing occurs;

wherein at least a portion of the body and the at least one key are formed out of a relatively strong, load-bearing material whereby to stabilize the bone during healing;

and further wherein at least a portion of the body is formed out of a bone growth-promoting material whereby to enhance bone healing across the osteotomy opening in the bone;

cutting the tibia along a cutting plane, with the cut terminating at a boundary line, and forming at least one keyhole in the tibia adjacent to the cut;

moving the bone on either side of the cut apart so as to form a wedge-shaped osteotomy opening in the bone; and positioning the osteotomy implant in the wedge-shaped osteotomy opening in the tibia, wherein the body of the osteotomy implant is disposed within the wedge-shaped osteotomy opening in the tibia and the at least one key is disposed in the at least one keyhole formed in the tibia.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Overview of an Open Wedge, High Tibial Osteotomy

Figure 1:
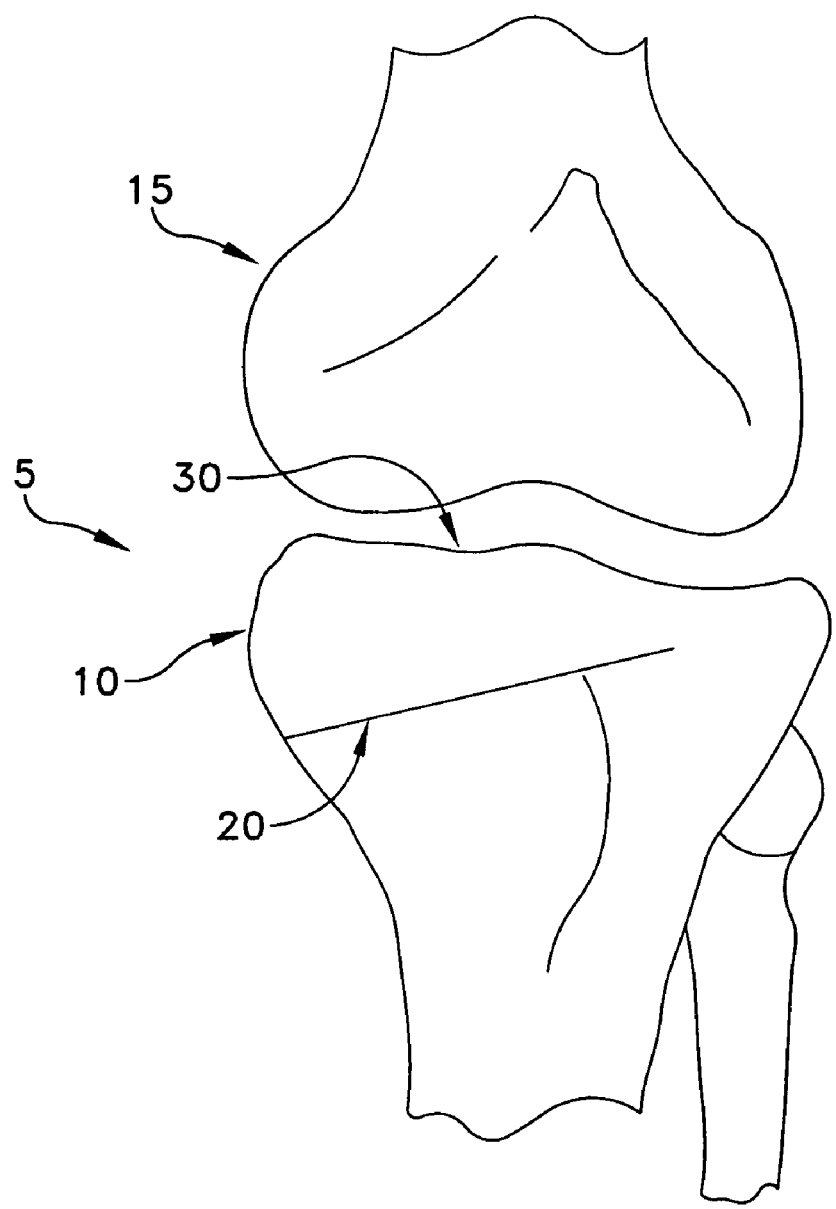
FIGS. 1-3 are schematic views showing the formation of a wedge-like opening in the tibia for an open wedge, high tibial osteotomy, and positioning of a wedge-shaped implant into the wedge-like opening in the tibia.
Figure 2:
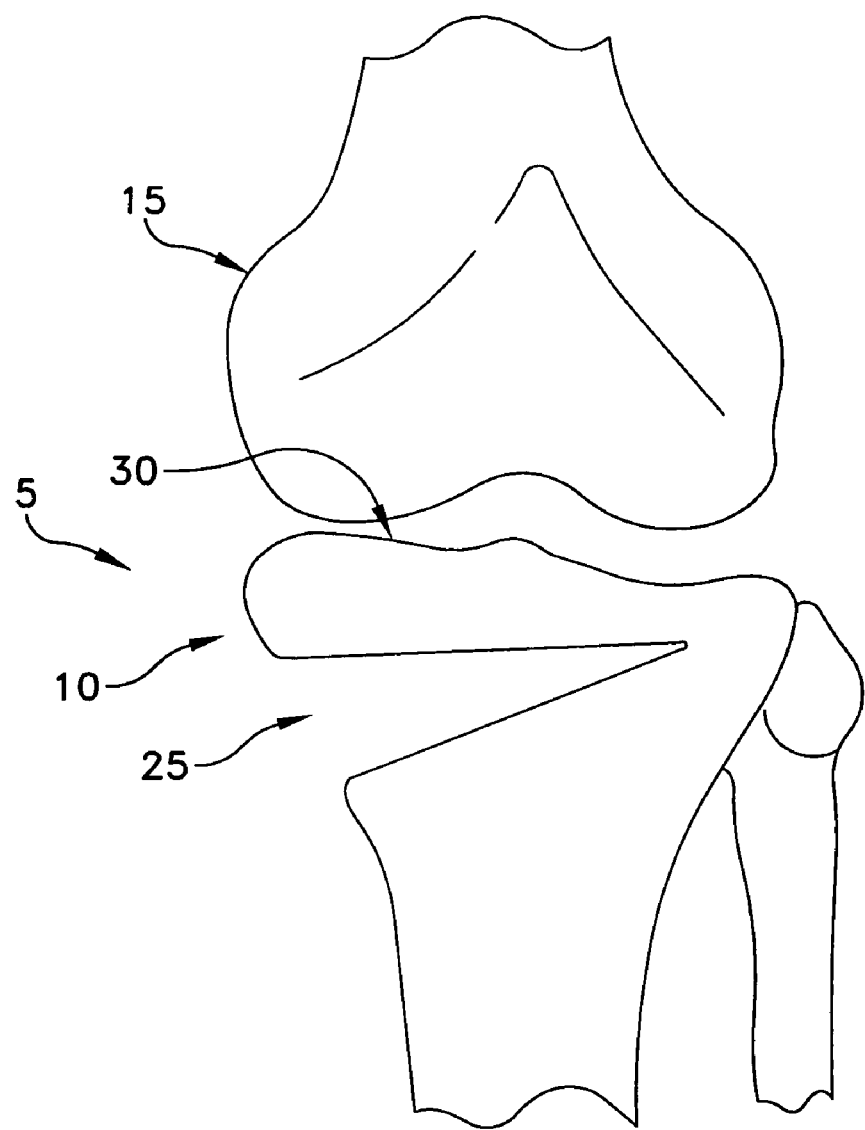
Figure 3:
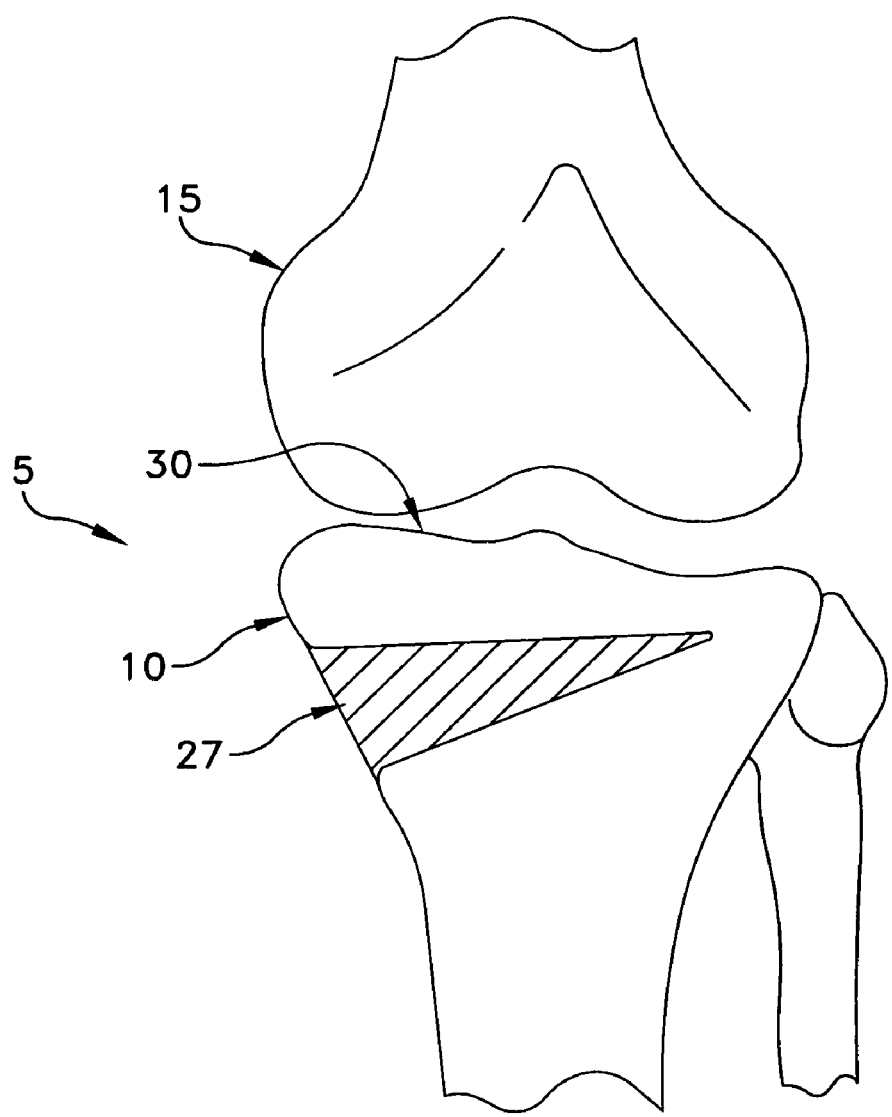

Looking first at FIGS. 1-3, there is shown a knee joint 5 upon which an open wedge osteotomy is to be performed. Knee joint 5 generally comprises a tibia 10 and a femur 15. In accordance with the present invention, the open wedge osteotomy is effected by first making a cut 20 (FIG. 1) into the upper tibia, and then manipulating the lower portion of the tibia so as to open a wedge-like opening 25 (FIG. 2) in the bone, with the wedge-like opening 25 being configured so as to adjust the manner in which load is transferred from the femur to the tibia. In this respect, it should be appreciated that a variety of methods are well known in the art for determining the degree of correction necessary to correctly re-align the weight-bearing axis of the knee. Furthermore, cut 20 and wedge-like opening 25 may be formed in a variety of ways well known in the art.

Among other things, the present invention provides a new and improved method and apparatus for forming cut 20 and wedge-like opening 25, as will be discussed in detail below.

Once the desired wedge-like opening 25 has been formed in tibia 10 so as to reconfigure tibia 10 to the desired geometry, the bone may be secured in position in a variety of ways well known in the art (e.g., by screwing metal plates to the bone or by inserting a wedge-shaped implant into the opening in the bone), whereby to adjust the manner in which the load is transferred from the femur to the tibia. By way of example, FIG. 3 shows a wedge-shaped implant 27 inserted into the wedge-like opening 25 formed in the tibia, whereby to stabilize the tibia in its reconfigured geometry.

Among other things, the present invention also provides a new and improved wedge-shaped implant, and an associated method and apparatus for deploying the same into the wedge-shaped opening in the tibia, as will be discussed in detail below.

Figure 3A:
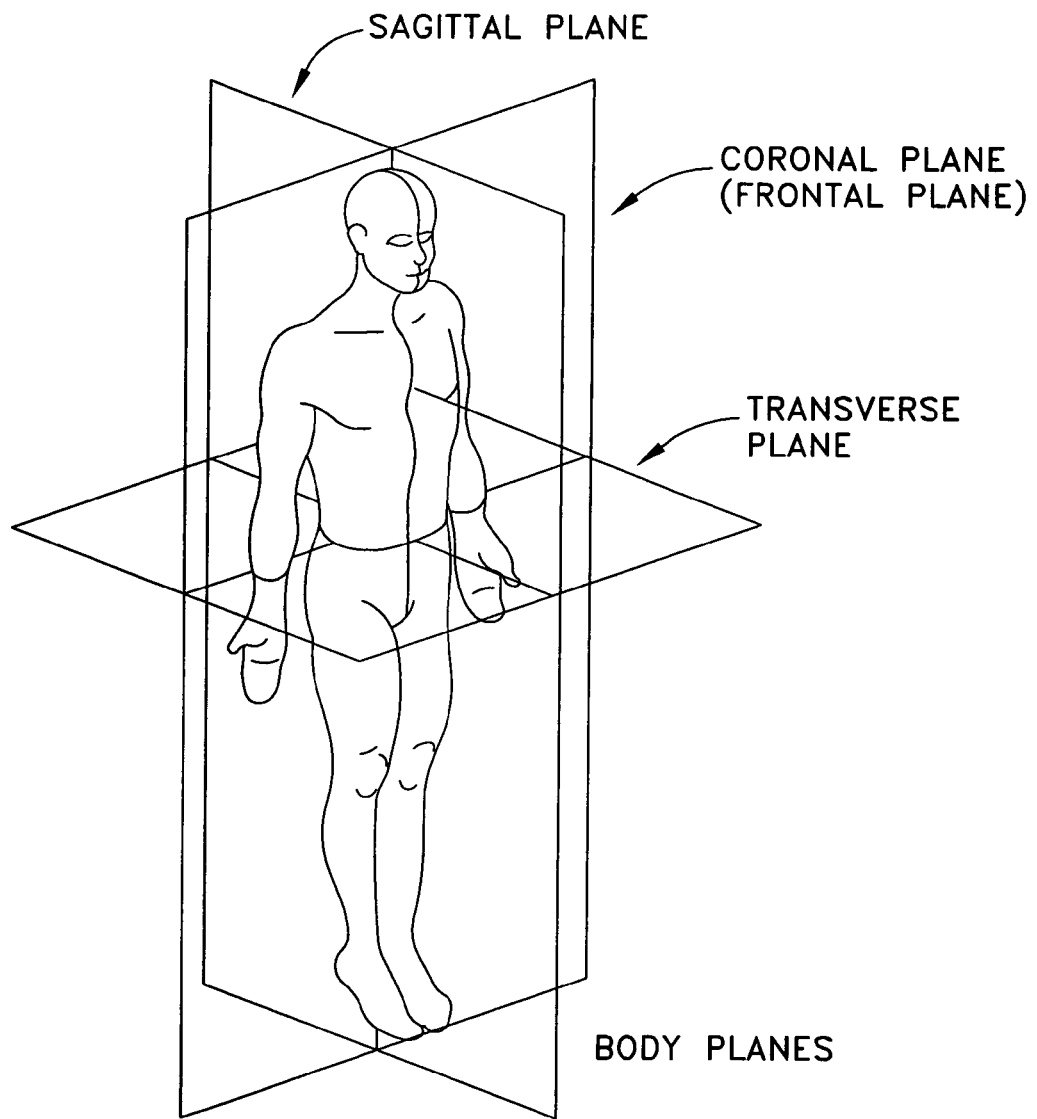
FIG. 3A is a schematic view showing selected anatomical planes.

Discussion of the Relevant Planar Surfaces in the Open Wedge, High Tibial Osteotomy of the Present Invention In order to appreciate certain aspects of the present invention, it is helpful to have a thorough understanding of the planar surfaces of the tibia that are relevant in performing the open wedge, high tibial osteotomy of the present invention. Thus, the following discussion presents a geometric description of the planar surfaces that are relevant to the open wedge, high tibial osteotomy of the present invention. For the purposes of the present discussion, it can sometimes be helpful to make reference to selected anatomical planes, e.g., the coronal plane, the sagittal plane and the transverse plane (FIG. 3A).

Figure 4:
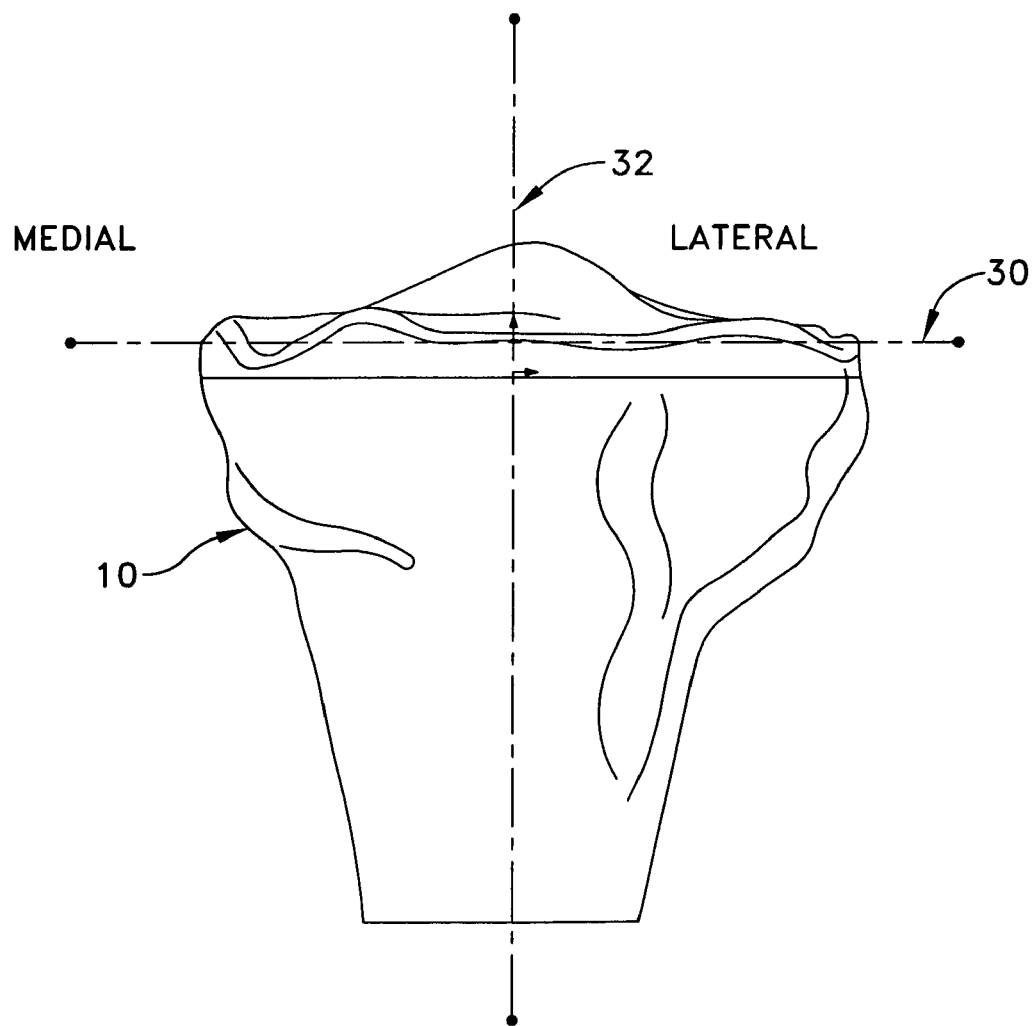
FIGS. 4-9 show the relevant planar surfaces in an open wedge, high tibial osteotomy conducted in accordance with the present invention.
Figure 5:
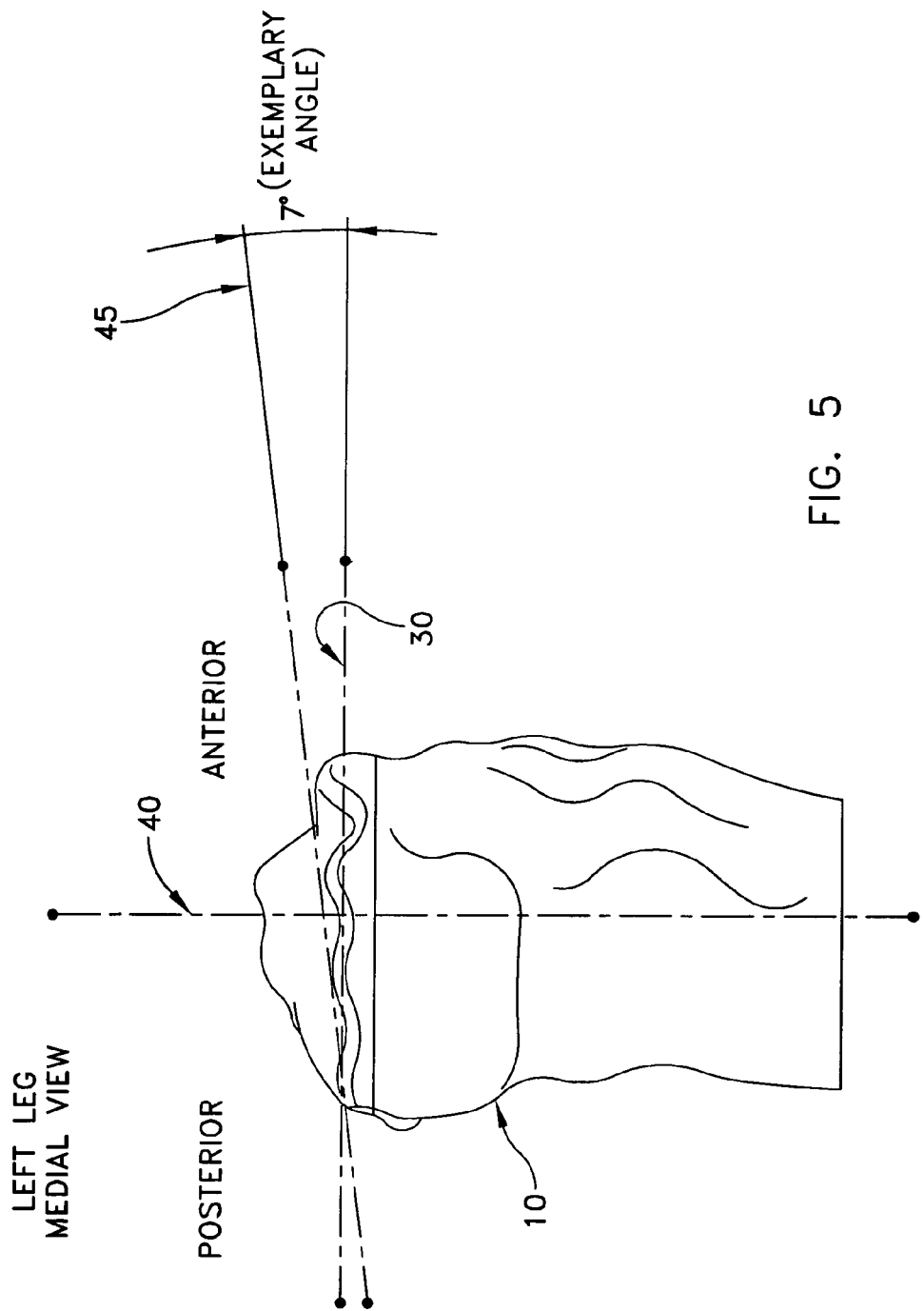

Looking now at FIGS. 1-4, for the purposes of the present invention, the tibial plateau 30 may be described as a horizontal (or transverse) plane that extends along the top surface of tibia 10. For reference, the sagittal plane 32 is also shown in FIG. 4. As seen in FIG. 5, tibial plateau 30 is also perpendicular to the frontal (or coronal) plane 40. The anterior-posterior (A-P) slope is defined by an anterior-posterior (A-P) slope plane 45 that extends along the sloping top surface of the tibia, from anterior-to-posterior. Published research has demonstrated that the anterior-posterior (A-P) slope typically extends at an angle of approximately 7° to 11° to the tibial plateau 30; however, the specific angle may vary from individual to individual.

Figure 6:
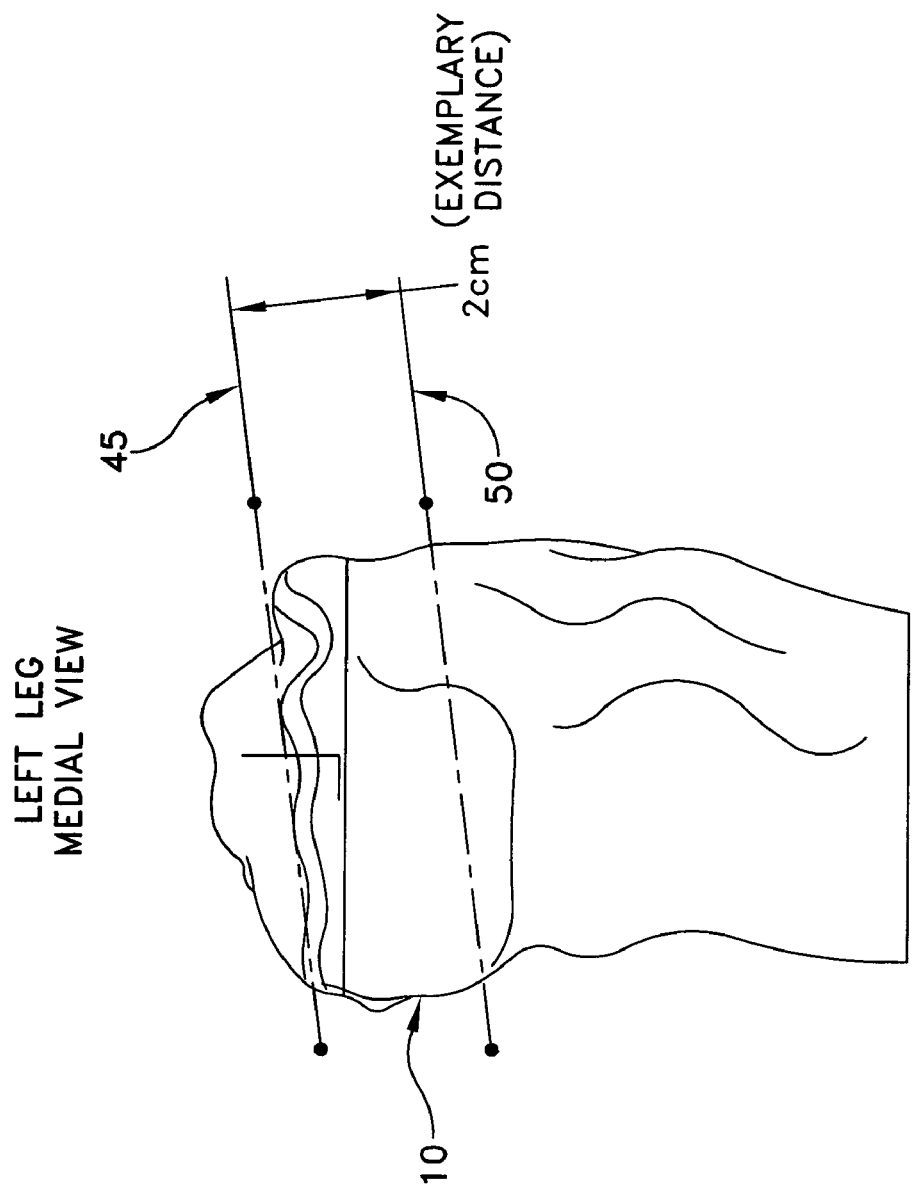

Looking next at FIG. 6, for the open wedge, high tibial osteotomy of the present invention, it is generally desirable to stay about 2 cm inferior to the A-P slope plane 45. This offset can be referred to as the A-P offset plane 50.

Figure 7:
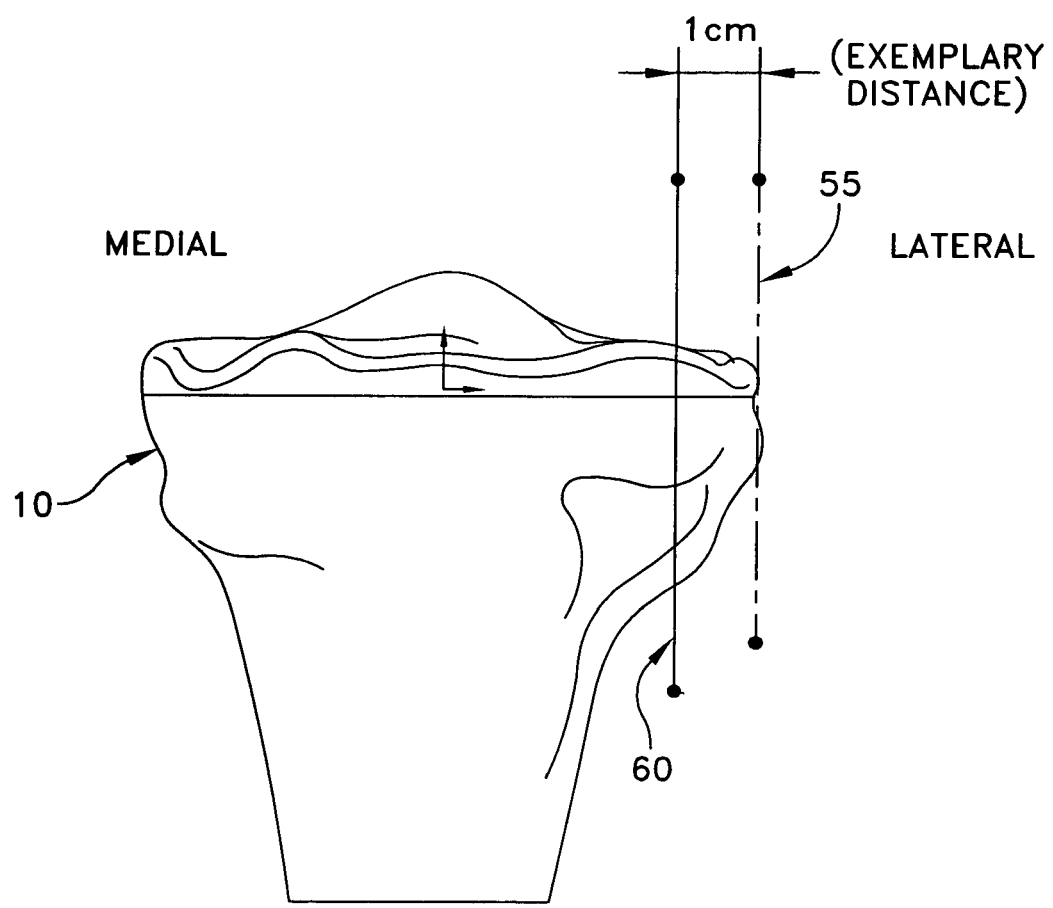

As seen in FIG. 7, the lateral aspect and cut depth of the cut 20 may be defined by a lateral aspect plane 55 and a cut depth plane 60, with the cut depth being about 1 cm medial to the lateral aspect of the tibia.

Figure 8:
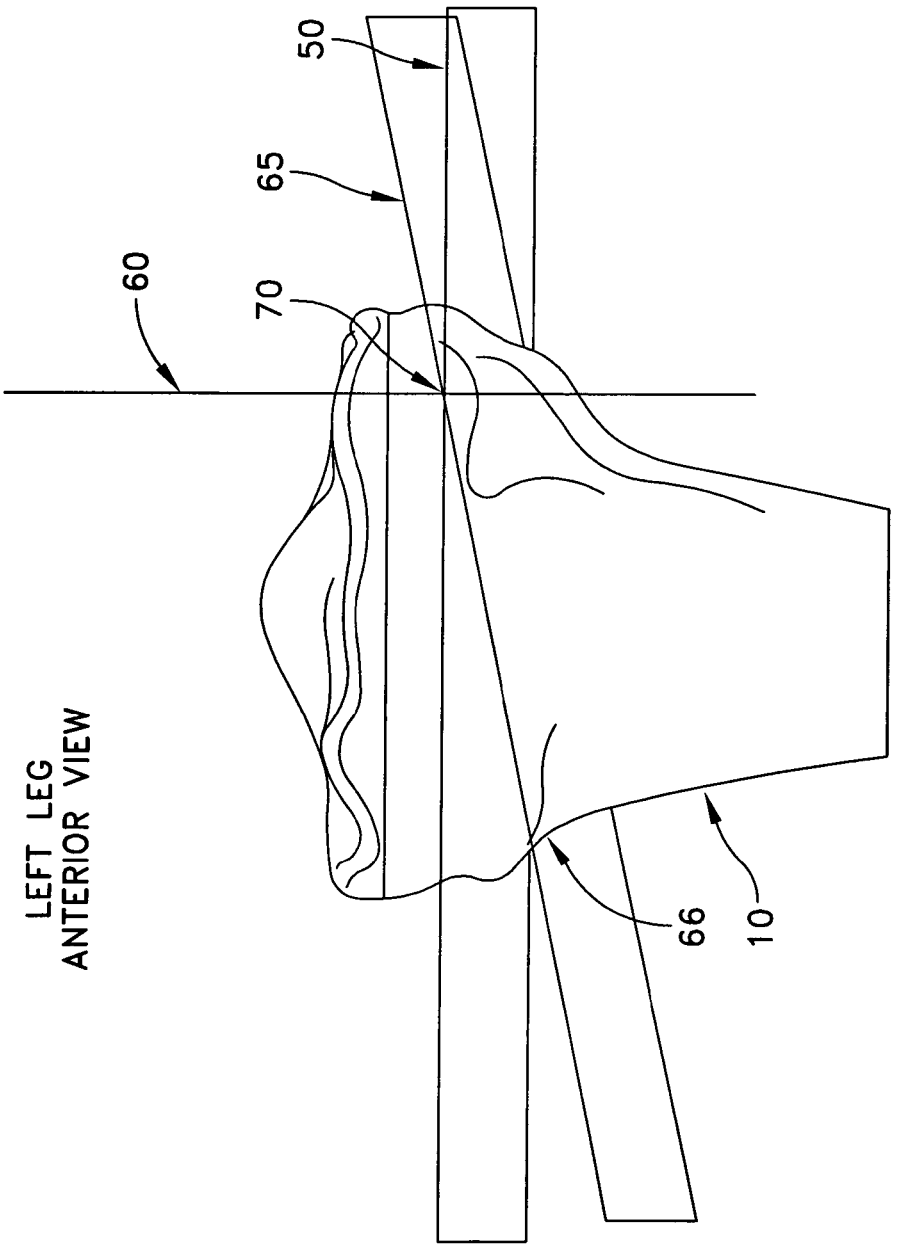

Looking next at FIG. 8, the osteotomy cut plane 65 (when seen from the direct frontal view of FIG. 8) is formed by a plane that is rotated away from the A-P offset plane 50 through an axis which is formed by the intersection of the cut depth plane 60 and the A-P offset plane 50. The degree of rotation is selected so as to be sufficient to place the entry of the osteotomy cut plane 65 at the medial neck 66 (FIG. 8) of the tibia. It should be noted that the A-P offset plane 50 and the osteotomy cut plane 65 are "tilted" slightly from anterior to posterior (but not seen in the direct frontal view of FIG. 8), since the A-P offset plane 50 and the osteotomy cut plane 65 follow the tilt of the A-P slope plane 45 (FIG. 6). The intersection of the A-P offset plane 50 and the cut depth plane 60 forms an axis 70 which, in accordance with the present invention, defines the lateral limit of the osteotomy cut 20. In other words, axis 70 defines a line through the tibia which is (i) parallel to A-P slope plane 45, and (ii) contained within osteotomy cut plane 65. Furthermore, in accordance with the present invention, axis 70 is used to define the lateral limit of the osteotomy cut 20 which is to be made into the tibia.

Figure 9:
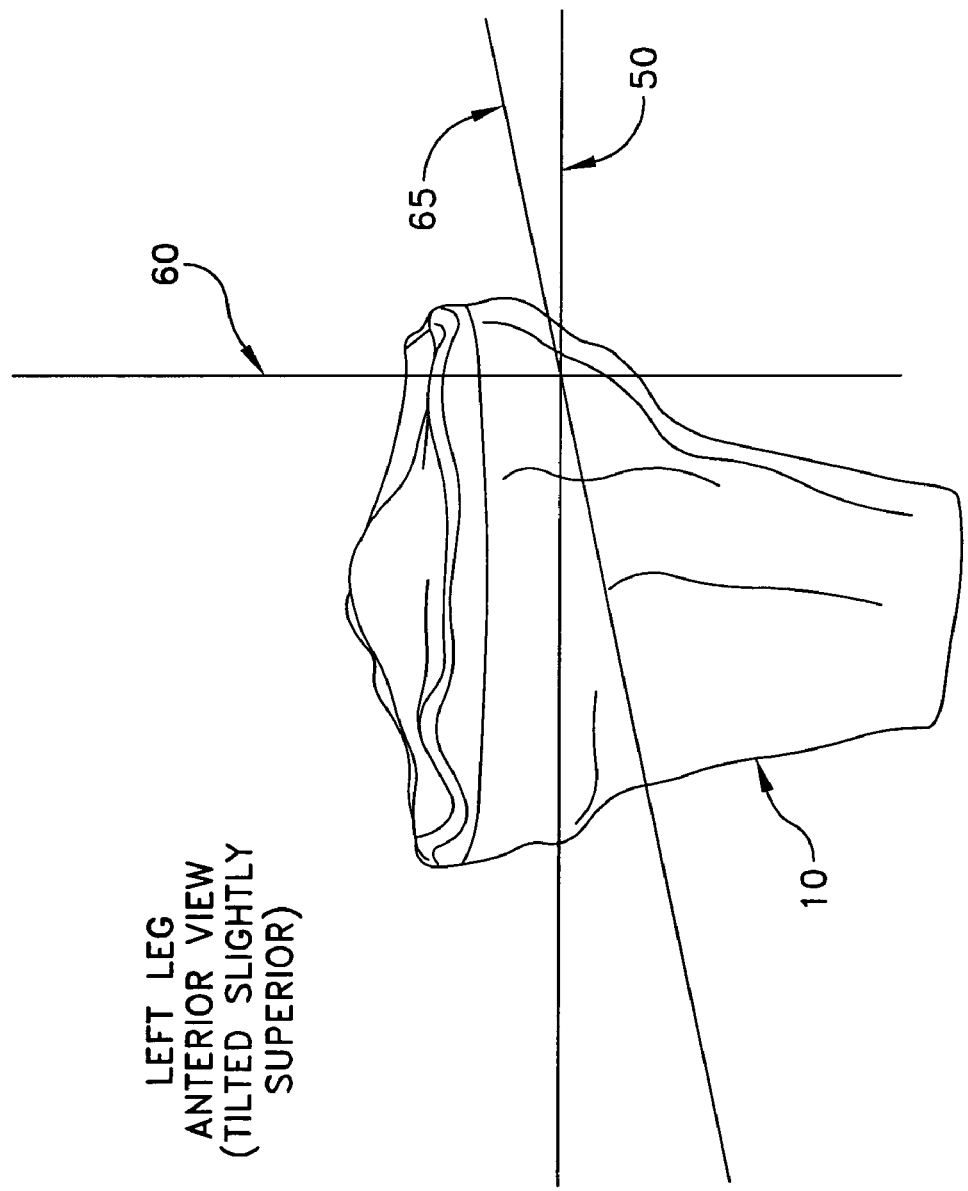

As seen in FIG. 9, the direct view of the osteotomy plane is a direct view in line with the osteotomy. This view is tilted downward (e.g., at an angle of approximately 7°) from the direct frontal view. Again, the angle of tilt downward is equal to the A-P slope. In other words, with the present invention, the osteotomy cut plane 65 extends parallel to the A-P slope plane 45 (in the anterior-to-posterior direction, although not in the medial-to-lateral direction), and typically slopes downward (e.g., at an angle of approximately 7-11°) when viewed in the anterior-to-posterior direction. Furthermore, with the present invention, the axis 70 (which defines the lateral limit to the osteotomy cut 20) is contained within the osteotomy cut plane 65.

Figure 16:
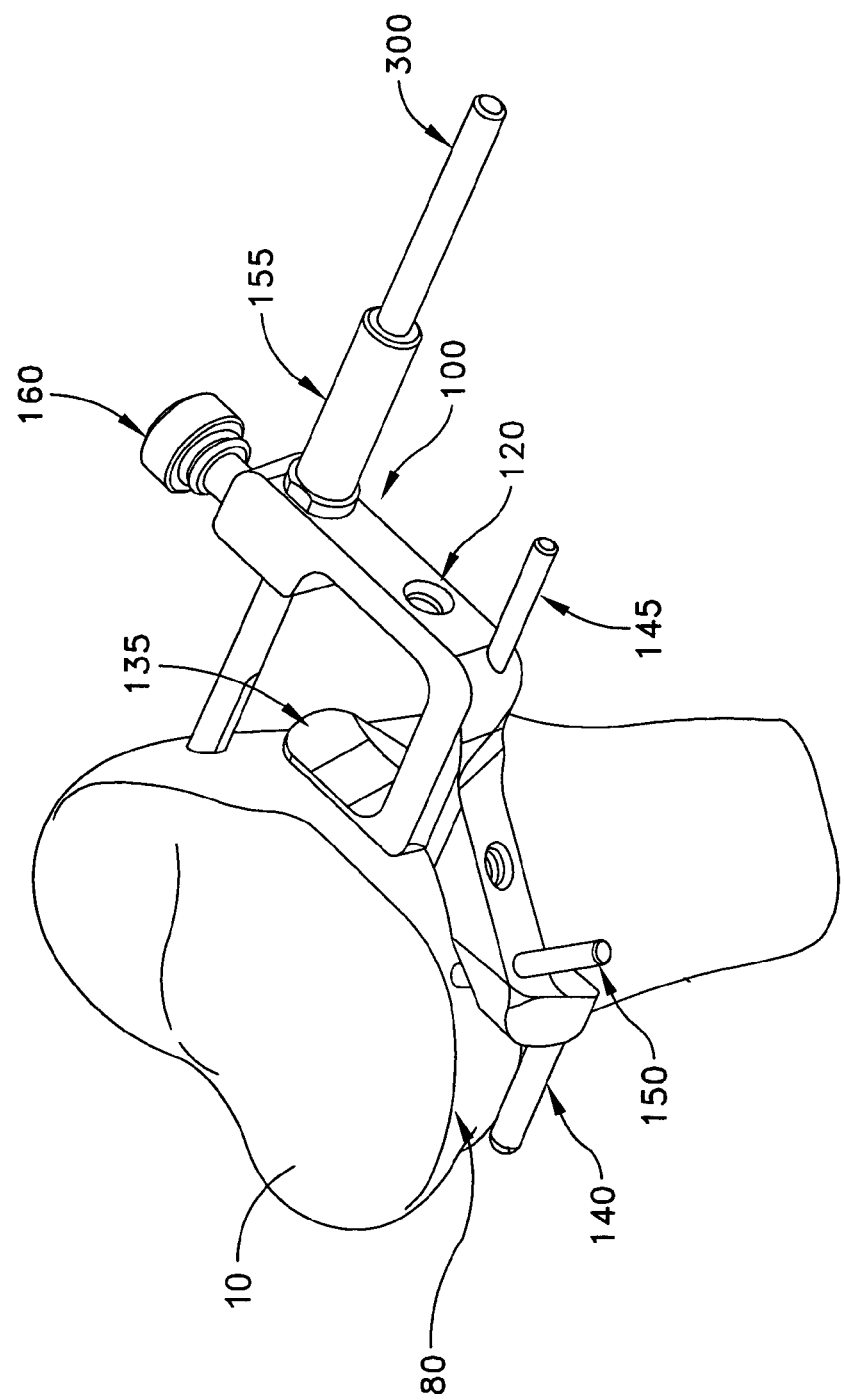
Figure 18:
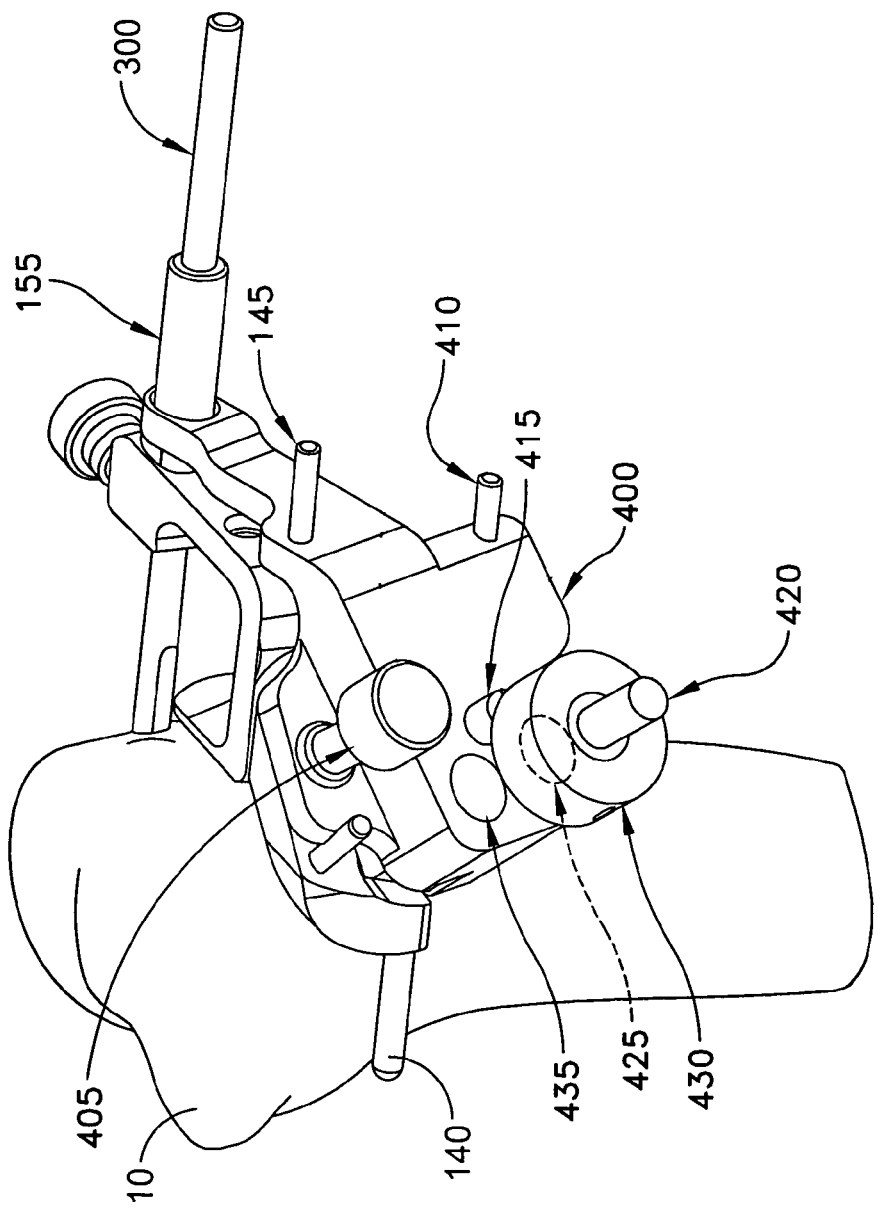

Novel Method and Apparatus for Performing the Open Wedge, High Tibial Osteotomy of the Present Invention In one preferred embodiment of the present invention, there is provided a novel osteotomy system which comprises instrumentation for use in making precise and repeatable osteotomy cuts for use in open wedge, high tibial osteotomies, preferably using an antero-medial approach. The novel osteotomy system generally comprises a positioning guide 100 (FIG. 16), a slope guide 200 (FIG. 11), an apex pin 300 (FIG. 16), a keyhole drill guide 400 (FIG. 18), a posterior protector 500 (FIG. 20), and a cutting guide 600 (FIG. 20), as will hereinafter be discussed in further detail.

Figure 22:
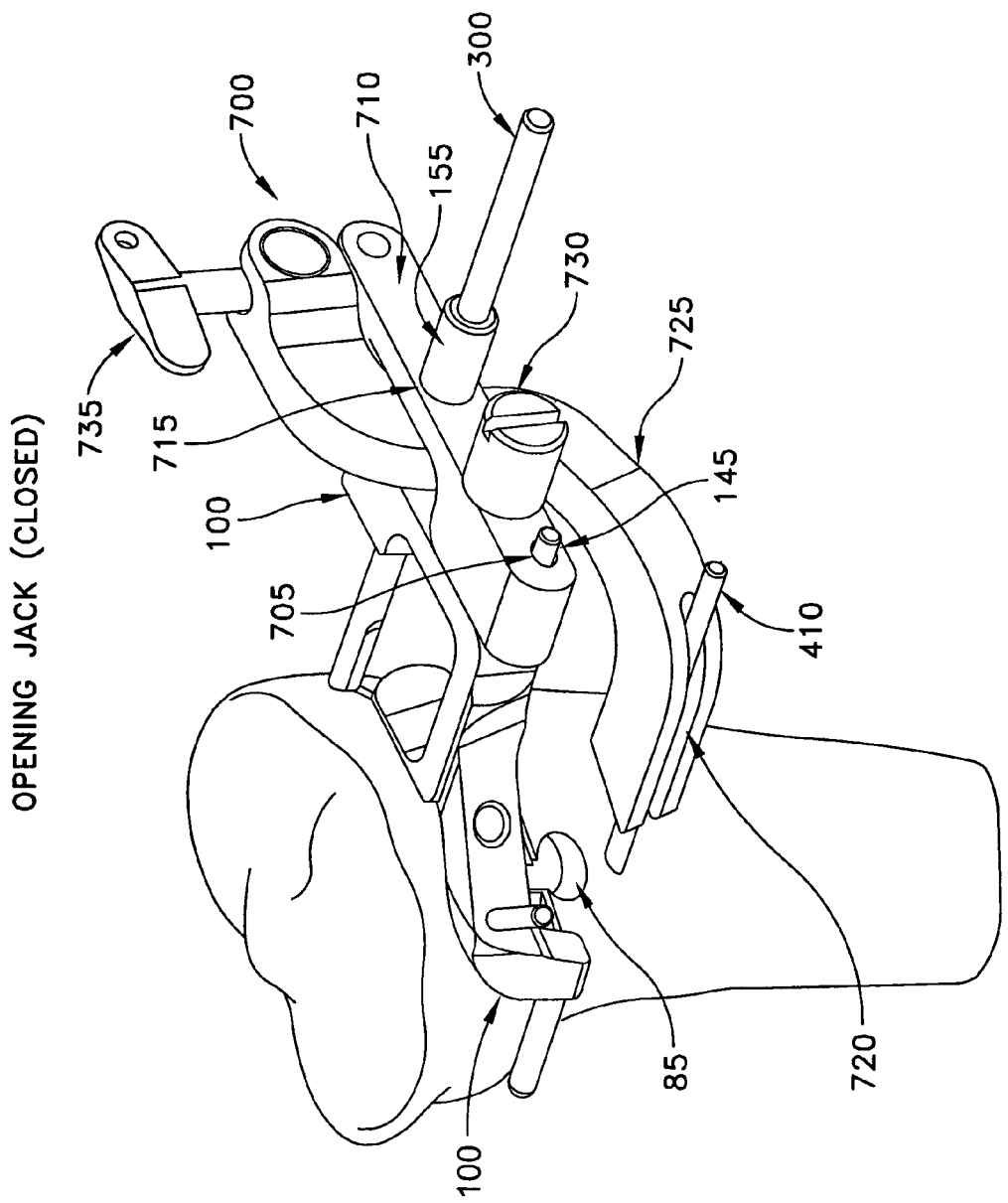

The novel osteotomy system preferably also comprises a novel opening jack 700 (FIG. 22) for opening the cut 20 in the tibia so as to form the wedge-like opening 25 in the tibia, as will also hereinafter be discussed in further detail.

And the novel osteotomy system preferably also includes a novel implant 800 (FIG. 24) for positioning in the wedge-like opening in the tibia so as to stabilize the tibia in its corrected configuration, as will also hereinafter be discussed in further detail. Furthermore, in some instances, it may be advantageous to use an implant trial base 830 (FIGS. 27 and 28) in the course of preparing the tibia to receive implant 800, and in order to confirm proper fit of implant 800 in its seat, as will also hereinafter be discussed in further detail.

Thus, with the present invention, the surgeon first determines (using methods well known in the art) the degree of correction necessary to correctly re-align the weight-bearing axis of the knee; then the surgeon uses the system to make the appropriate cut 20 into the tibia; then the surgeon opens the bone cut to the extent required so as to form the desired wedge-like opening 25 in the tibia; and then the surgeon stabilizes the tibia in its corrected configuration (e.g., with the novel implant 800) while healing occurs.

In a preferred form of the invention, the novel osteotomy system is configured so that:

(i) the axis 70 formed at the lateral limit of the osteotomy cut 20 (which forms the lateral limit of the remaining bony hinge when the osteotomy cut 20 is thereafter opened) is parallel to the A-P tibial slope;

(ii) the axis of the lateral limit of the bony hinge created by the osteotomy cut lies in a plane that is perpendicular to the frontal (i.e., coronal) plane; and (iii) when the osteotomy cut 20 is completed and the wedge is opened, the distal (i.e., lower) tibia is rotated about the bony hinge so as to substantially maintain, in anatomical alignment, the A-P slope and the frontal plane.

In a preferred form of the invention, the novel osteotomy system is also configured so that:

(iv) the osteotomy can be performed less invasively; and (v) the osteotomy can be performed with minimum incising of soft tissue such as the medial collateral ligament, the lateral collateral ligament, and the hamstrings.

In a preferred form of the invention, the novel osteotomy system is also configured so that the delicate neurological and vascular tissues at the back of the knee are fully protected during the osteotomy procedure.

In one preferred form of the present invention, the novel osteotomy system is constructed and used as follows.

1. A vertical incision is first made on the antero-medial portion of the knee, approximately 1 cm from the medial edge of the patellar tendon, with the incision beginning approximately 2.5-3 cm superior to the anterior tibial tubercle, and extending approximately 6-10 cm in length.

2. The soft tissue between the patellar tendon and the proximal surface of the tibia is then dissected in order to make a small tunnel-like opening beneath the patellar tendon, just above the patellar tendon's insertion to the proximal tibia.

3. Looking now at FIG. 10, an assembly comprising positioning guide 100 (FIGS. 10 and 16), slope guide 200 (FIGS. 10 and 11) and an introducer 105 (FIGS. 10 and 11) is advanced to the surgical site. Preferably the assembly of positioning guide 100, slope guide 200 and introducer 105 is pre-assembled prior to opening the skin. This assembly is assembled by first mounting slope guide 200 to positioning guide 100, and then mounting introducer 105 to both slope guide 200 and positioning guide 100 by using a screw 115 (FIG. 10) which passes through slope guide 200 and is received in a threaded bore 120 (FIG. 16) formed in positioning guide 100.

In one preferred form of the invention, slope guide 200 may comprise two separate elements which are secured together, e.g., a base 210 and a guide element 215 which are connected together by pins 205, with base 210 being formed out of a radio-translucent material (e.g., plastic) and guide element 215 being formed out of a radio-opaque material (e.g., stainless steel), whereby guide element 215 will be visible under fluoroscopy and base 210 will be effectively invisible under fluoroscopy, as will hereinafter be discussed.

In one preferred form of the invention, introducer 105 may comprise an arm 125 and a handle 130. Arm 125 and handle 130 may be formed as two separate elements secured together, or arm 125 and handle 130 may be formed as a singular construction.

4. Next, the foregoing assembly is maneuvered so that a tibial tubercle locating tab 135 (FIGS. 10 and 16) of positioning guide 100 is inserted between the patellar tendon (not shown) and the tibia, and so that tibial tubercle locating tab 135 is set against the superior margin of the tibial tubercle. In this way, the tibial tubercle provides a rough alignment guide for aligning positioning guide 100 with the tibia. If desired, the underside of tibial tubercle locating tab 135 may include serrations, ridges, ribs, etc. 137 (FIG. 11E) so as to facilitate stabilization of tibial tubercle locating tab 135 (and hence the instrumentation) against the tibia.

5. Using a lateral fluoroscope view, taken from the medial side at the level of the tibial plateau, the assembly is then aligned so that the underside surface 220 (FIG. 11) of guide element 215 of slope guide 200 is aligned with the top of the medial condyle 75 of the tibia. Alternatively, if the surgeon prefers to shift the osteotomy slightly distally on the tibia, the top edge 225 of guide element 215 of slope guide 200 can be aligned with medial condyle 75, thereby offsetting the osteotomy by a fixed distance distally (e.g., 3 mm).

By forming the guide element 215 of slope guide 200 out of a radio-opaque material and by forming the base 210 of slope guide 200 out of a radio-translucent material, base 210 will be effectively invisible under fluoroscopy and guide element 215 will stand out in clear relief against the bone.

It should be noted that guide element 215 of slope guide 200 is preferably formed with a "Z shape" (FIGS. 10 and 11A) so as to provide additional functionality. More particularly, by forming guide element 215 with a "Z shape", several significant advantages are obtained.

Figure 11:
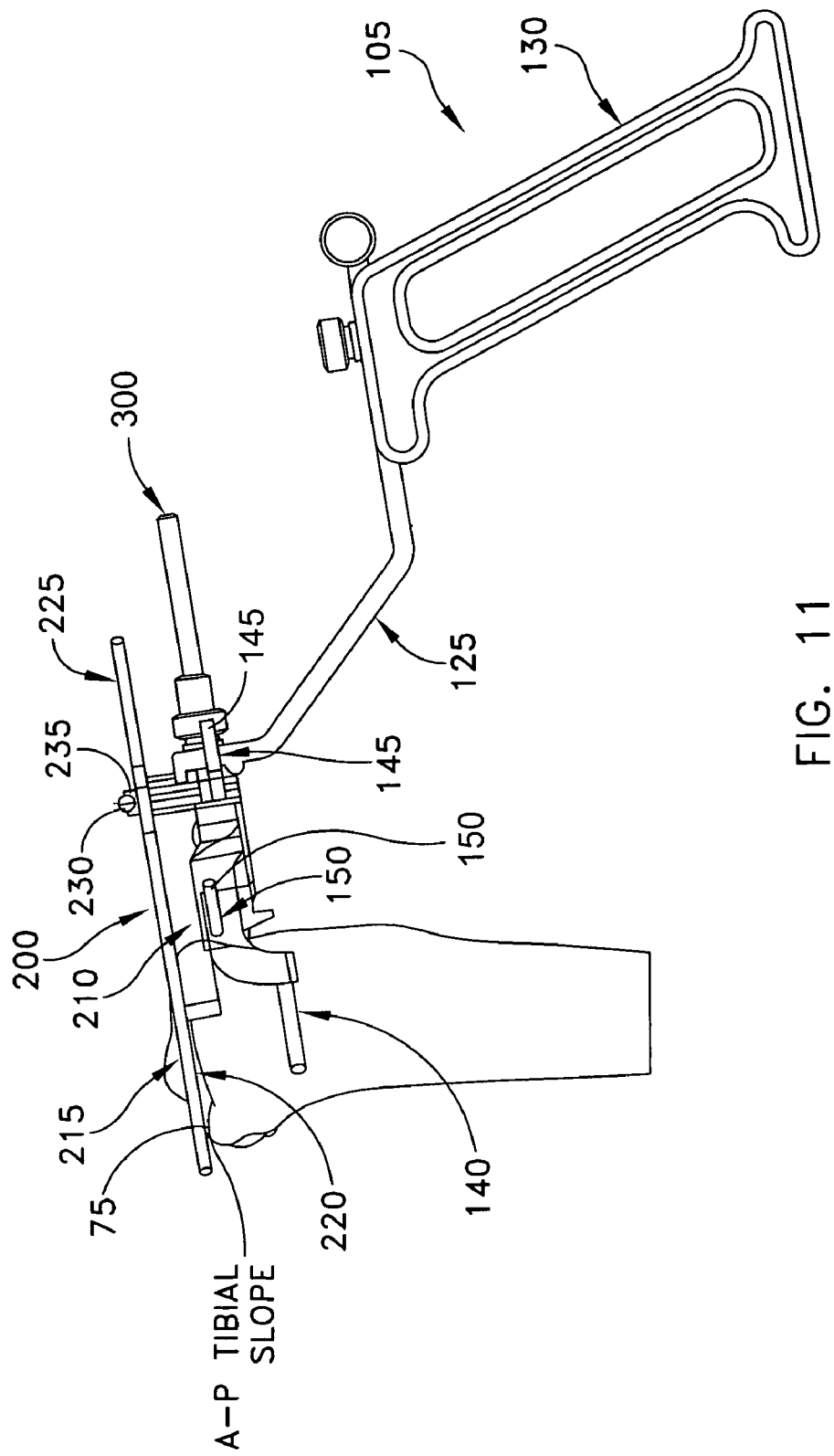
Figure 11A:
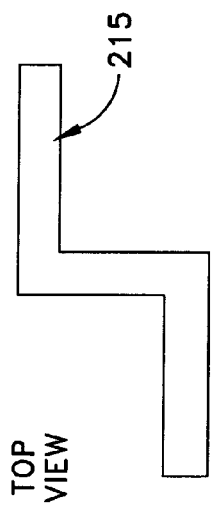
Figure 11B:
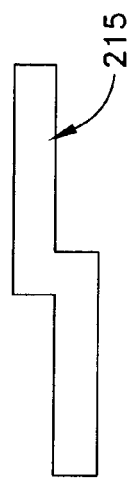
Figure 11C:
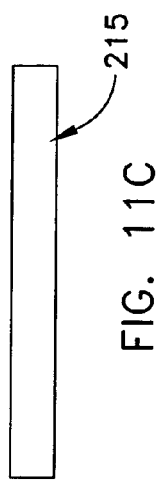

First, this construction permits guide element 215 to wrap around the perimeter of the tibia. Second, the "Z shape" of guide element 215 also operates to indicate if the slope guide is not vertically aligned with the level of the fluoroscope. More particularly, if slope guide 200 is not vertically aligned with the level of the fluoroscope, the "Z shape" of guide element 215 will appear as a jagged or zig-zag shape on the fluoroscope (FIG. 11B). However, if guide element 215 is vertically aligned with the level of the fluoroscope, then the guide element will appear as a straight line on the fluoroscope (FIGS. 11 and 11C).

This vertical alignment is important, since it enables alignment of slope guide 200 (and hence positioning guide 100) with the medial condyle, i.e., with the A-P slope plane.

Figure 11D:
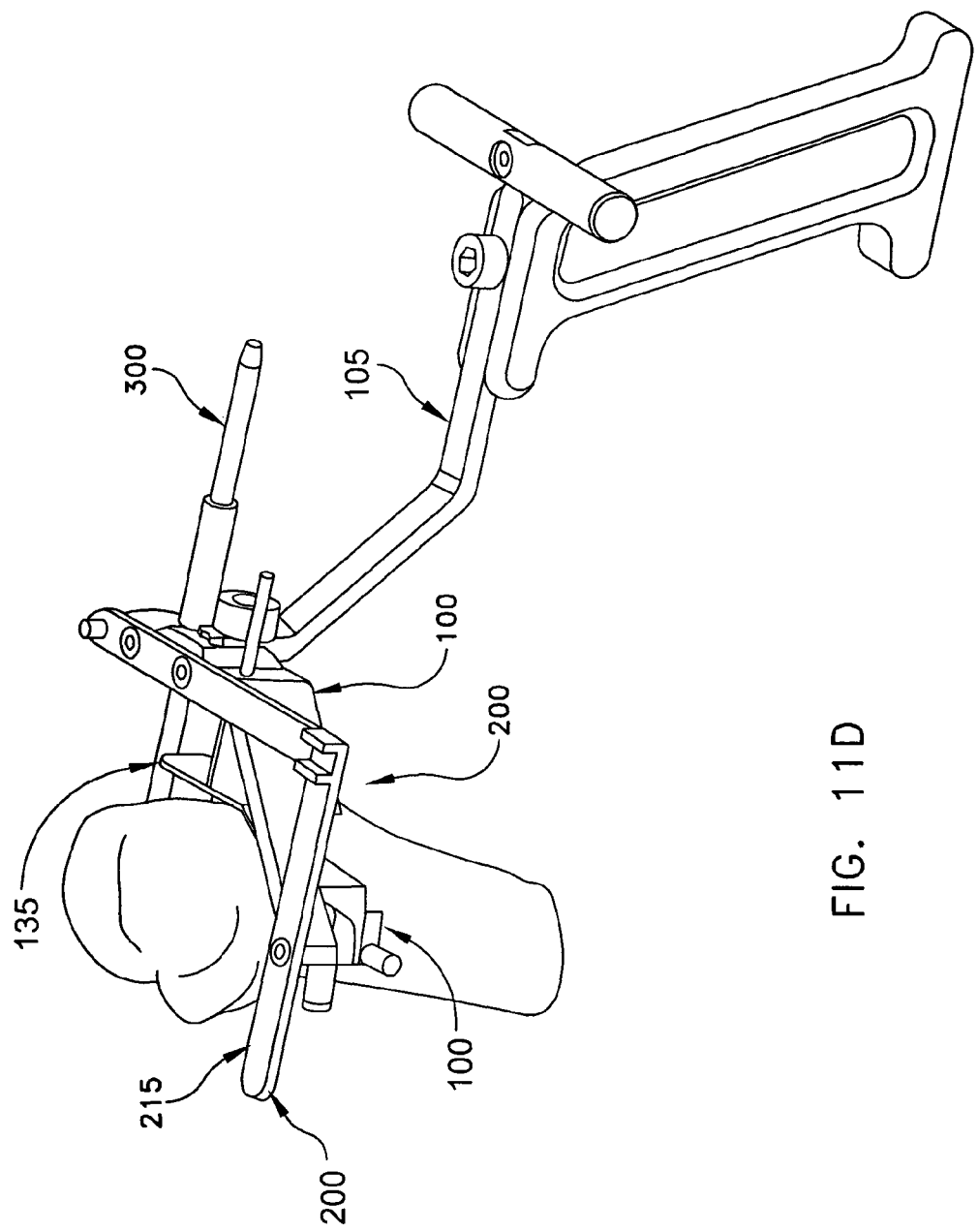
Figure 11E:
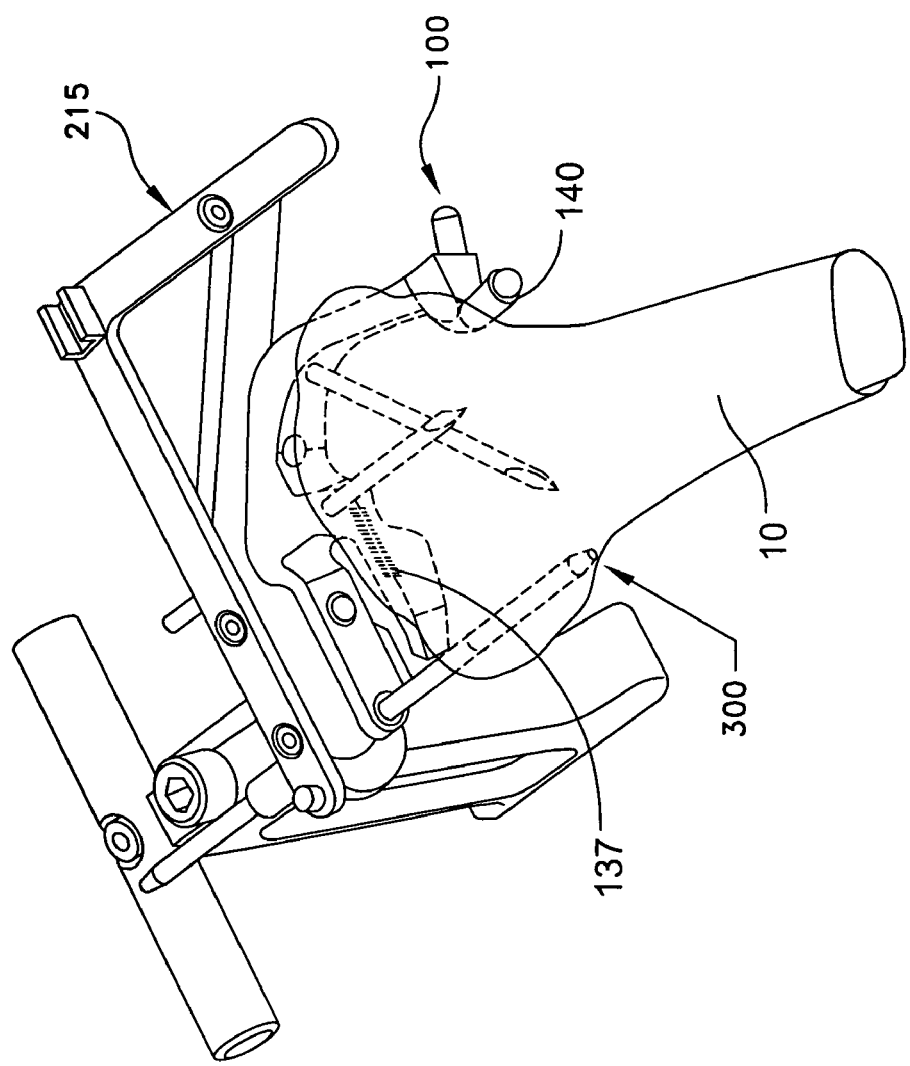

If desired, and looking now at FIGS. 11D, 11E and 11F, it is also possible to provide guide element 215 of slope guide 200 with an "L shape" configuration, rather than the "Z shape" configuration discussed above. Again, this construction provides several benefits. First, the "L shape" configuration permits guide element 215 to wrap around the perimeter of the tibia. Second, the "L shape" of guide element 215 also operates to indicate if the slope guide is not vertically aligned with the level of the fluoroscope. More particularly, if slope guide 200 is not vertically aligned with the level of the fluoroscope, the "L shape" of guide element 215 will appear as an "L shape" on the fluoroscope. However, if guide element 215 is vertically aligned with the level of the fluoroscope, then the guide element will appear as a straight line on the fluoroscope. Again, this vertical alignment is important, since it enables alignment of slope guide 200 (and hence positioning guide 100) with the medial condyle, i.e., with the A-P slope plane.

7. The assembly is then maneuvered so that the medial locating pin 140 (FIGS. 10, 11 and 16), preferably formed as a pin although it could also be formed as a tab, fin, etc., is located against the medial aspect 80 (FIG. 16) of the tibia. As further adjustments in position are made, medial locating pin 140 is held in contact with the medial aspect of the tibia, thereby ensuring proper alignment of the instrumentation. Medial locating pin 140 references the medial aspect of the tibia, thus setting the distance from the medial aspect of the tibia to the apex pin 300 (FIG. 10), as will hereinafter be discussed. This reference distance is used in conjunction with the sizing of the osteotomy implant 27 (FIG. 3) so as to ensure a proper tibial reconstruction, e.g., the distance from the medial aspect of the tibia to the center of apex pin 300 may correspond to the distance from the medial aspect of the implant to the vertex of the wedge angle of the implant.

In another form of the invention, the reference distance may be the distance from the medial aspect of the tibia to a neutral axis of rotation in the bony hinge, which could be estimated by calculation. In this case, the distance from the medial aspect of the tibia to the neutral axis of the bony hinge may correspond to the distance from the medial aspect of the implant to the vertex of the wedge angle of the implant.

Figure 10:
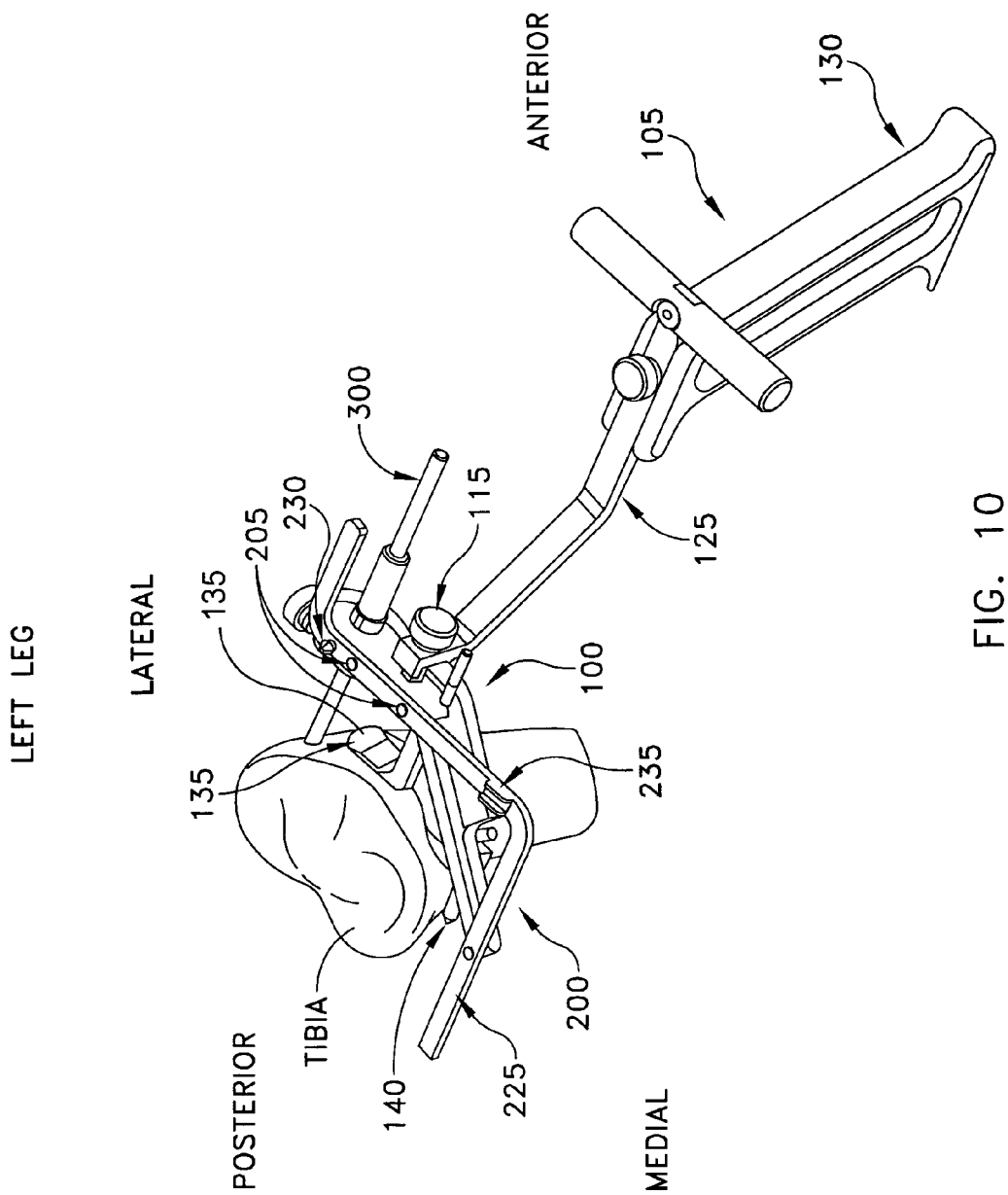
FIGS. 10-30 are schematic views showing a preferred method and apparatus for forming an appropriate osteotomy cut into the upper portion of the tibia, manipulating the tibia so as to open an appropriate wedge-like opening in the tibia, and then inserting an appropriate wedge-shaped implant into the wedge-like opening in the tibia.

8. The assembly is then rotated around the primary tibial anatomical axis, by sliding introducer handle 130 in a side-to-side motion, such that the instrumentation is aligned perpendicular to the frontal (coronal) plane, i.e., so that introducer 105 and apex pin 300 (see below) will extend parallel to the sagittal plane of the patient. To this end, slope guide 200 is provided with a ball 230 and a groove 235 alignment sight (FIG. 10). With the fluoroscope arranged so that it is set in the lateral mode, with the image being taken from the medial side at the level of the tibial plateau (see FIG. 11), the assembly is maneuvered until ball 230 is centered in groove 235 (FIG. 11). When this occurs, the system is aligned with the sagittal plane (i.e., positioning guide 100 is disposed so that apex pin 300 will extend perpendicular to the frontal plane, as will hereinafter be discussed).

9. Thus, when slope guide 200 is aligned with the medial condyle 75, and when ball 230 is aligned with groove 235, the system is aligned with (i) the A-P slope, and (ii) the sagittal plane. In other words, when slope guide 200 is aligned with medial condyle 75, and when ball 230 is aligned with groove 235, the instrumentation is positioned so that apex pin 300 (see below) is aligned with both the A-P slope and the sagittal plane, as will hereinafter be discussed.

10. With all of the previous adjustments established, the positions of (i) tibial tubercle locating tab 135, (ii) slope guide 200, (iii) medial locating pin 140, and (iv) the ball and groove sights 230, 235 are verified. With all positions confirmed, the frontal pin 145 (FIG. 16) and the antero-medial (A-M) pin 150 (FIG. 16) are inserted through positioning guide 100 and into the tibia. This secures positioning guide 100 to the tibia with the desired alignment.

Figure 14:
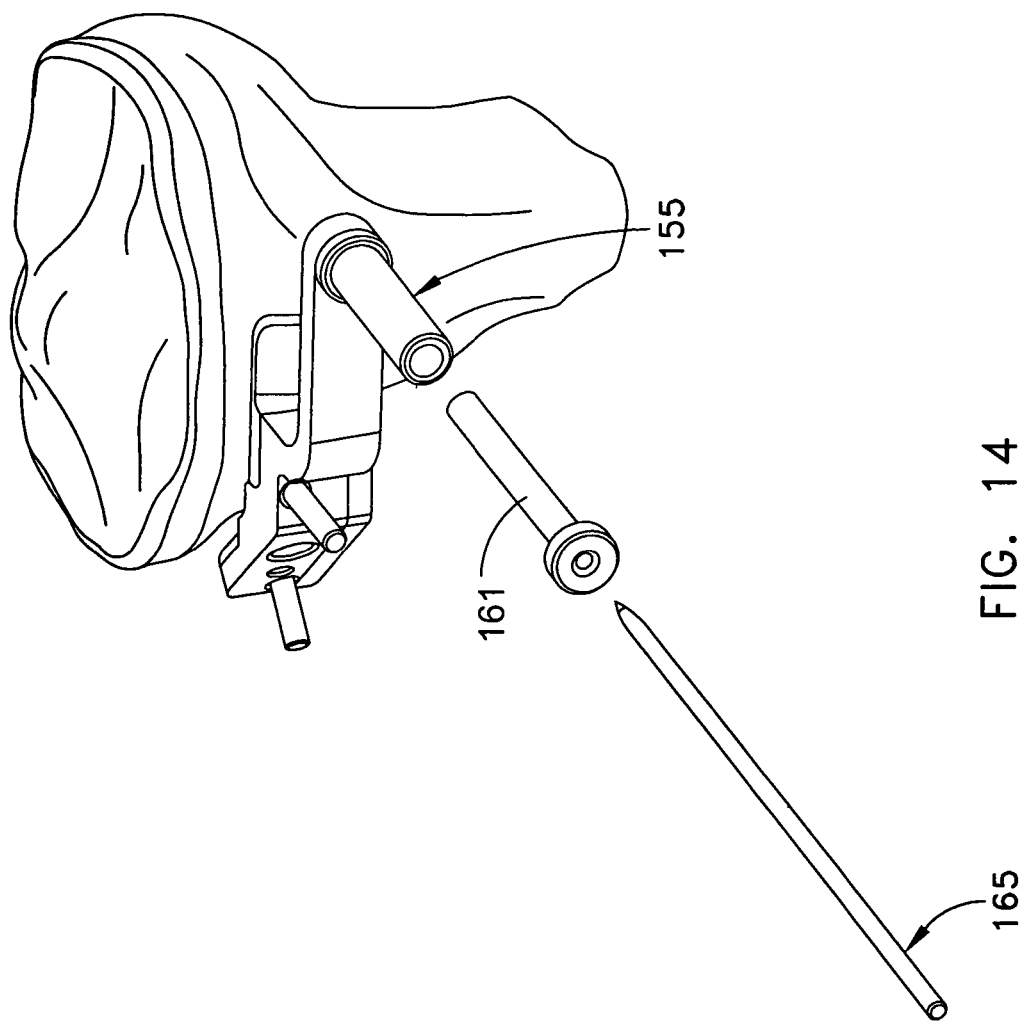

11. Next, apex pin 300 is inserted through positioning guide 100 and into the tibia. An apex aimer 155 (FIGS. 14 and 16) serves to guide apex pin 300 into the tibia with the proper orientation, i.e., so that apex pin 300 is positioned along the axis 70 which is located at the lateral limit of the intended osteotomy cut, with apex pin 300 extending parallel to the A-P slope and perpendicular to the coronal plane, and being coplanar with cutting plane 65. As a result, apex pin 300 can serve as the lateral stop for the osteotomy saw, whereby to clearly define the perimeter of the bony hinge, as will hereinafter be discussed. Apex pin 300 may be tapped or drilled into virgin bone, or it may be received in a pre-drilled hole (e.g., formed using apex aimer 155 and a standard surgical drill). An apex pin thumbscrew 160 (FIG. 16) may be used to secure apex pin 300 to positioning guide 100.

Apex pin 300 may be tapped or drilled into virgin bone, or it may be received in a pre-drilled hole (e.g., formed using apex aimer 155 and a standard surgical drill). A thumbscrew 160 (FIG. 16) may be used to secure apex pin 300 to positioning guide 100.

Figure 11G:
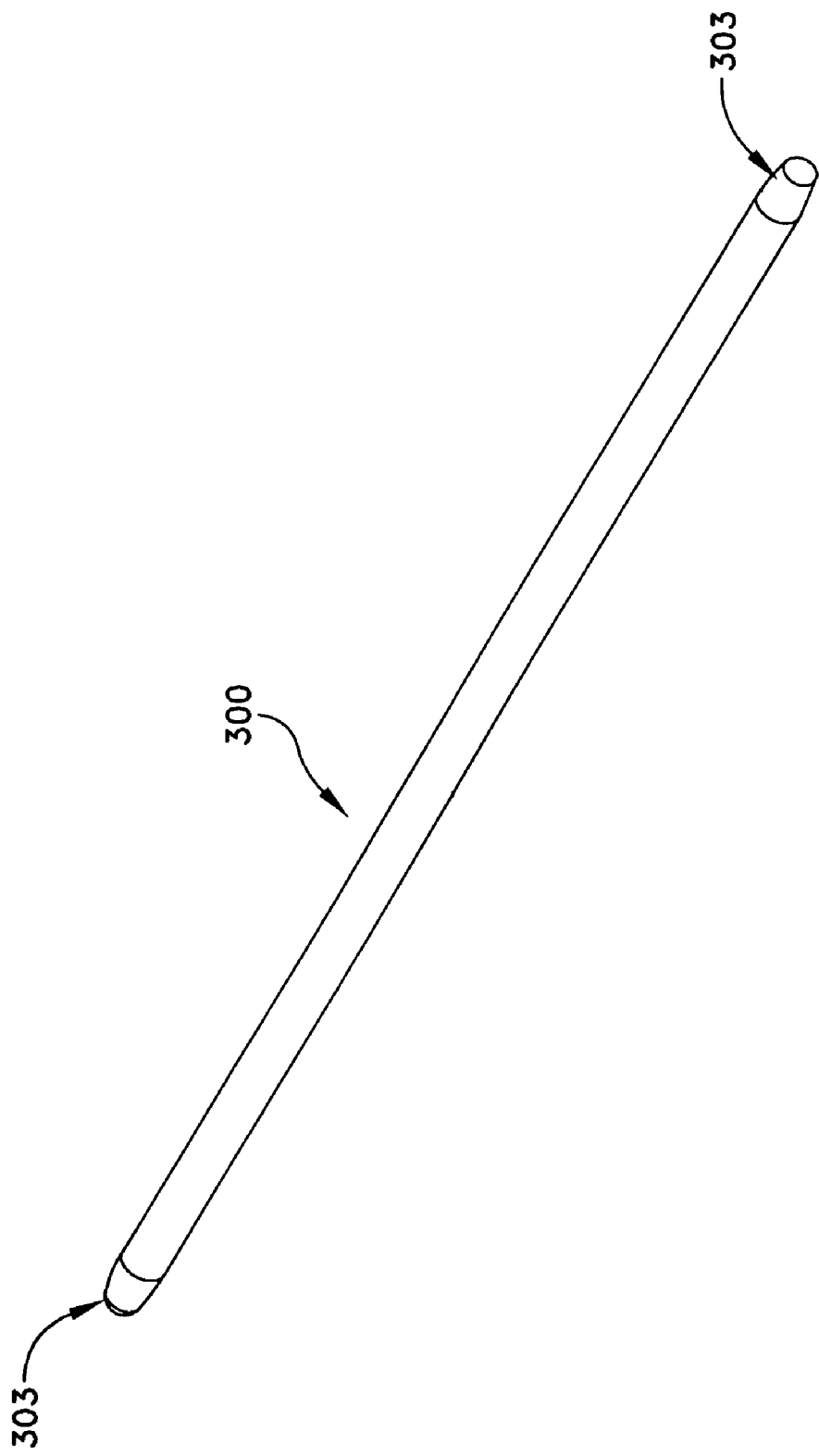

Apex pin 300 may be generally cylindrical in shape and, if desired, apex pin 300 may be provided with a rounded, or "bullet-shaped", nose 303, or other tapered end configuration, so as to facilitate deployment into the tibia (FIG. 11G).

Figure 12:
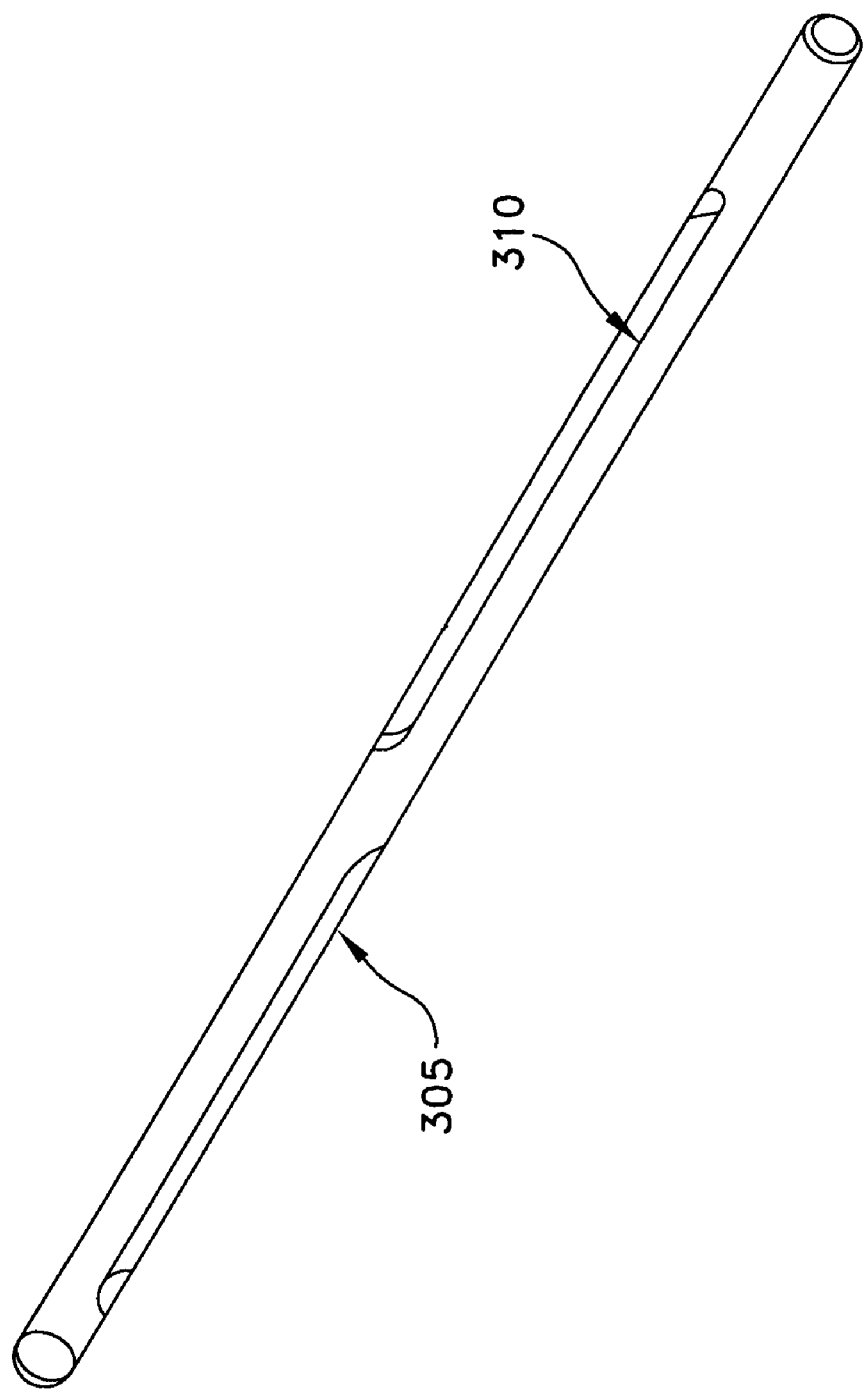
Figure 13:
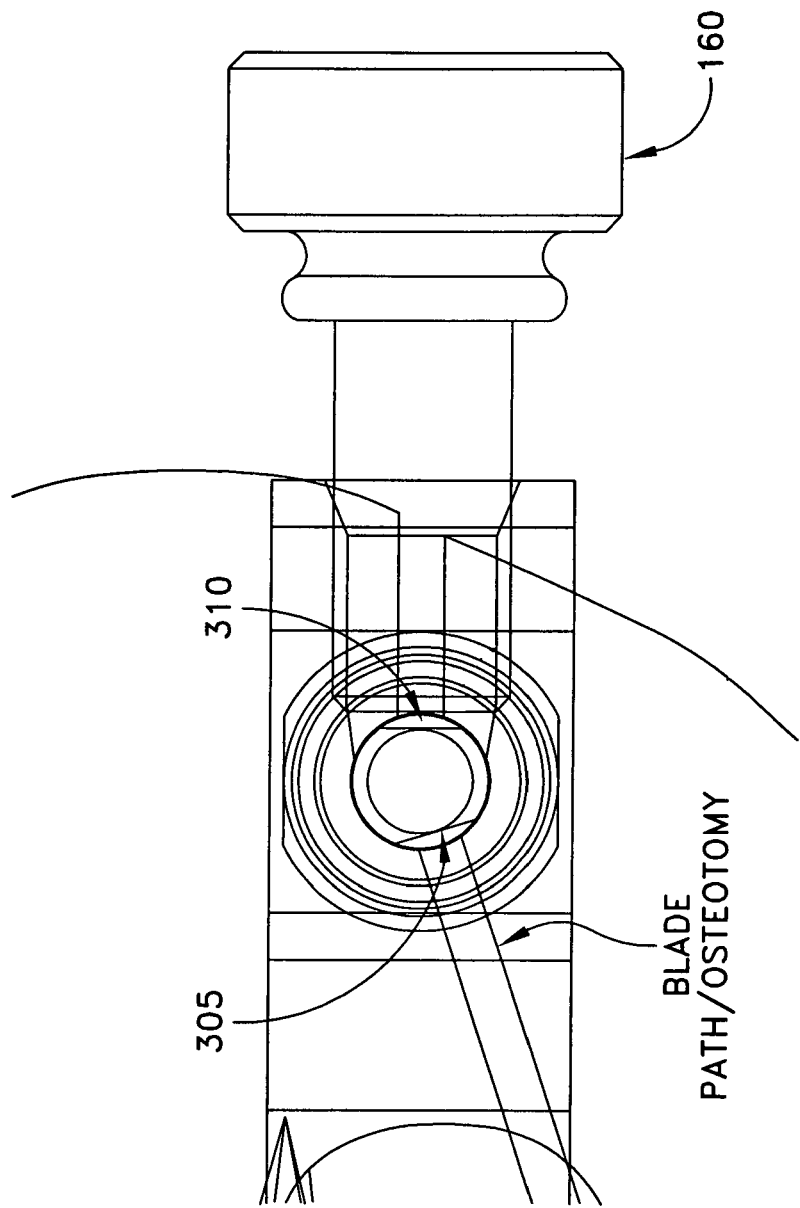

Furthermore, if desired, apex pin 300 may have a flat 305 (FIGS. 12 and 13) formed thereon to promote a complete cut-through of the osteotomy. Where apex pin 300 is provided with a distinct flat 305, it is preferably provided with a counterpart flat 310 (FIGS. 12 and 13), such that when apex pin 300 is positioned within the tibia and thumbscrew 160 is tightened against flat 310, the aforementioned flat 305 will be aligned with the osteotomy cut, whereby to ensure that the osteotomy blade cuts completely through the bone to reach the apex pin. See FIG. 13.

In another version of this construction (not shown), the flats 305, 310 may be diametrically opposed to one another, with thumbscrew 160 also being aligned with the osteotomy cut, whereby to make insertion of apex pin 300 less prone to error.

And in another embodiment of the present invention, apex pin 300 may be necked down to a smaller diameter in the area of the osteotomy. As a result of this construction, a slight relief area exists to accommodate the saw blade so as to help promote a complete cut-through, but does not require any specific orientation of the apex pin with respect to the osteotomy plane, as is the case where the apex pin is formed with distinct flats.

And in another version of the present invention, apex aimer 155 may be used with a guide sleeve 161 (FIG. 14) and a small-diameter guide pin 165 in order to first check the position of the small-diameter guide pin 165 relative to the desired axis for the apex pin, before thereafter deploying the larger-diameter apex pin 300. In this respect, it will be appreciated that repositioning a misdirected small-diameter guide pin 165 is easier and less traumatic to the host bone than repositioning a misdirected larger-diameter apex pin 300.

Figure 15:
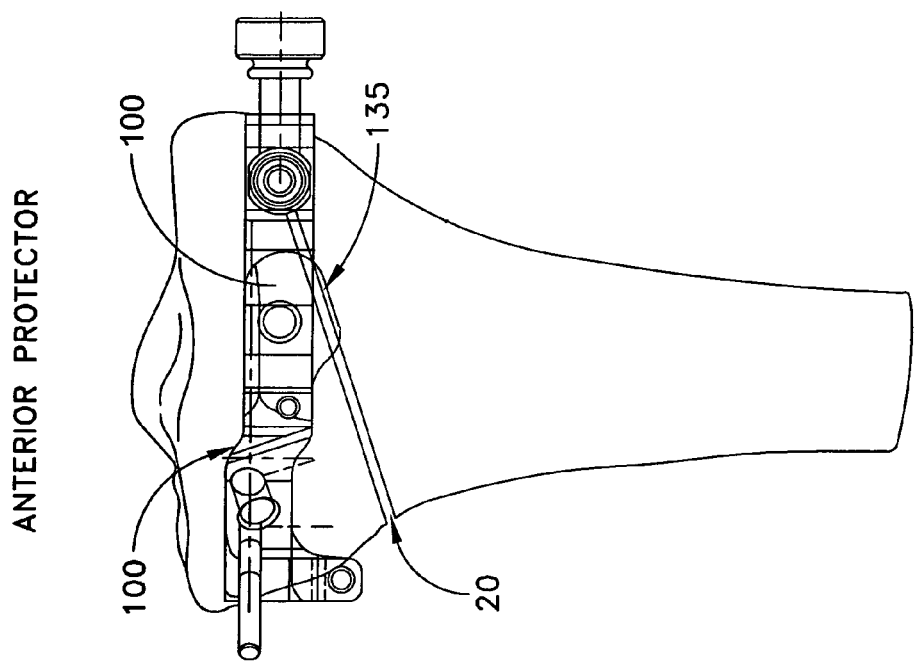

As seen in FIG. 15, tibial tubercle locating tab 135 is preferably sized so that it also functions as an anterior protector, by providing a protective shield between the oscillating saw blade (to be used later in the procedure to form the osteotomy cut 20) and the anterior soft tissue structures, e.g., the patellar tendon. Thus, tibial tubercle locating tab 135 also functions as a patellar tendon protector.

12. By virtue of the foregoing, it will be seen that apex pin 300 is positioned in the patient's tibia so that the apex pin extends (i) parallel to the A-P slope of the tibia, and (ii) parallel to the sagittal plane of the patient. As a result, when the osteotomy cut 20 is subsequently formed in the bone (see below) by cutting along the osteotomy cut plane until the apex pin is engaged by the bone saw, so that the perimeter of the bony hinge is defined by the location of the apex pin, the bony hinge will extend (i) parallel to the A-P slope of the tibia, and (ii) parallel to the sagittal plane of the patient. By ensuring that apex pin 300 is set in the aforementioned fashion, and hence ensuring that the bony hinge is so created, the final configuration of the tibia can be properly regulated when the bone cut is thereafter opened so as to form the open wedge osteotomy.

13. Once apex pin 300 has been properly positioned in the bone, slope guide 200 and introducer 105 are removed, leaving positioning guide 100 properly aligned on, and secured to, the tibia, with apex pin 300 extending parallel to the A-P slope and parallel to the sagittal plane of the patient. See FIG. 16.

Figure 17:
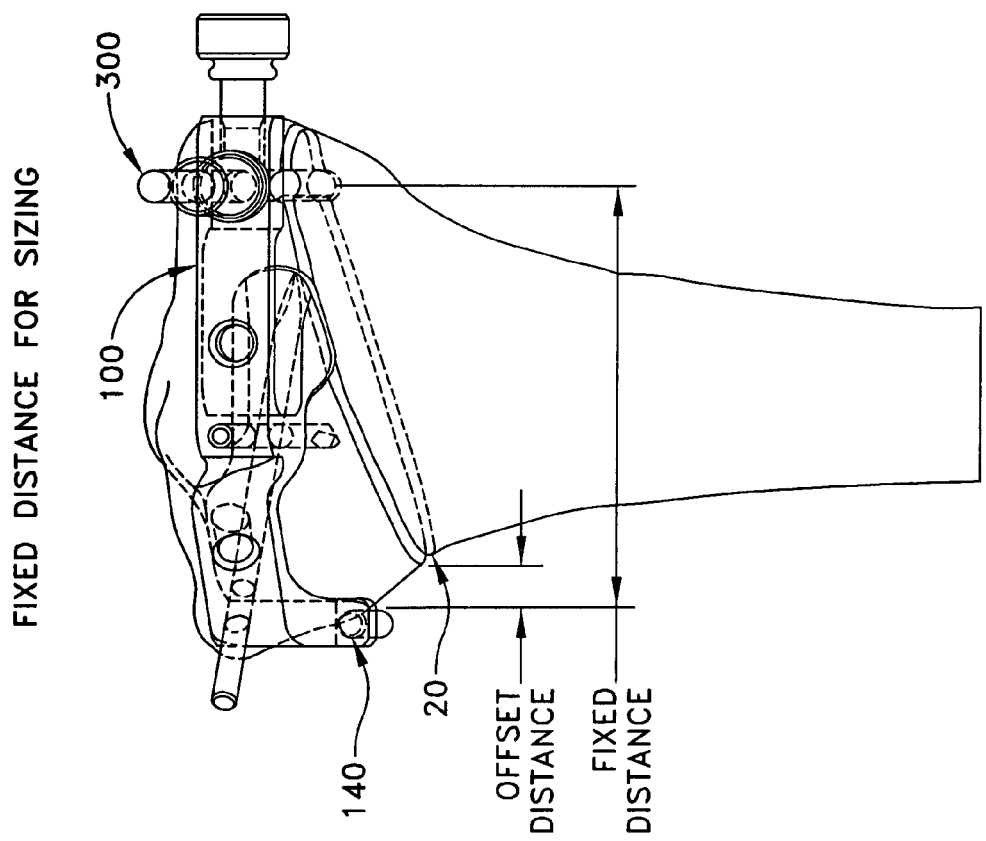

The size of positioning guide 100 and the associated instrumentation are used to prepare the osteotomy to fit a particular implant sizing of small, medium or large. More particularly, the medial locating pin 140, the size of positioning guide 100, and apex pin 300 all combine to implement an implant sizing scheme of small, medium or large. As seen in FIG. 17, medial locating pin 140, positioning guide 100 and apex pin 300 combine to provide a known, fixed distance from the medial aspect of the tibia to the apex pin. The size of the planned osteotomy is then set, allowing a specifically-sized implant (e.g., small, medium or large) to nominally fit between the medial aspect of the tibia and the apex pin.

In the embodiment shown in FIG. 17, there is a known lateral offset between medial locating pin 140 and the entry point of the osteotomy. The implant size is reduced slightly to factor in this offset distance so as to yield a proper fit.

Figure 17A:
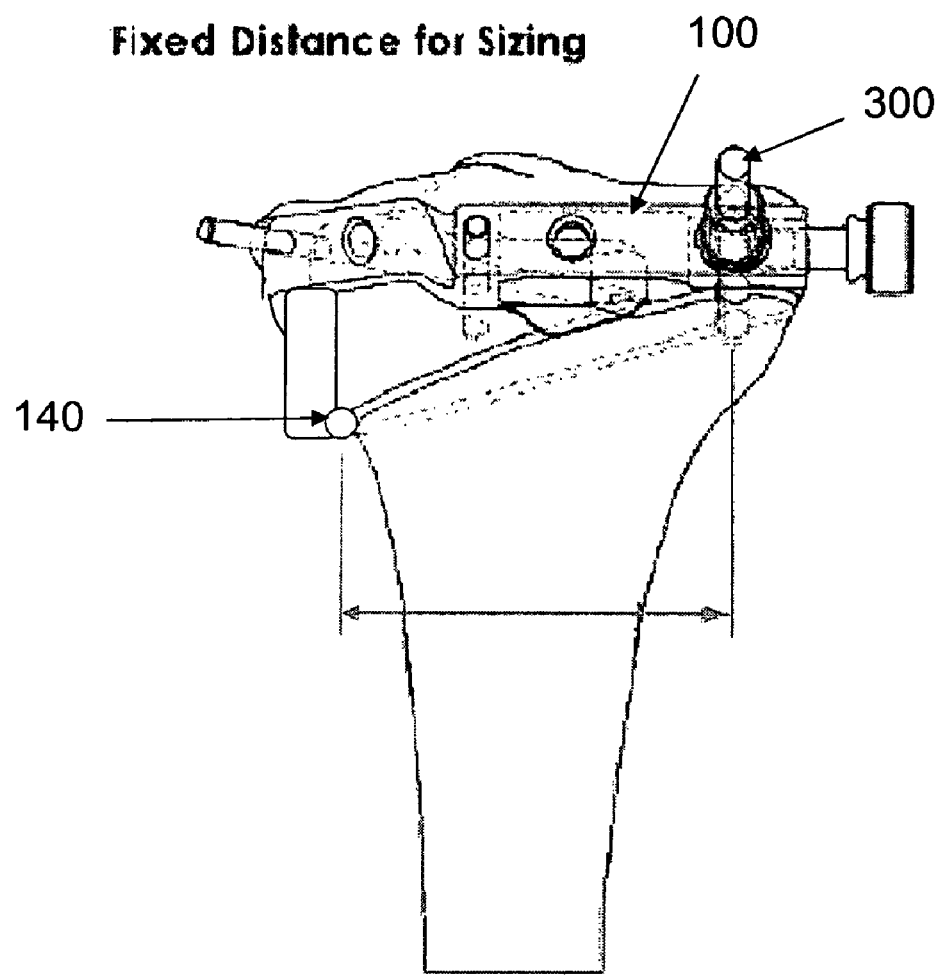

In a more preferred construction, and looking now at FIG. 17A, medial locating pin 140 is substantially aligned with the entry point of the planned osteotomy.

14. Looking next at FIG. 18, keyhole drill guide 400 is then attached to positioning guide 100 by passing keyhole drill guide 400 over frontal pin 145 and apex aimer 155. Keyhole drill guide 400 is then secured in this position with thumbscrew 405. At this point, a distal pin 410 is inserted through keyhole drill guide 400 and into the tibia. Distal pin 410 further secures the instrumentation to the tibia.

Next, a surface locator pin 415 is inserted through keyhole drill guide 400. Surface locator pin 415 slides through keyhole drill guide 400 until the distal tip of surface locator pin 415 contacts the surface of the tibia. For the purposes of the present invention, this surface may be referred to as the "antero-medial surface" or the "A-M surface", which is the anatomical surface of the tibia corresponding to the antero-medial approach of the osteotomy. When surface locator pin 415 contacts the A-M surface, the surface locator pin can act as an indicator as to the location of the A-M surface. This information can then be used to set the depth of the keyholes which are to be formed in the tibia (see below) for an improved implant fit.

Figure 29:
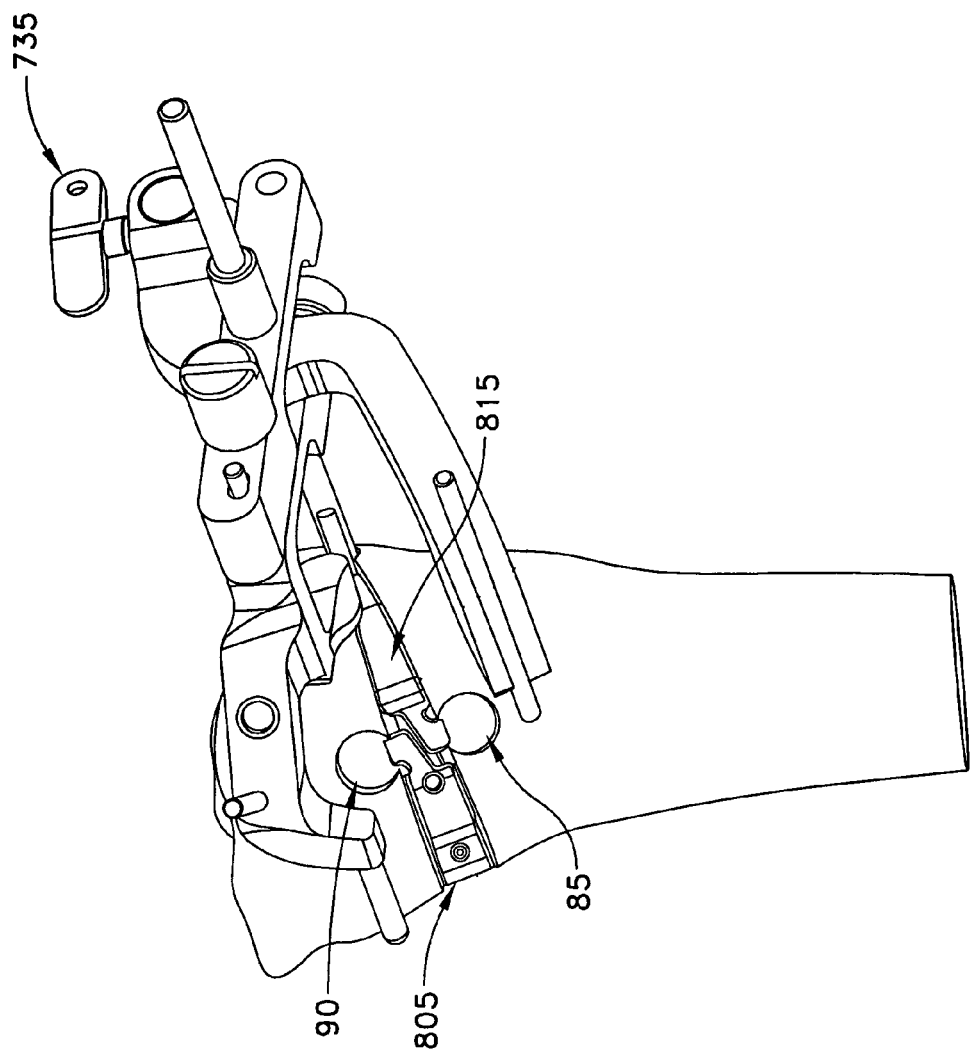

Next, an end mill 420 is inserted into the distal hole 425 (i.e., the bottom hole 425) of keyhole drill guide 400 and drilled until a stop flange 430 on end mill 420 contacts the proximal end of surface locator pin 415, whereby to form the distal keyhole 85 (FIG. 21) in the tibia. The drilling procedure is then repeated for the proximal hole 435 (i.e., the top hole 435), whereby to form the proximal keyhole 90 (FIG. 21) in the tibia. Thus, keyholes 85 and 90 are formed so that one keyhole (i.e., proximal keyhole 90) sits above the other keyhole (i.e., distal keyhole 85). While it is possible to drill the proximal keyhole before the distal keyhole, it is generally preferable to drill the distal keyhole first. This is because drilling the distal keyhole before the proximal keyhole reduces the possibility that the sloping nature of the bone will cause a later-drilled keyhole to slip into an earlier-drilled keyhole. It should be appreciated that keyhole drill guide 400 is configured so that distal hole 425 and proximal hole 435 will overlap the osteotomy cutting plane 65 to some extent (FIG. 21), so that when osteotomy cut 20 is thereafter formed and the tibia subsequently opened so as to create the wedge-like opening 25, distal keyhole 85 and proximal keyhole 90 will overlap, and communicate with, the wedge-like opening 25 (FIG. 29).

15. Once the two implant keyholes have been drilled into the tibia, end mill 420 is removed, thumbscrew 405 is loosened, and then keyhole drill guide 400 is removed.

Figure 19:
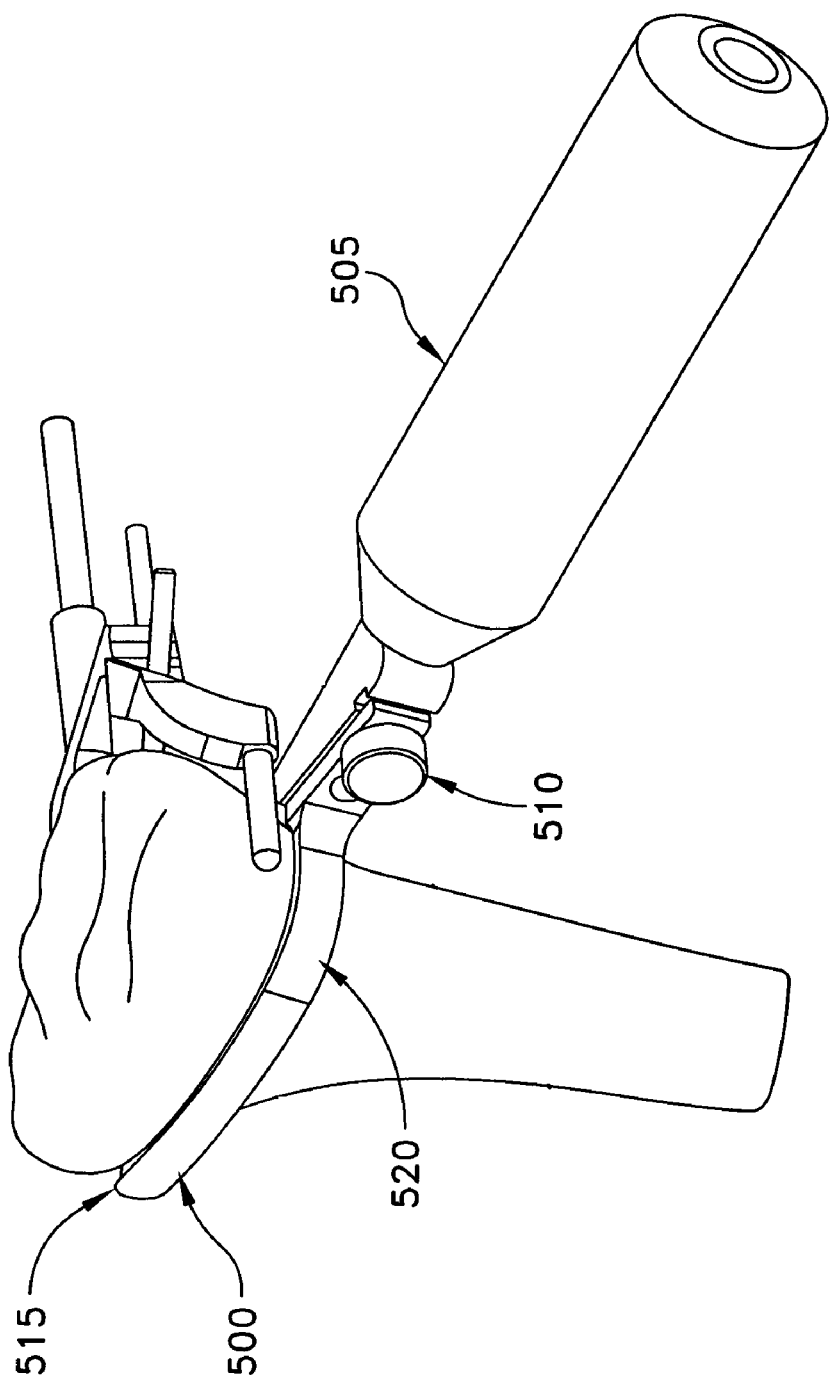
Figure 21:
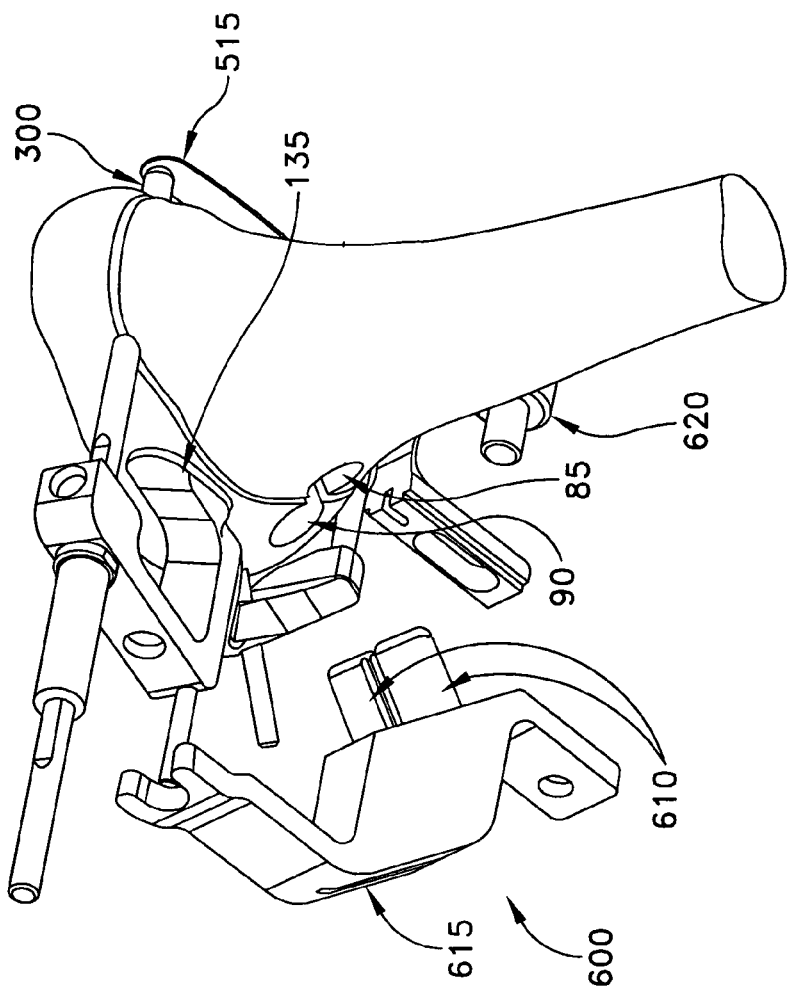

16. Next, and looking now at FIG. 19, posterior protector 500 is attached to an introducer 505 with a thumbscrew 510. Posterior protector 500 preferably comprises a far tip 515 and a curved portion 520. Far tip 515 is preferably formed out of a flexible material so as to facilitate passage of the posterior protector along the surface of the posterior cortex and beneath overlying soft tissue. Curved portion 520 comprises a relatively stiff material which provides support for far tip 515. Far tip 515 of posterior protector 500 is inserted into the incision and worked along the posterior cortex of the tibia until far tip 515 of posterior protector 500 substantially crosses the axis of, and in some cases actually engages, apex pin 300 (FIG. 21). Once posterior protector 500 has been properly deployed, the thumbscrew 510 is unscrewed, and introducer handle 505 is removed, leaving posterior protector 500 extending along the posterior cortex of the tibia, interposed between the tibia and the delicate neurological and vascular structures located at the back of the knee.

17. Looking next at FIG. 20, cutting guide 600 is then attached to positioning guide 100 and secured in place using cutting guide thumbscrew 605. Cutting guide 600 comprises alignment rods 610 (FIG. 21) that extend from the cutting guide into the pre-drilled keyholes 85, 90 (FIG. 21) to assist with cutting alignment. More particularly, alignment rods 610 ensure proper alignment between cutting guide 600, its cutting slot 615 (FIGS. 20 and 21) and the pre-drilled keyholes 85, 90 previously formed in the tibia with end mill 420 and, ultimately, ensure the desired fit between the implant and the tibia.

Figure 20:
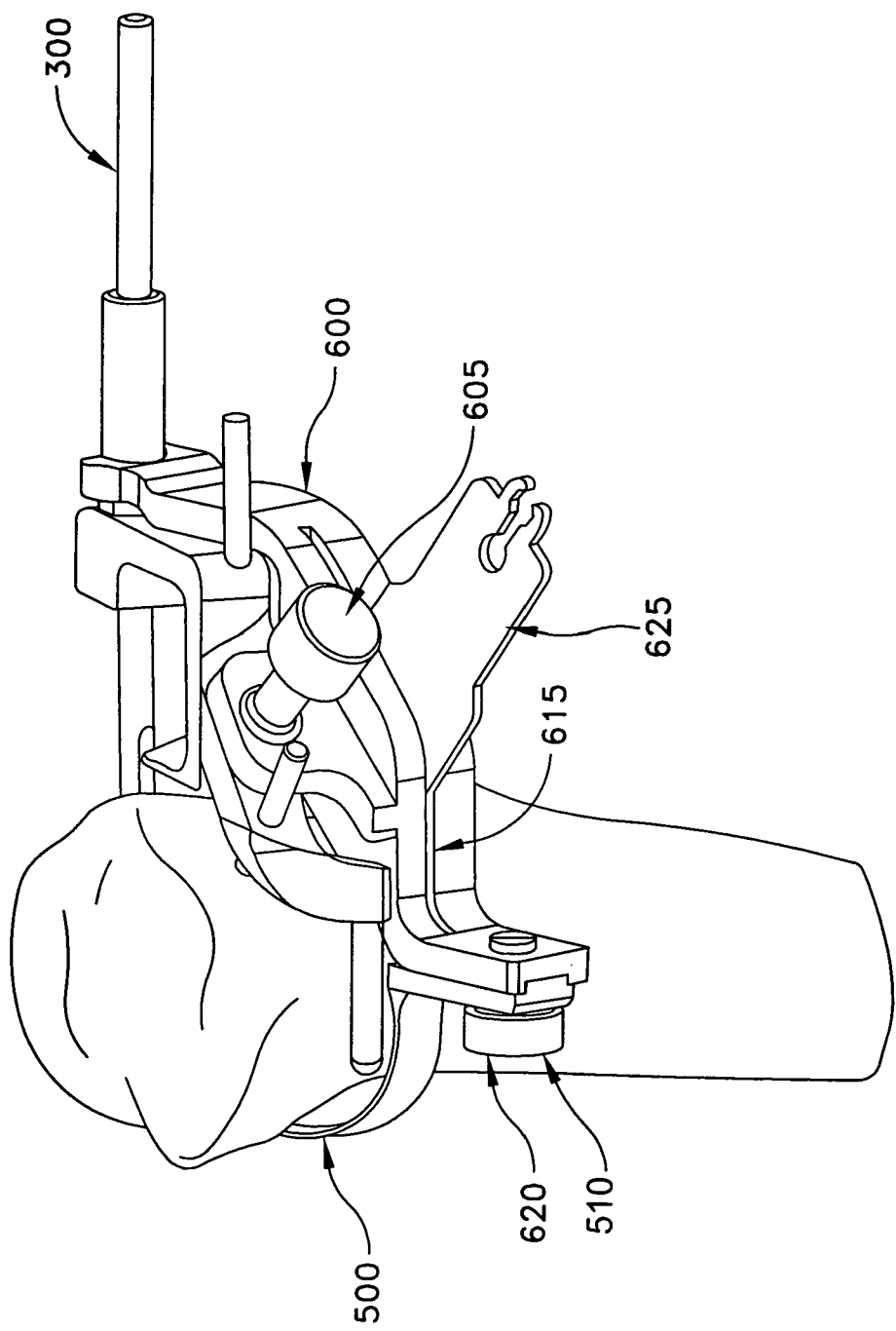

Then, posterior protector 500 is attached to cutting guide 600 using thumbscrew 620 (FIG. 20).

At this point, the instrumentation is ready to form the osteotomy cut, with cutting slot 615 of cutting guide 600 properly aligned with the osteotomy cut plane, apex pin 300 properly positioned at the far (lateral) limit of the osteotomy cut, tibial tubercle locating tab 135 forming a protective shield for the patellar tendon, and with posterior protector 500 forming a protective shield for the vascular and neurological structures at the back of the knee. In this respect it should be appreciated that cutting guide 600 is sized and shaped, and cutting slot 615 is positioned, so that, in addition to being aligned with the apex pin 300, the entry point of the cutting plane into the tibia is located at an appropriate location on the tibia's medial neck 66.

18. Next, a saw blade 625 (attached to an oscillating saw, not shown) is inserted into cutting slot 615 of cutting guide 600. The osteotomy cut is then made by plunging the oscillating saw blade through cutting slot 615 and into the bone (FIG. 20). The saw blade is used to cut completely through the medial and posterior cortices. The saw is operated until saw blade 625 contacts posterior protector 500 and apex pin 300. As the saw blade cuts through the tibia, it is constrained by cutting slot 615, apex pin 300 and posterior protector 500, so that the saw blade may only cut bone along the osteotomy plane, up to (but not beyond) the desired location of the bony hinge, and does not cut soft tissue. During cutting, tibial tubercle locating tab 135 also ensures that the saw blade will not inadvertently cut the patellar tendon.

After saw blade 625 forms the desired osteotomy cut 20 along the cutting plane, the saw blade is removed, and a hand osteotome (not shown) of the sort well know in the art is inserted through cutting slot 615 and into the osteotomy cut 20, and then the cut is completed through the posterior cortical bone near apex pin 300 and posterior protector 500. Then the hand osteotome is removed.

At this point the osteotomy cut 20 has been completed, with the osteotomy cut terminating on the lateral side at apex pin 300, so that the bony hinge is properly positioned at the desired location, i.e., parallel to the A-P slope and perpendicular to the coronal plane.

Next, thumbscrew 620 is loosened and posterior protector 500 removed. Then thumbscrew 605 is loosened and cutting guide 600 is removed.

At this point, the desired osteotomy cut 20 has been formed in the tibia, with keyholes 85 and 90 formed below and above, respectively, the osteotomy cut.

In order to complete the procedure, the bone must now be opened so as to reconfigure the tibia to the desired geometry, and then the tibia stabilized with the desired configuration, e.g., by inserting a wedge-shaped implant 27 into wedge-like opening 25.

19. Looking next at FIG. 22, opening jack 700 is assembled onto the instrumentation by receiving frontal pin 145 in a hole 705 formed in jack arm 710, by receiving apex aimer 155 in another hole 715 formed in jack arm 710 and jack arm 725, and by receiving distal pin 410 in a slot 720 formed in jack arm 725. Opening jack 700 is secured to positioning guide 100 with a thumbscrew 730.

Figure 23:
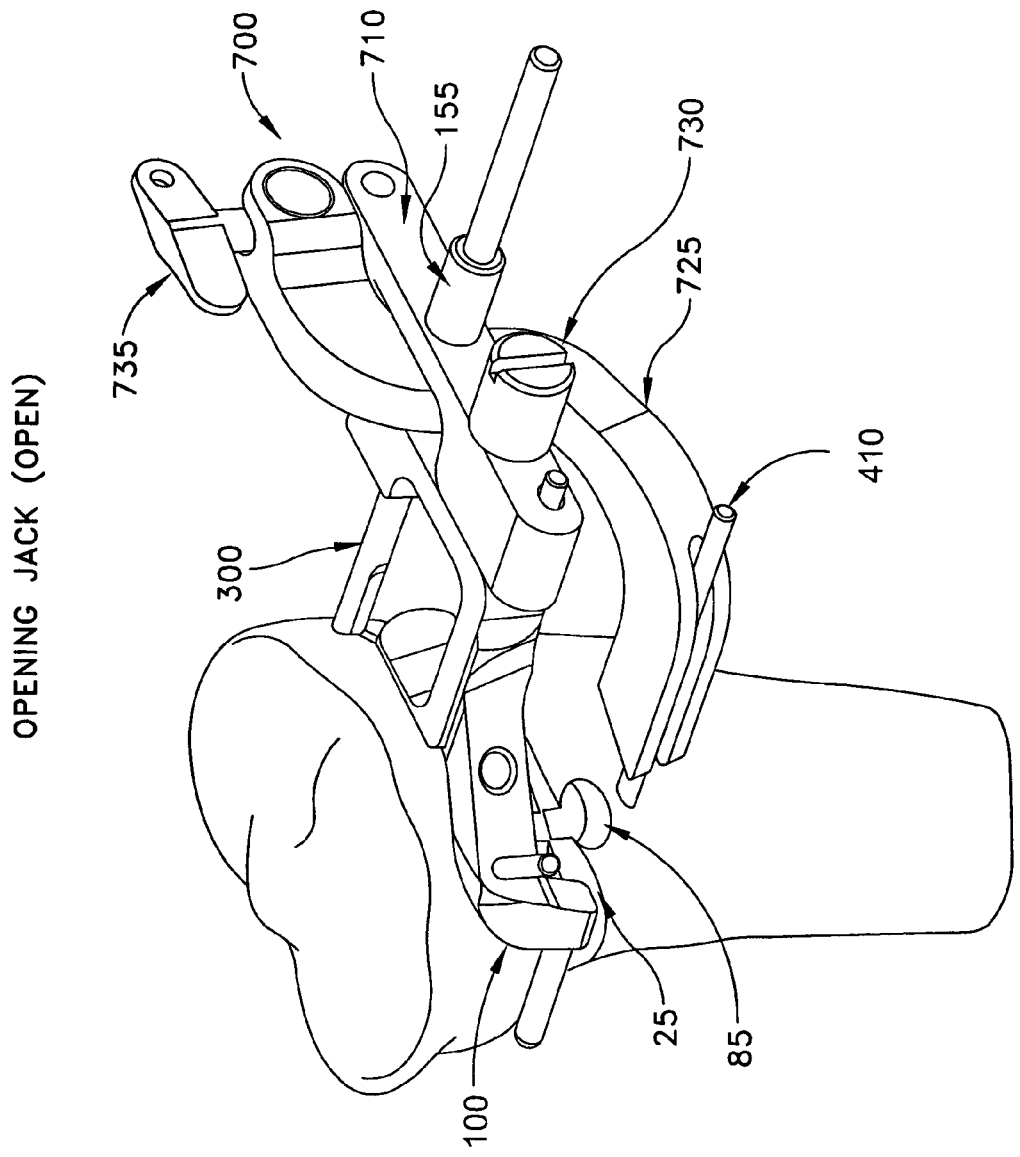
Figure 23A:
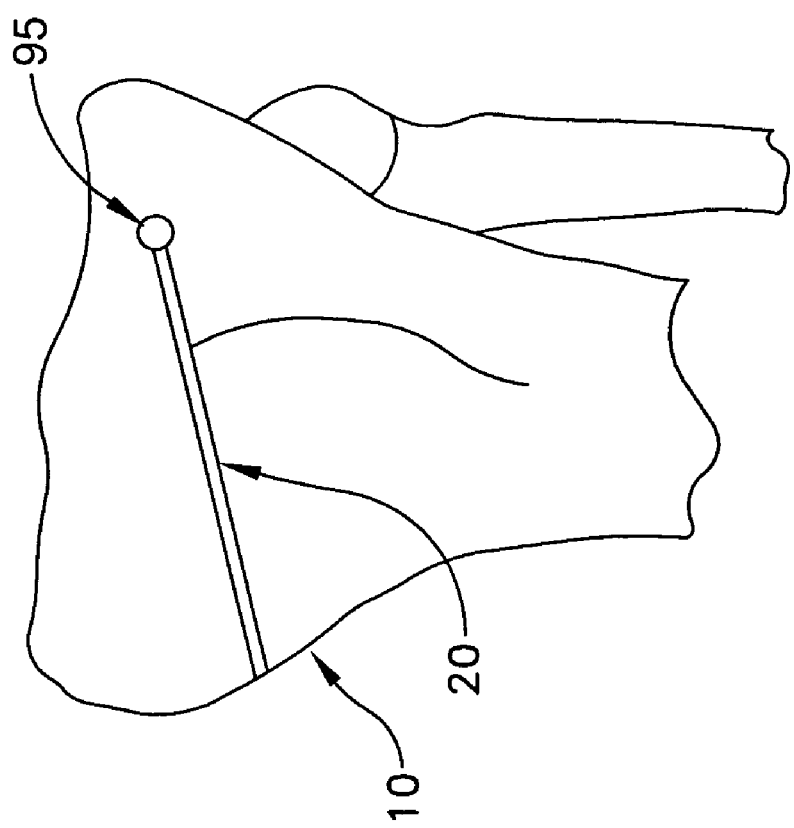

Once opening jack 700 is in place, the jack is opened by rotating jack screw 735. This causes jack arm 725 to pivot about apex aimer 155 so as to open the jack and thereby open the desired wedge-like opening 25 in the tibia. See FIG. 23. Preferably the patient's lower leg is manipulated as jack screw 735 is turned so as to assist in opening of the bone. As the wedge-like opening 25 is created in the bone, the tibia will be reoriented in a highly controlled manner, due to the fact that the bony hinge will be precisely positioned at axis 70 through the use of apex pin 300, i.e., the bony hinge will extend parallel to the A-P slope and parallel to the sagittal plane. Furthermore, as the wedge-like opening 25 is created in the bone, the risk of bone cracking will be minimized, due to the fact that apex pin 300 forms an oversized hole 95 (FIGS. 23A and 27) at the lateral end of the bone cut, i.e., "oversized" relative to the thickness of the osteotomy cut, whereby to reduce the occurrence of stress risers and the like as the bone is opened.

The surgeon uses opening jack 700 to open the bone to the extent necessary to correctly re-align the weight-bearing axis of the knee.

20. Then, with opening jack 700 still in place, an implant is positioned in the wedge-like opening 25.

If desired, the implant may be a "generic" implant such as the implant 27 shown in FIG. 3.

Figure 24:
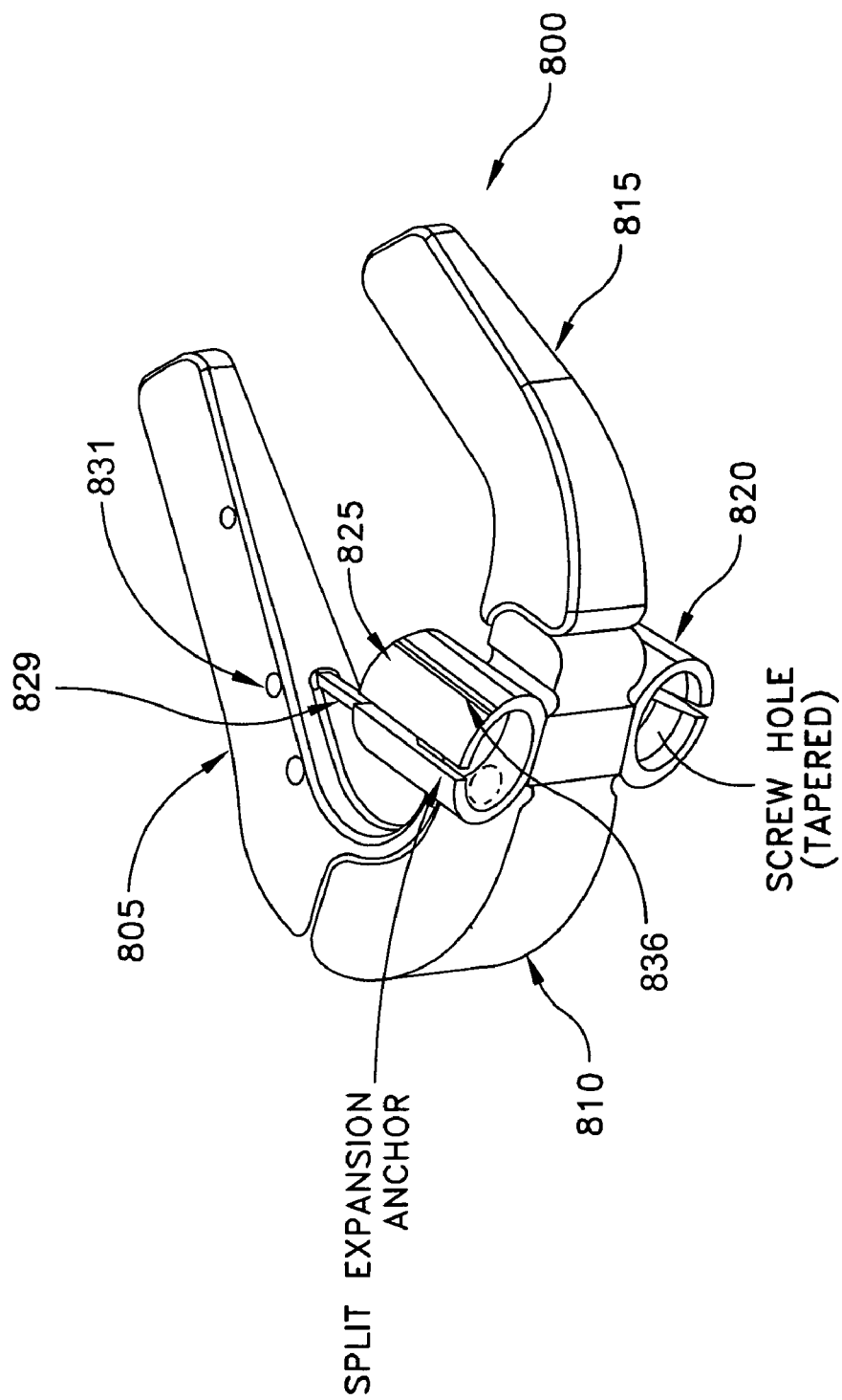

More preferably, however, and looking now at FIG. 24, there is shown a wedge-shaped implant 800 formed in accordance with the present invention. Wedge-shaped implant 800 is characterized by a wedge-like side profile configured to match the geometry of the wedge-like opening 25 (i.e., to match the prescribed correction angle of the open wedge, high tibial osteotomy). Preferably, wedge-shaped implant 800 is also formed so as to have a U-shaped top profile, such that it can form a barrier about the perimeter of the wedge-like opening 25, whereby to contain graft material (e.g., bone paste, bone cement, etc.) which may be positioned within the interior of the wedge-like opening 25. In one preferred form of the present invention, wedge-shaped implant 800 is formed so as to have an asymmetric configuration when viewed in a top view, so as to mate with the geometry of the tibia when the implant is positioned using an antero-medial approach. Wedge-shaped implant 800 is sized so as to match the known distance from the medial aspect of the tibia to the axis of the bony hinge, which is set by the position of apex pin 300. Wedge-shaped implant 800 may be formed out of absorbable material or non-absorbable material, as desired.

Figure 25:
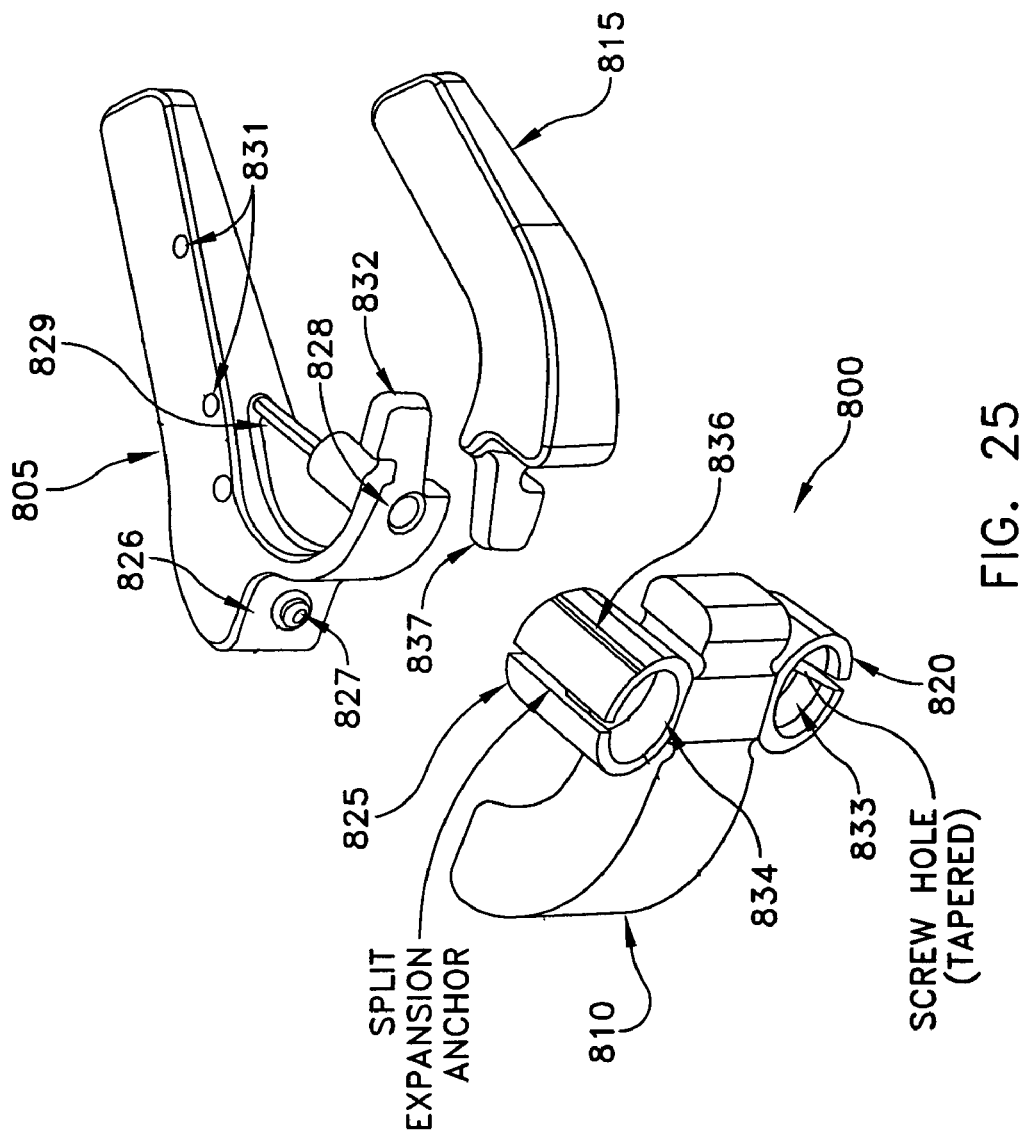
Figure 26:
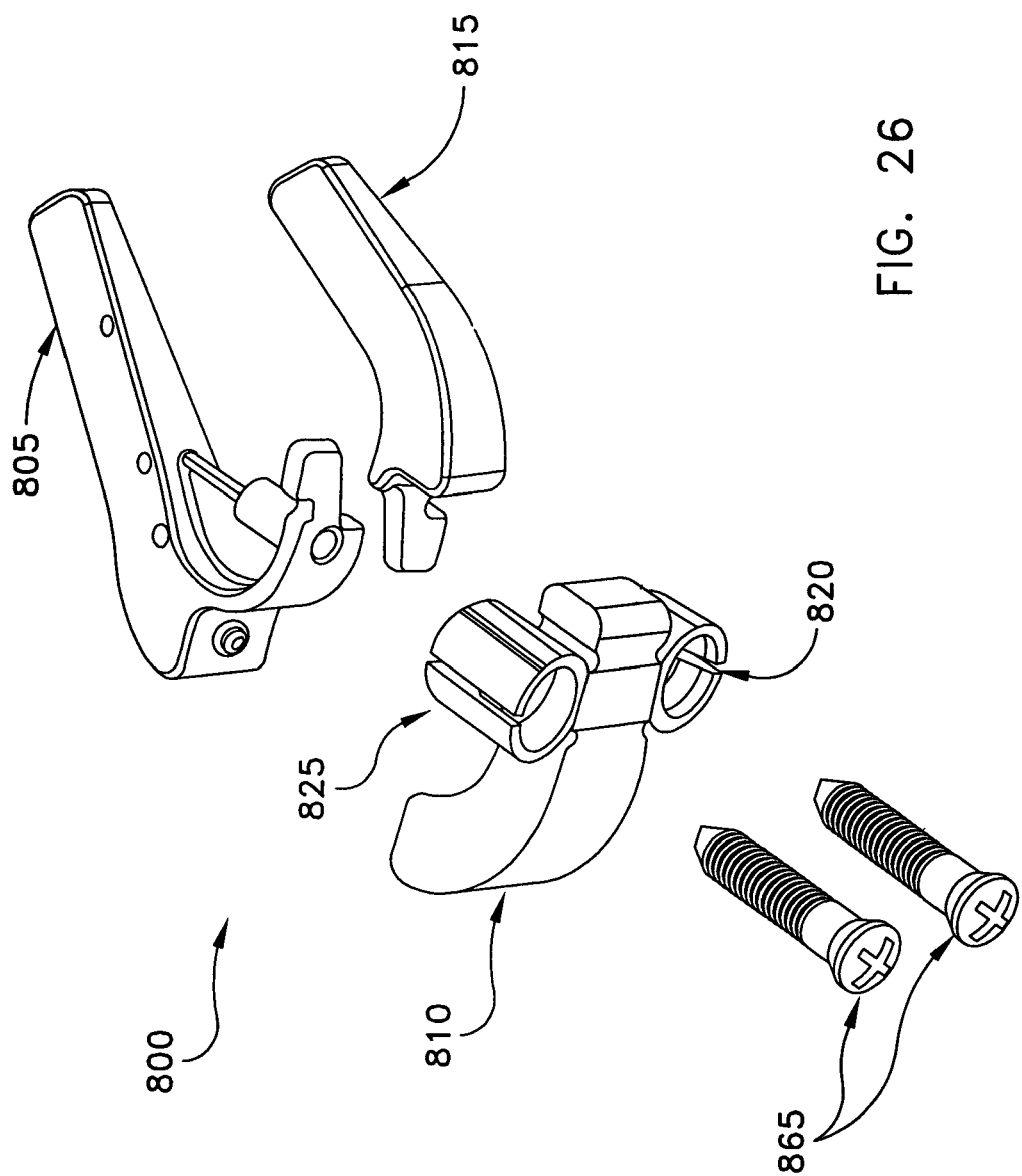

In one preferred form of the invention, and looking now at FIGS. 25 and 26, implant 800 preferably comprises a three-part assembly, comprising posterior graft containment arm (GCA) 805, a base 810 and an anterior graft containment arm (GCA) 815. The individual components of implant 800 may each be formed out of absorbable material and/or non-absorbable material, as desired. Furthermore, where one or more of the implant components is formed out of an absorbable material, the absorption characteristics of the material may vary as desired. By way of example but not limitation, base 810 may be formed out of a relatively slowly-absorbing material, while posterior graft containment arm (GCA) 805 and anterior graft containment arm (GCA) 815 may be formed out of a relatively faster-absorbing material. Base 810 preferably comprises a pair of keys 820, 825.

In one preferred form of the invention, implant 800 is formed so that posterior graft containment arm (GCA) 805 has a generally wedge-shaped profile including an engagement seat 826 comprising an alignment post 827, and an introducer screw hole 828 opening on the antero-medial side of the component for engagement with introducer 845 (see below). A strengthening rib 829 is preferably provided as shown. Additionally, raised points or dimples 831 may be provided to help fix posterior graft containment arm (GCA) 805 to the bone. An alignment tab 832 is provided for extension into upper keyhole 90 (FIG. 29) when posterior graft containment arm (GCA) 805 is positioned in the wedge-shaped opening 25.

And in one preferred form of the invention, base 805 is formed so that its keys 820, 825 each includes a bore 833, 834, respectively, with the keys being slotted longitudinally so as to permit expansion of the keys when fixation screws 865 are thereafter deployed in the bores, whereby to help lock the implant against the hard cortical bone of the tibia. External ribs 836 may be provided on the outer surfaces of keys 820, 825 so as to help fix keys 820, 825 in keyholes 85, 90, respectively, when keys 820, 825 are expanded, as will hereafter be discussed in further detail. External ribs 836 may extend longitudinally or circumferentially. Keys 820, 825 protrude from the upper and lower surfaces of base implant 810, and accommodate shear loads which may be imposed across the implant. Furthermore, expansion of keys 820, 825 creates an interference fit with the cortical bone of the tibia, and can help support tensile loads which may be imposed across the implant. An alignment mechanism (not shown) is provided for mating with alignment post 827 of posterior graft containment arm (GCA) 805.

The bores 833, 834 may be axially aligned with the longitudinal axes of keys 820, 825, respectively. Alternatively, the bores 833, 834 may be arranged so that they diverge from one another, downwardly and upwardly, respectively, so as to direct screws 865 deeper into the adjacent portions of the tibia.

Anterior graft containment arm (GCA) 815 also comprises a generally wedge-shaped profile, and an alignment tab 837 is provided for extension into lower keyhole 85 when GCA 815 is positioned in the wedge-shaped opening 25.

Implant 800 is preferably assembled in situ.

In some instances, it may be advantageous to use an implant trial base 830 (FIGS. 27 and 28) in the course of preparing the tibia to receive implant 800, and in order to confirm proper fit of implant 800 in its seat.

More particularly, a pre-assembled assembly comprising posterior graft containment arm (GCA) 805, an implant trial base 830 and two guide sleeves 835, 840 are first inserted into wedge-like opening 25 in the bone using an introducer 845. See FIGS. 27 and 28.

Figure 27:
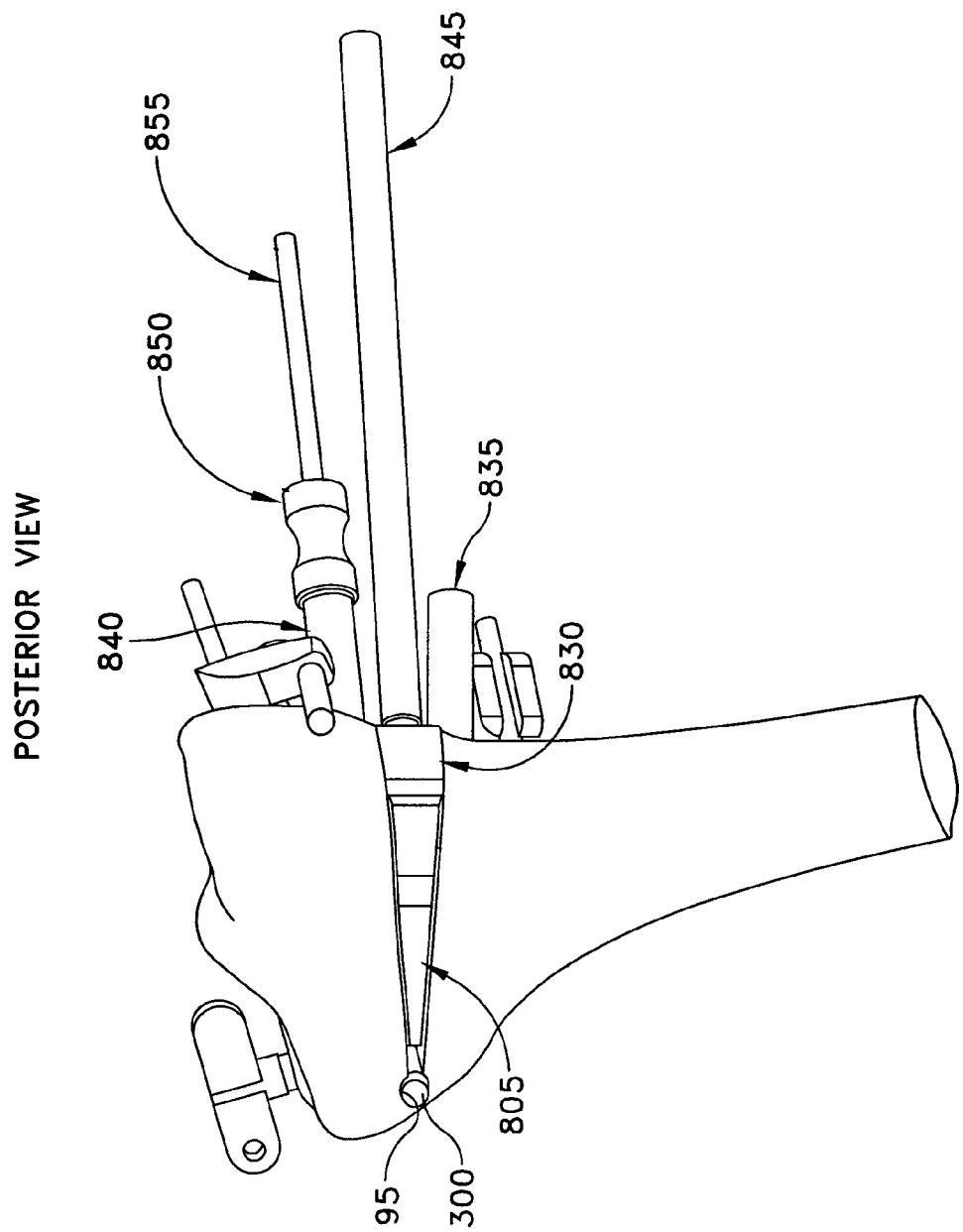
Figure 28:
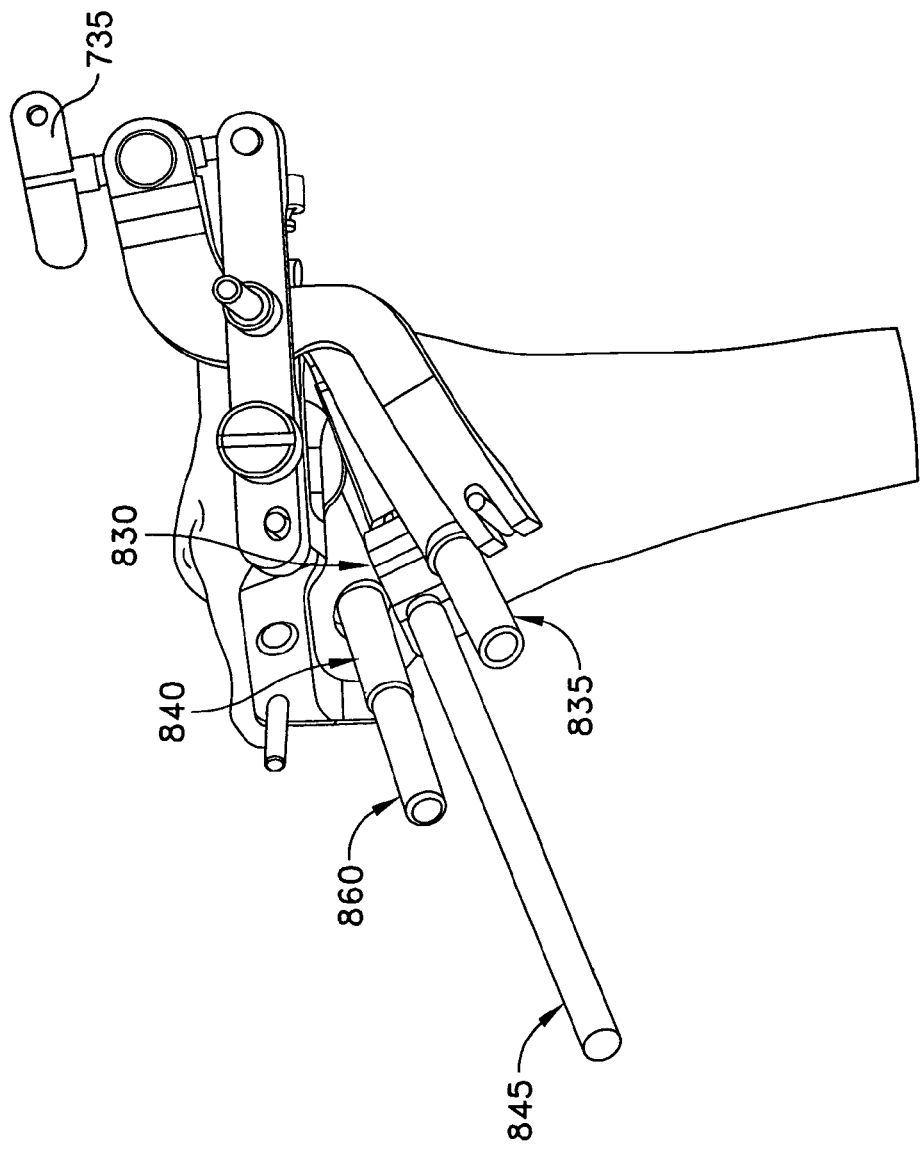

Next, a drill sleeve 850 and a drill 855 are inserted into guide sleeve 840 (FIG. 27). An upper hole is drilled into the tibia with the drill. The drilling procedure is then repeated for guide sleeve 835 so as to create a lower hole. Then drill sleeve 850 and drill 855 are removed from the surgical site. Next, a tap 860 is inserted into guide sleeve 840 and the upper hole is tapped. See FIG. 28. Then the tap is inserted into guide sleeve 835 and the lower hole is tapped. Then tap 860 is removed from the surgical site.

21. Next, posterior graft containment arm (GCA) 805 is released from introducer 845, and then introducer 845 and implant trial base 830 are removed. Posterior graft containment arm (GCA) 805 remains in wedge-like opening 25.

22. Then, if desired, graft material is packed into the osteotomy opening.

23. Next, anterior graft containment arm (GCA) 815 is placed into the osteotomy opening and aligned with the prepared implant holes. See FIG. 29. If necessary, jack screw 735 is rotated as needed so as to facilitate insertion of anterior GCA 815. At this point in the procedure, posterior graft containment arm (GCA) 805 and anterior graft containment arm (GCA) 815 are positioned in wedge-like opening 25.

Figure 30:
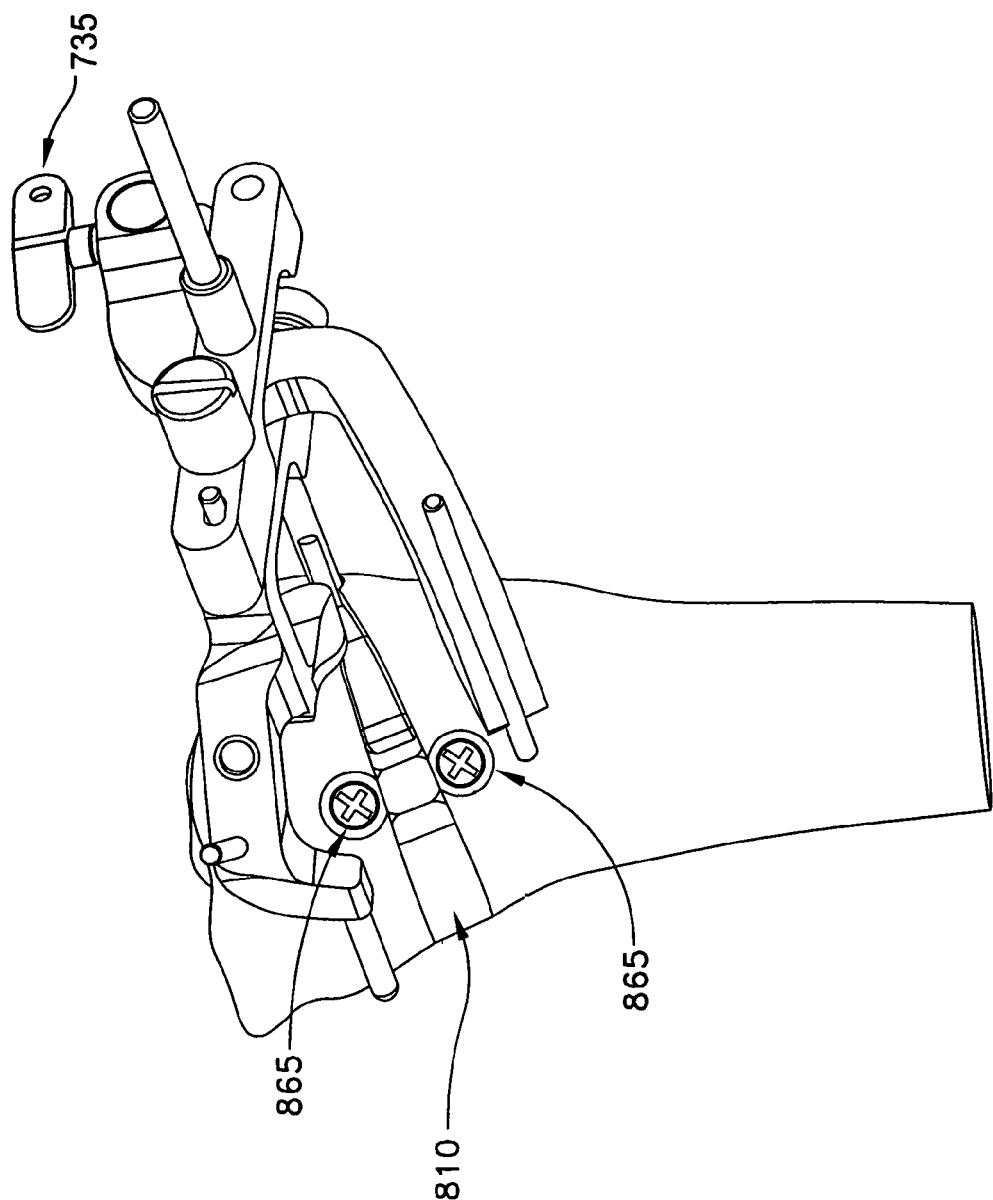

24. Then implant base 810 is inserted into the prepared osteotomy, with keys 820 and 825 seated in tibial holes 85 and 90, respectively, and with base 810 capturing posterior graft containment arm (GCA) 805 and anterior graft containment arm (GCA) 815 against the bony hinge. Keys 820 and 825, seating in keyholes 85 and 90, help ensure a precise fit of the implant to the bone. As this is done, jack screw 735 is adjusted as necessary so as to facilitate insertion of the base into the osteotomy. Then jack screw 735 is tightened slightly so as to ensure that the implant components are fully seated into the osteotomy wedge, with at least implant base 810, and preferably also posterior graft containment arm (GCA) 805 and anterior graft containment arm (GCA) 815, providing load bearing support to the tibia. Next, fixation screws 865 are inserted through keys 820 and 825 in base 810 and into the tapped holes in the tibia, and then tightened into place. As this occurs, fixation screws 865 expand keys 820, 825 so as to lock keys 820, 825 to the adjacent cortical bone, and fixation screws 865 extend into the tibia, so as to further lock the implant in position. See FIG. 30. Finally, opening jack 700, positioning guide 100, apex pin 300, distal pin 410, frontal pin 145 and A-M pin 150 are removed from the surgical site, and the incision closed.

Providing implant 800 with two graft containment arms, e.g., posterior graft containment arm (GCA) 805 and anterior graft containment arm (GCA) 815, is frequently preferred. However, in some circumstances, it may be desirable to omit one or both of posterior graft containment arm (GCA) 805 and anterior graft containment arm (GCA) 815. Thus, in one preferred form of the invention, implant 800 comprises only base 810 and omits both posterior graft containment arm (GCA) 805 and anterior graft containment arm (GCA) 815.

Providing implant 800 with a pair of keys 820, 825 is generally preferred. However, in some circumstances, it may be desirable to omit one or the other of keys 820, 825. Furthermore, in other circumstances, it may be desirable to provide more than two keys, e.g., to provide three keys.

Furthermore, each of the keys 820, 825 may include more than one bore 833, 834. Thus, for example, a key may include two bores, one angled leftwardly so as to direct a fixation screw leftwardly into the tibia to the left of the key, and/or one angled rightwardly so as to direct a fixation screw rightwardly into the tibia to the right of the key.

The use of apex pin 300 is significant for a number of reasons:

(1) the oversized, circular diameter hole 95 formed in the tibia by apex pin 300, which forms the limit of bone cut 20, effectively displaces the stress forces created at the edge of the bony hinge when the cut is opened to form the wedge-like opening 25, thereby adding significantly to the effective strength of the bony hinge;

(2) by using apex pin 300 to control the length of bone cut 20 (as measured from the medial aspect of the tibia to the apex pin), the seat for the implant is always of known size, thereby simplifying proper fitting of the implant to its seat in the bone, and also reducing the inventory of different-sized implants which must be on hand during the surgery;

(3) with apex pin 300 in place, bone resecting tools can be used with increased confidence, without fear of inadvertently cutting into, or even through, the bony hinge; and (4) since apex pin 300 controls the depth of bone cut 20, the implant can be reliably manufactured to appropriately address the required degree of correction needed to effect knee realignment (e.g., a 4 degree implant slope will always provide a 4 degree angle of correction).

Furthermore, the provision of (i) apex pin 300, posterior protector 500 and tibial tubercle locating tab 135 creates a "protection zone", and (ii) cutting guide 600 creates a closely constrained cutting path for saw blade 625, thereby together ensuring that only the desired portion of the bone is cut. Among other things, the provision of posterior protector 500 ensures that the delicate neurological and vascular tissues at the back of the knee are protected during cutting of the tibia.

The provision of keyholes 85, 90 in the tibia, and the provision of keys 820, 825 in the implant, is significant inasmuch as they provide improved stabilization of the implant, particularly against rotational and shearing forces. This is particularly true inasmuch as keyholes 85, 90 extend through the hard cortical bone at the periphery of the tibia.

Additional Constructions

Figure 31:
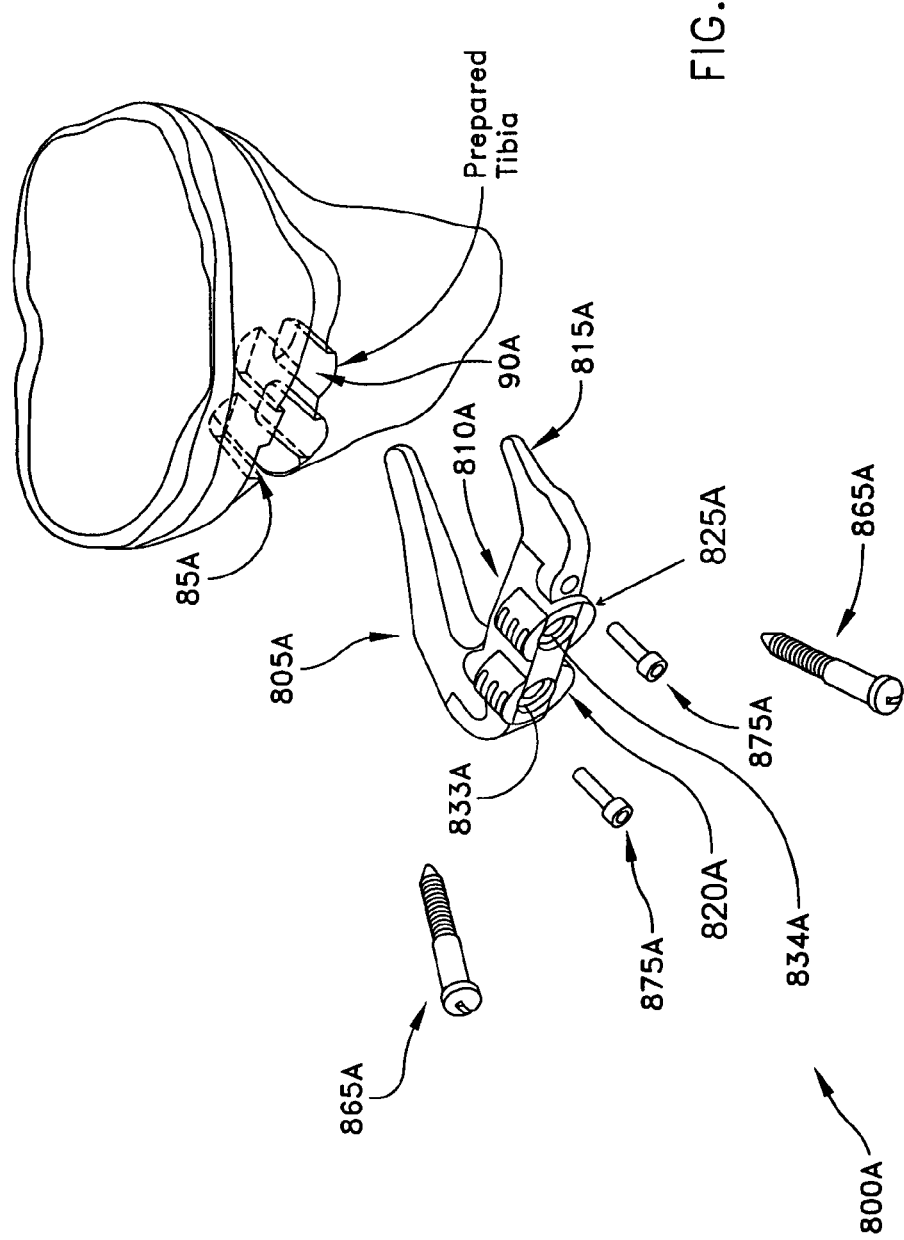
FIGS. 31-33 are schematic views showing an alternative wedge-shaped implant also formed in accordance with the present invention.
Figure 32:
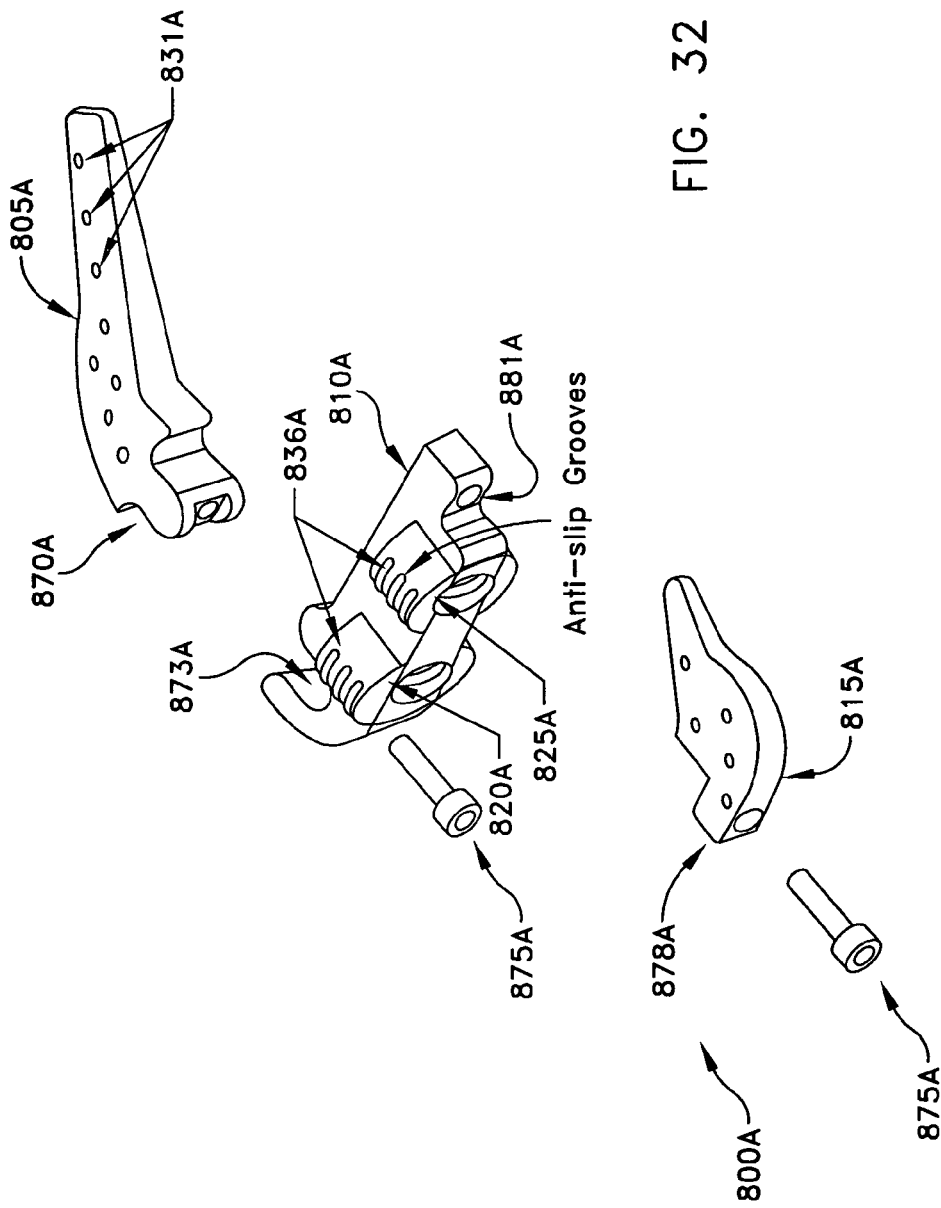
Figure 33:
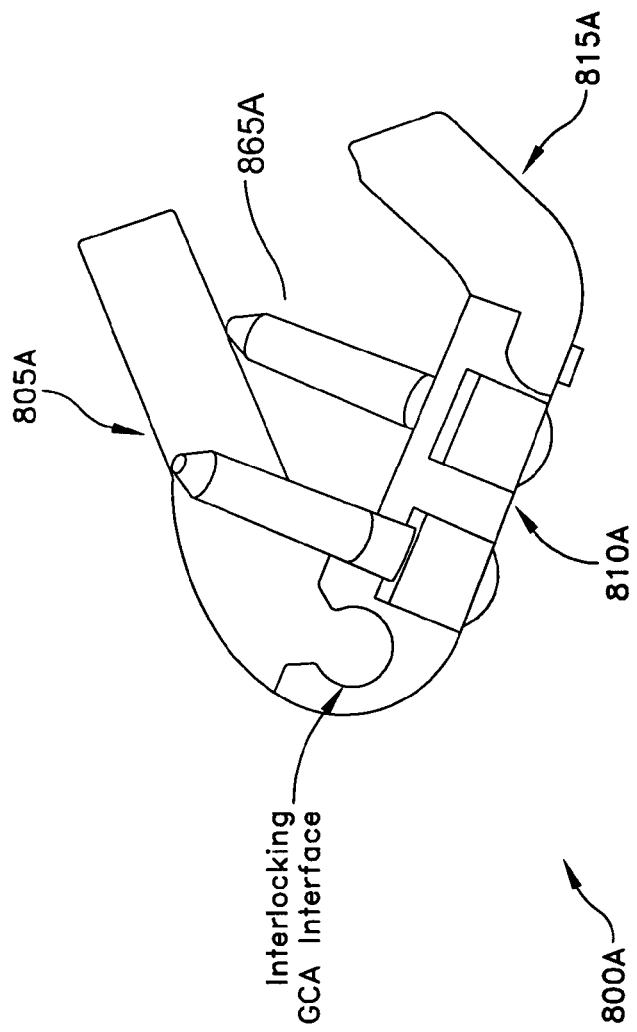

Looking next at FIGS. 31-33, there is shown an implant 800A also formed in accordance with the present invention. Implant 800A is generally similar to the implant 800 disclosed above, except that implant 800A has its keys disposed in a "side-by-side" disposition, rather than the "over-under" disposition of implant 800, as will hereinafter be discussed in further detail. Furthermore, implant 800A also provides an alternative approach for joining the posterior graft containment arm (GCA) to the base, and an alternative approach for joining the anterior graft containment arm (GCA) to the base, as will hereinafter also be discussed in further detail.

More particularly, and still looking now at FIGS. 31-33, implant 800A comprises a posterior graft containment arm (GCA) 805A, a base 810A and an anterior graft containment arm (GCA) 815A. Base 810A preferably comprises a pair of keys 820A, 825A. Keys 820A, 825A are laterally displaced along the width of base 810A, in a "side-by-side" configuration. This is in contrast to the construction of implant 800, which uses an "over-under" configuration for its keys 820, 825 (FIG. 24). Among other things, it has been found that the "side-by-side" configuration provides, at the base of the implant, excellent load-bearing characteristics and substantial resistance to rotational and shear forces.

Posterior graft containment arm (GCA) 805A includes a tab 870A, and base 810A includes a groove 873A, whereby posterior graft containment arm (GCA) 805A can mate with base 810A. A screw 875A is used to secure tab 870A in groove 873A, and hence posterior graft containment arm (GCA) 805 to base 810. Anterior graft containment arm (GCA) 815A includes a flange 878A, and implant base 810A includes a recess 881A, whereby anterior graft containment arm (GCA) 815A can mate with base 810A. Another screw 875A is used to secure flange 878A in recess 881A, and hence anterior graft containment arm (GCA) 815 to base 810.

Posterior graft containment arm (GCA) 805A, and/or anterior graft containment arm (GCA) 815A, may include raised points or dimples 831A.

Keys 820A, 825A each include a bore 833A, 834A, respectively. Bores 833A, 834A receive fixation screws 865A for fixing implant 800A to the tibia. Bores 833A, 834A preferably diverge from the longitudinal axes of keys 820A, 825A, respectively, so as to direct fixation screws 865A downwardly or upwardly into the adjacent portions of the tibia. Keys 820A, 825A may also include external ribs 836A. External ribs 836A may extend longitudinally or circumferentially. Keys 820A, 825A may also be slotted (i.e., in a manner analogous to the slots provided in keys 820, 825 of implant 800), whereby to permit keys 820A, 825A to expand when fixation screws 865A are received in bores 833A, 834A.

Figure 34:
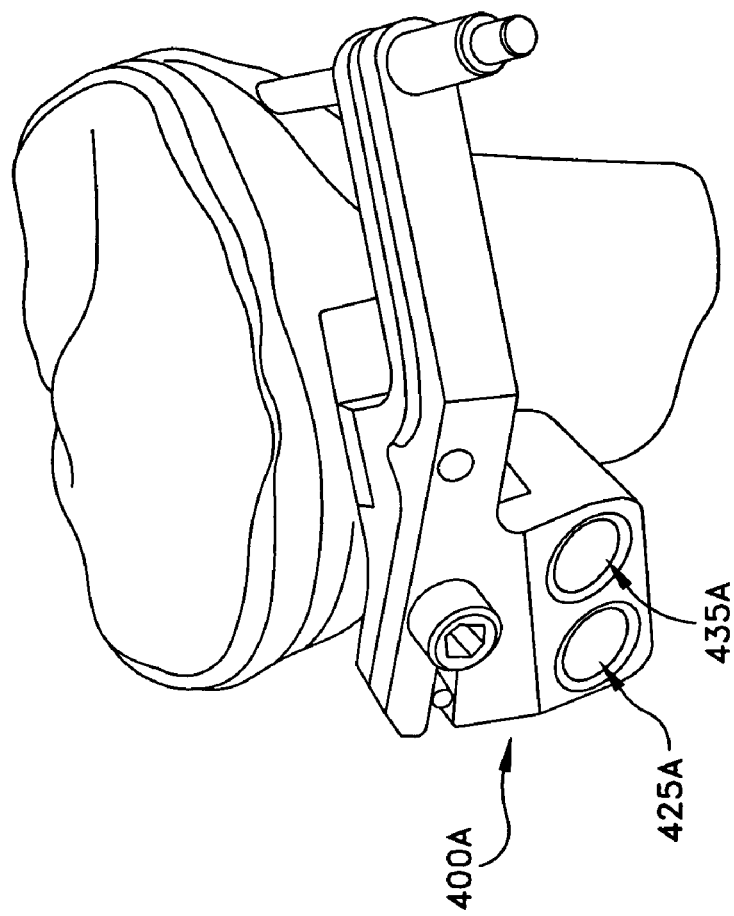
FIG. 34 is a schematic view showing a keyhole drill guide which may be used in conjunction with the wedge-shaped implant shown in FIGS. 31-33.

In order to provide appropriate keyholes 85A, 90A (FIG. 31) for receiving keys 820A, 825A, a keyhole drill guide 400A (also sometimes referred to as a "keystone drill template") may be used (FIG. 34). Keyhole drill guide 400A is generally similar to the keyhole drill guide 400 disclosed above, except that keyhole drill guide 400A has its two guide holes 425A, 435A disposed in a "side-by-side" disposition, rather than the "over-under" disposition of the two guide holes 425, 435 of drill guide 400.

Implant 800A (and drill guide 400A) may be used in an open wedge, high tibial osteotomy in a manner which is generally similar to that previously described with respect to implant 800 (and drill guide 400).

Providing implant 800A with two graft containment arms, e.g., posterior graft containment arm (GCA) 805A and anterior graft containment arm (GCA) 815A, is frequently preferred. However, in some circumstances, it may be desirable to omit one or both of posterior graft containment arm (GCA) 805A and anterior graft containment arm (GCA) 815A. Thus, in one preferred form of the invention, implant 800A comprises only base 810A and omits both posterior graft containment arm (GCA) 805A and anterior graft containment arm (GCA) 815A.

Providing implant 800A with a pair of keys 820A, 825A is generally preferred. However, in some circumstances, it may be desirable to omit one or the other of keys 820A, 825A. Furthermore, in other circumstances, it may be desirable to provide more than two keys, e.g., to provide three keys.

Furthermore, each of the keys 820A, 825A may include more than one bore 833A, 834A. Thus, for example, a key may include two bores, one angled upwardly so as to direct a fixation screw upwardly into the tibia above the key, and/or one angled downwardly so as to direct a fixation screw downwardly into the tibia below the key.

Figure 35:
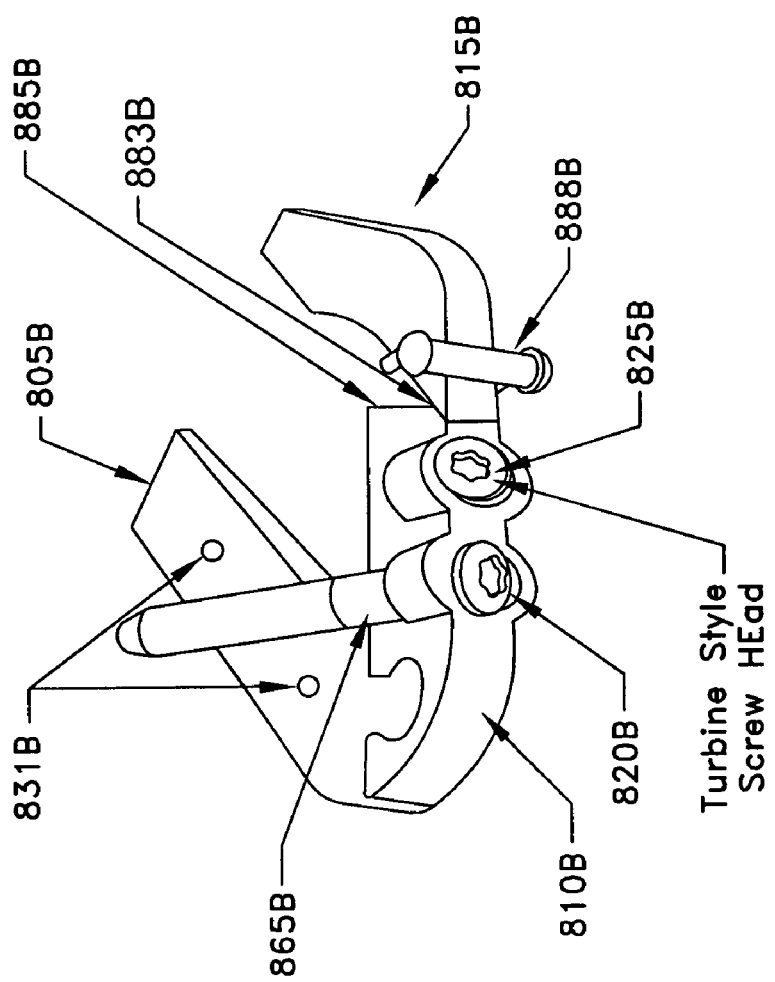
FIG. 35 is a schematic view showing another wedge-shaped implant formed in accordance with the present invention.

Looking next at FIG. 35, there is shown another implant 800B also formed in accordance with the present invention. Implant 800B is generally similar to the implant 800A disclosed above, except that implant 800B provides an alternative approach for joining the anterior graft containment arm (GCA) to the implant base, among other things.

More particularly, and still looking now at FIG. 35, implant 800B comprises a posterior graft containment arm (GCA) 805B, a base 810B and an anterior graft containment arm (GCA) 815B. Base 810B preferably comprises a pair of keys 820B, 825B. Keys 820B, 825B are laterally displaced along the width of base 810B, in a "side-by-side" configuration. Again, this is in contrast to the construction of implant 800, which uses an "over-under" configuration for its keys 820, 825 (FIG. 24).

Posterior graft containment arm (GCA) 805B includes a tab 870B, and base 810B includes a groove 873B, whereby posterior graft containment arm (GCA) 805B can mate with base 810B. Anterior graft containment arm (GCA) 815A includes a slide face 883B, and implant base 810B includes an opposing slide face 885B, whereby anterior graft containment arm (GCA) 815B can mate with base 810B. A bridge-type fastener 888B is used to secure anterior graft containment arm (GCA) 815B in position, with arm slide face 883B engaging base slide face 885B, after the implant is positioned within positioned within the wedge-like opening 25.

Posterior graft containment arm (GCA) 805B, and/or anterior graft containment arm (GCA) 815B, may include raised points or dimples 831B.

Keys 820B, 825B each include a bore 833B, 834B, respectively. Bores 833B, 834B receive fixation screws 865B for fixing implant 800B to the tibia. Bores 833B, 834B preferably diverge from the longitudinal axes of keys 820B, 825B, respectively, so as to direct fixation screws 865B downwardly or upwardly into the adjacent portions of the tibia. Keys 820B, 825B may also include external ribs 836B. External ribs 836B may extend longitudinally or circumferentially. Keys 820B, 825B may also be slotted (i.e., in a manner analogous to the slots provided in keys 820, 825 of implant 800), whereby to permit keys 820B, 825B to expand when fixation screws 865B are received in bores 833B, 834B.

Implant 800B may be used in an open wedge, high tibial osteotomy in a manner which is generally similar to that previously described with respect to implant 800.

Providing implant 800B with two graft containment arms, e.g., posterior graft containment arm (GCA) 805B and anterior graft containment arm (GCA) 815B, is frequently preferred. However, in some circumstances, it may be desirable to omit one or both of posterior graft containment arm (GCA) 805B and anterior graft containment arm (GCA) 815B. Thus, in one preferred form of the invention, implant 800B comprises only base 810B and omits both posterior graft containment arm (GCA) 805B and anterior graft containment arm (GCA) 815B.

Providing implant 800B with a pair of keys 820B, 825B is generally preferred. However, in some circumstances, it may be desirable to omit one or the other of keys 820B, 825B. Furthermore, in other circumstances, it may be desirable to provide more than two keys, e.g., to provide three keys.

Furthermore, each of the keys 820B, 825B may include more than one bore 833B, 834B. Thus, for example, a key may include two bores, one angled upwardly so as to direct a fixation screw upwardly into the tibia above the key, and/or one angled downwardly so as to direct a fixation screw downwardly into the tibia below the key.

Figure 36:
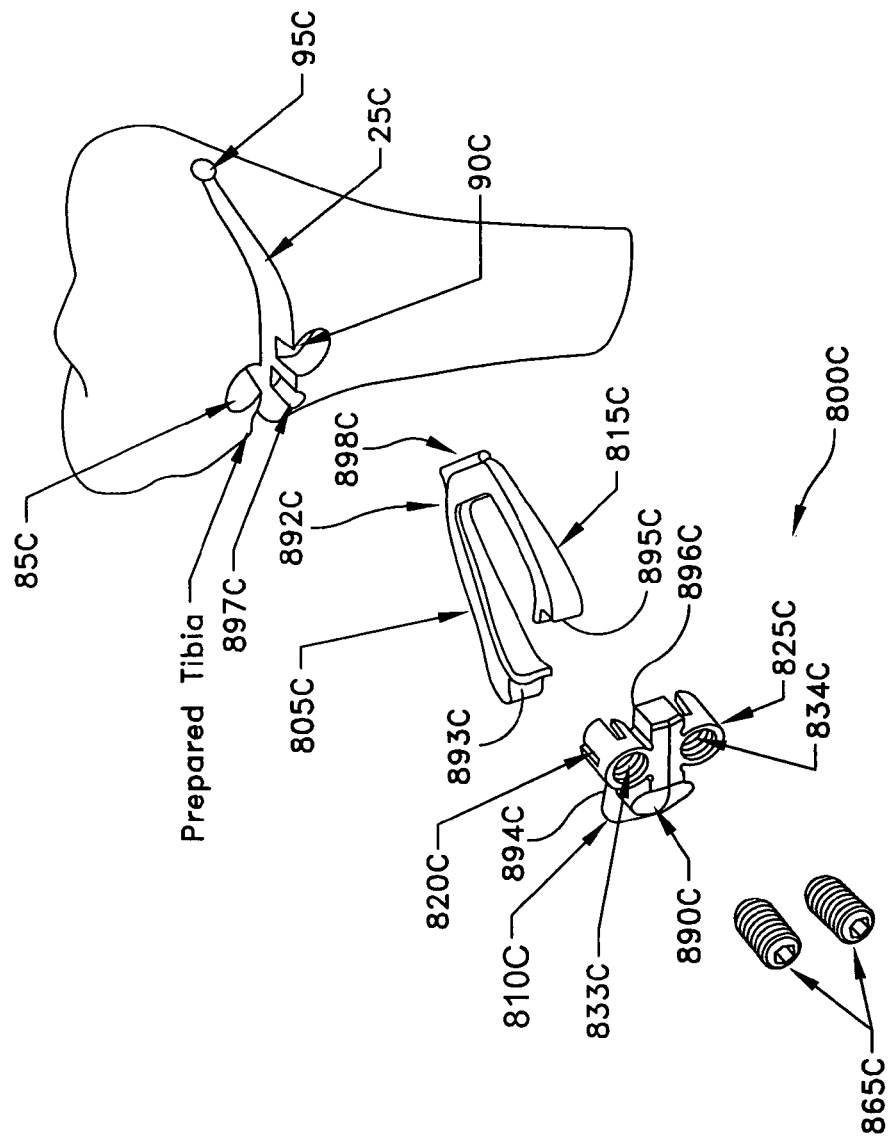
FIGS. 36-38 are schematic views showing still another wedge-shaped implant formed in accordance with the present invention.
Figure 37:
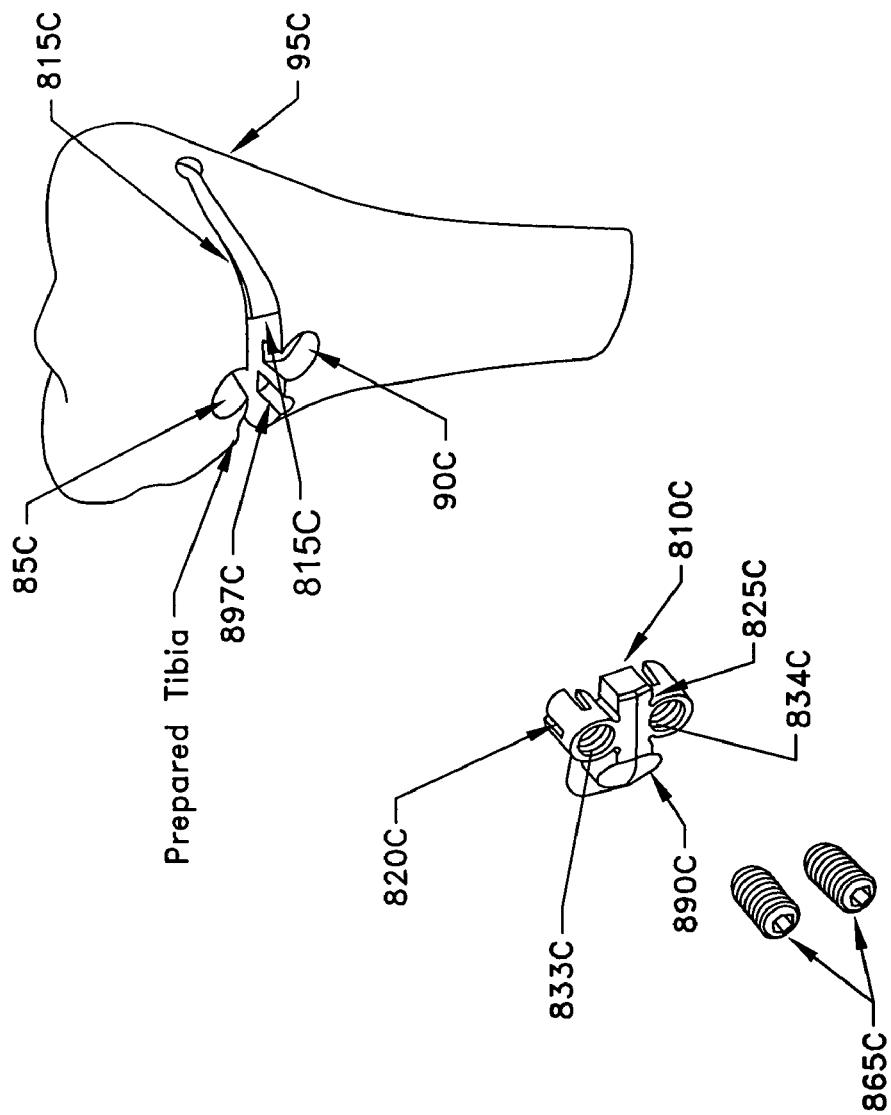
Figure 38:
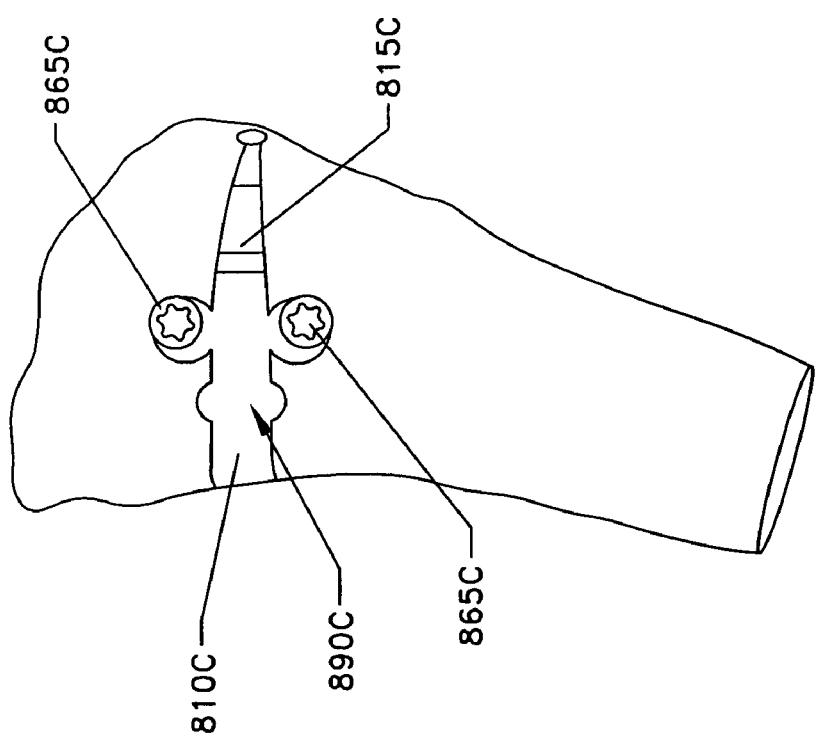

Looking next at FIGS. 36-38, there is shown an implant 800C also formed in accordance with the present invention. Implant 800C (which is also sometimes referred to as an expansion thread implant) is generally similar to the implant 800 disclosed above, except that implant 800C has a shear rib 890C on its base, laterally displaced from the two keys, as will hereinafter be discussed in further detail. Furthermore, implant 800C also provides an alternative approach for joining the posterior graft containment arm (GCA) to the base, and an alternative approach for joining the anterior graft containment arm (GCA) to the base, as will hereinafter also be discussed in further detail. Furthermore, implant 800C also provides a means for joining the distal end of posterior graft containment arm (GCA) 805C to the distal end of anterior graft containment arm (GCA) 815C, as will hereinafter also be discussed in further detail.

More particularly, and still looking now at FIGS. 36-38, implant 800C comprises a posterior graft containment arm (GCA) 805C, a base 810C and an anterior graft containment arm (GCA) 815C. Preferably a bridge 892C connects the distal end of posterior graft containment arm (GCA) 805C with the distal end of anterior graft containment arm (GCA) 815C.

A shear rib 890C is formed in base 810C, laterally displaced from the two keys 820C, 825C.

Posterior graft containment arm (GCA) 805C includes a recess 893C, and base 810C includes a shoulder 894C, whereby posterior graft containment arm (GCA) 805C can mate with base 810C. Anterior graft containment arm (GCA) 815C includes a recess 895C, and implant base 810C includes a shoulder 896C, whereby anterior graft containment arm (GCA) 815C can mate with base 810C.

Posterior graft containment arm (GCA) 805C, and/or anterior graft containment arm (GCA) 815C, may include raised points or dimples 831C.

Keys 820C, 825C each include a bore 833C, 834C, respectively. Bores 833C, 834C receive fixation screws 865C for fixing implant 800C to the tibia. The bores 833C, 834C may be axially aligned with the longitudinal axes of keys 820C, 825C, respectively. Alternatively, the bores 833C, 834C may be arranged so that they diverge from one another, downwardly and upwardly, respectively, so as to direct screws 865C deeper into the adjacent portions of the tibia. Keys 820C, 825C may also include external ribs 836C. External ribs 836C may extend longitudinally or circumferentially.

Keys 820C, 825C may also be slotted (i.e., in a manner analogous to the slots provided in keys 820, 825 of implant 800), whereby to permit keys 820C, 825C to expand when fixation screws 865C are received in bores 833C, 834C.

Shear rib 890C is laterally offset from keys 820C, 825C. Shear rib 890C projects above and below the top and bottom surfaces of base 810C. Among other things, it has been found that the provision of shear rib 890C provides, at the base of the implant, excellent load-bearing characteristics and substantial resistance to rotational and shear forces.

Figure 39:
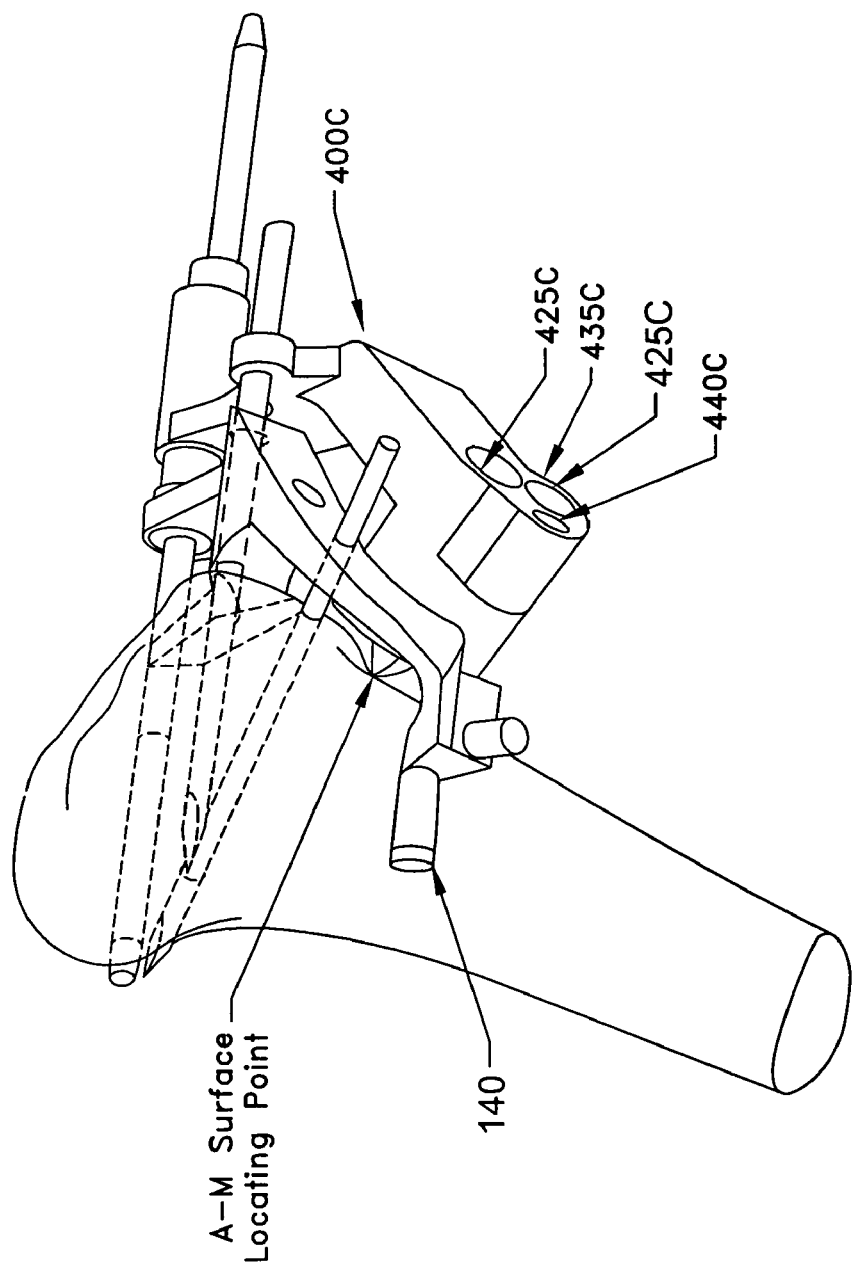
FIGS. 39-41 are schematic views show a keyhole drill guide and an end mill which may be used in conjunction with the wedge-shaped implant shown in FIGS. 36-38.
Figure 40:
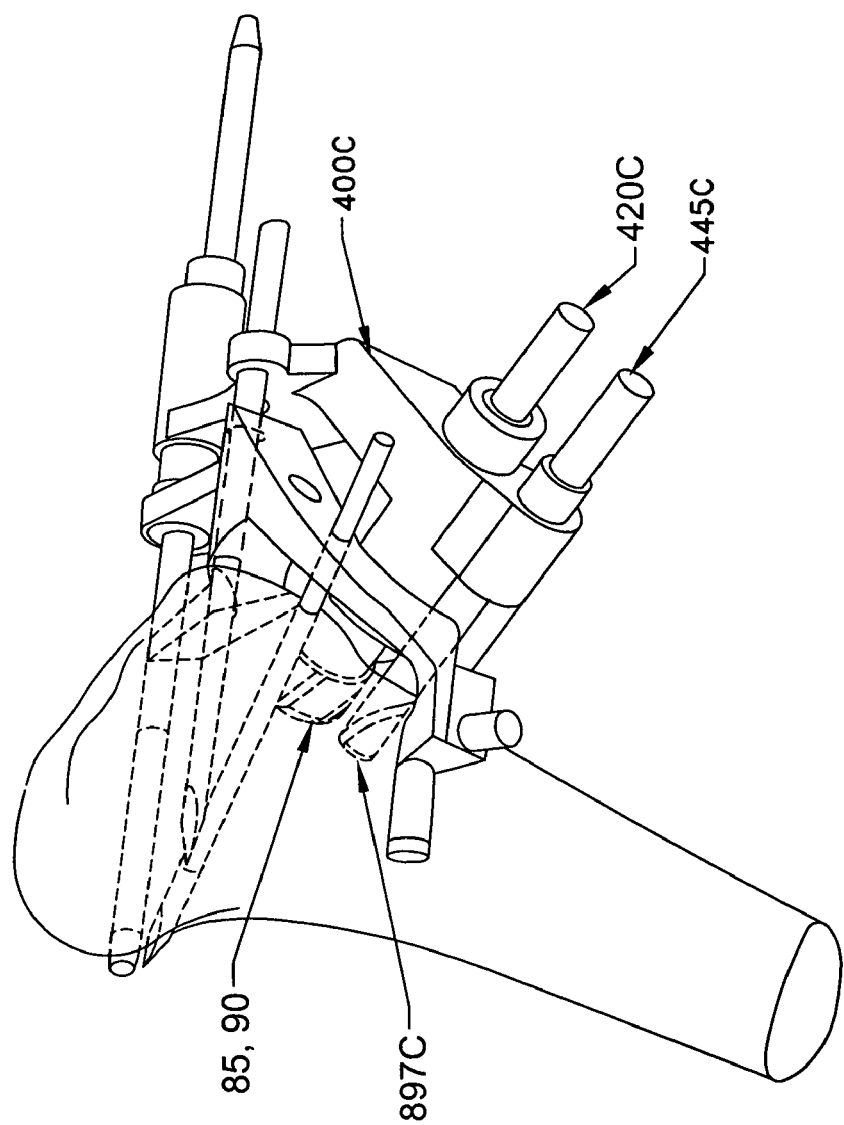

In order to provide appropriate keyholes 85C, 90C (FIG. 36) for receiving keys 820C, 825C, and also for providing a shear rib keyhole 897C for receiving shear rib 890C, a keyhole drill guide 400C (also sometimes referred to as a "keystone guide") may be used (FIGS. 39 and 40). Keyhole drill guide 400C is generally similar to the keyhole drill guide 400 disclosed above, except that keyhole drill guide 400C has, in addition to its two guide holes 425C, 435C, a shear rib guidehole 440C for forming shear rib keyhole 897C.

Implant 800C (and drill guide 400C) may be used in an open wedge, high tibial osteotomy in a manner which is generally similar to that previously described with respect to implant 800 (and drill guide 400), except that the bridged graft containment unit, i.e., posterior graft containment arm (GCA) 805C, bridge 892C and anterior graft containment arm (GCA) 815C, is installed as a single construction. Furthermore, when drill guide 400C is used to form keyholes 85C and 90C, it is also used to form shear rib keyhole 897C.

Providing implant 800C with two graft containment arms, e.g., posterior graft containment arm (GCA) 805C and anterior graft containment arm (GCA) 815C, is frequently preferred. However, in some circumstances, it may be desirable to omit one or both of posterior graft containment arm (GCA) 805C and anterior graft containment arm (GCA) 815C. Thus, in one preferred form of the invention, implant 800C comprises only base 810C and omits both posterior graft containment arm (GCA) 805C and anterior graft containment arm (GCA) 815C.

Providing implant 800C with a pair of keys 820C, 825C is generally preferred. However, in some circumstances, it may be desirable to omit one or the other of keys 820C, 825C. Furthermore, in other circumstances, it may be desirable to provide more than two keys, e.g., to provide three keys.

Furthermore, each of the keys 820C, 825C may include more than one bore 833C, 834C. Thus, for example, a key may include two bores, one angled leftwardly so as to direct a fixation screw leftwardly into the tibia to the left of the key, and/or one angled rightwardly so as to direct a fixation screw rightwardly into the tibia to the right of the key.

Figure 41:
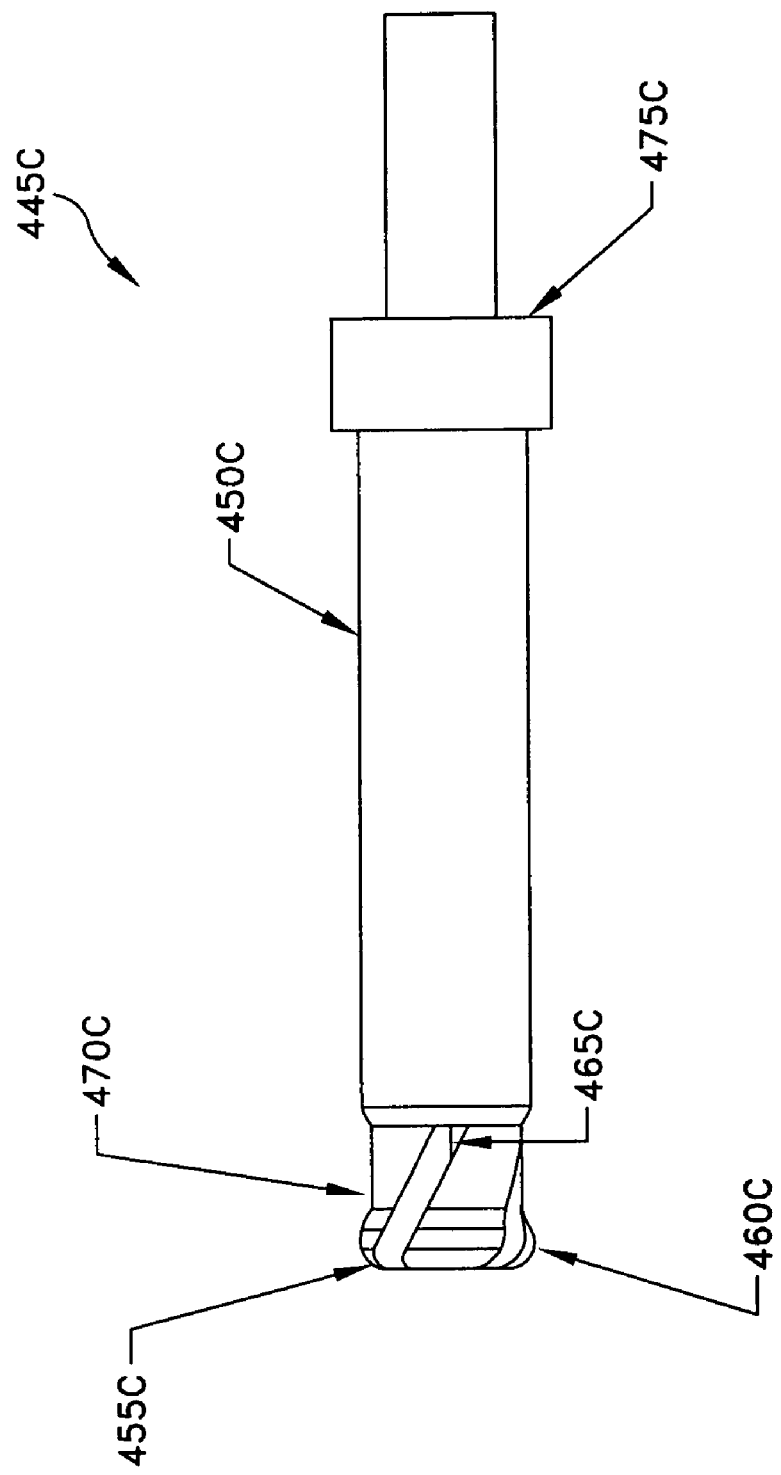

If desired, shear rib keyhole 897C can be formed using a conventional drill. More preferably, however, and looking now at FIGS. 40 and 41, shear rib keyhole 897C is formed using a shear rib end mill 445C. Shear rib end mill 445C generally comprises a shaft 450C having cutting edges 455C, a corner radius 460C and flutes (for chip removal) 465C. A relief area 470C is formed just proximal to corner radius 460C. An end stop (or flange) 475C limits, through engagement with drill guide 400C, the depth of shear rib keyhole 897C.

It is also possible to use a modified form of posterior protector 500, and a modified form of positioning guide 100, when practicing the present invention.

Figure 42:
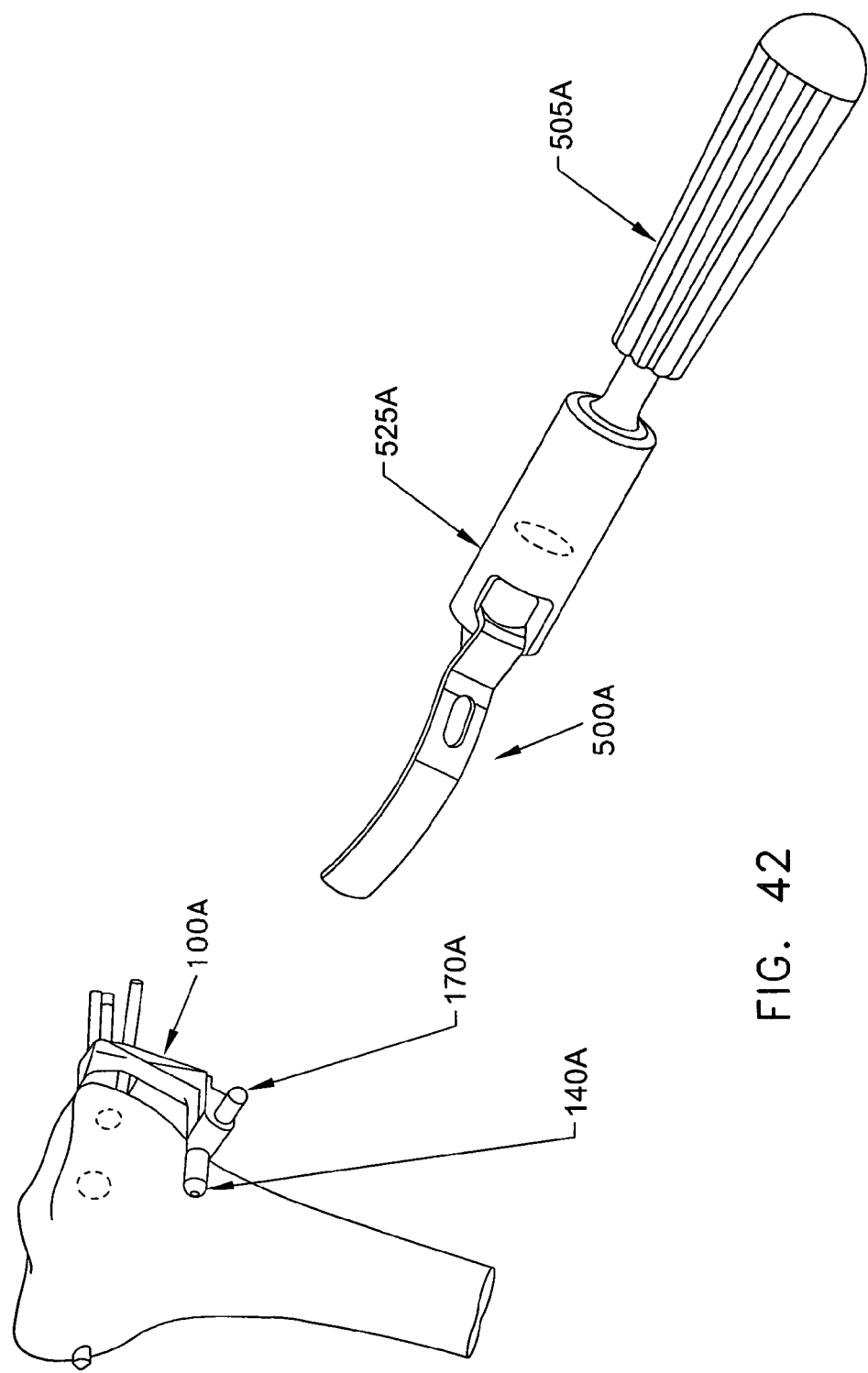
FIGS. 42-48 are schematic views showing alternative apparatus which may be used to form a cut in the tibia.
Figure 43:
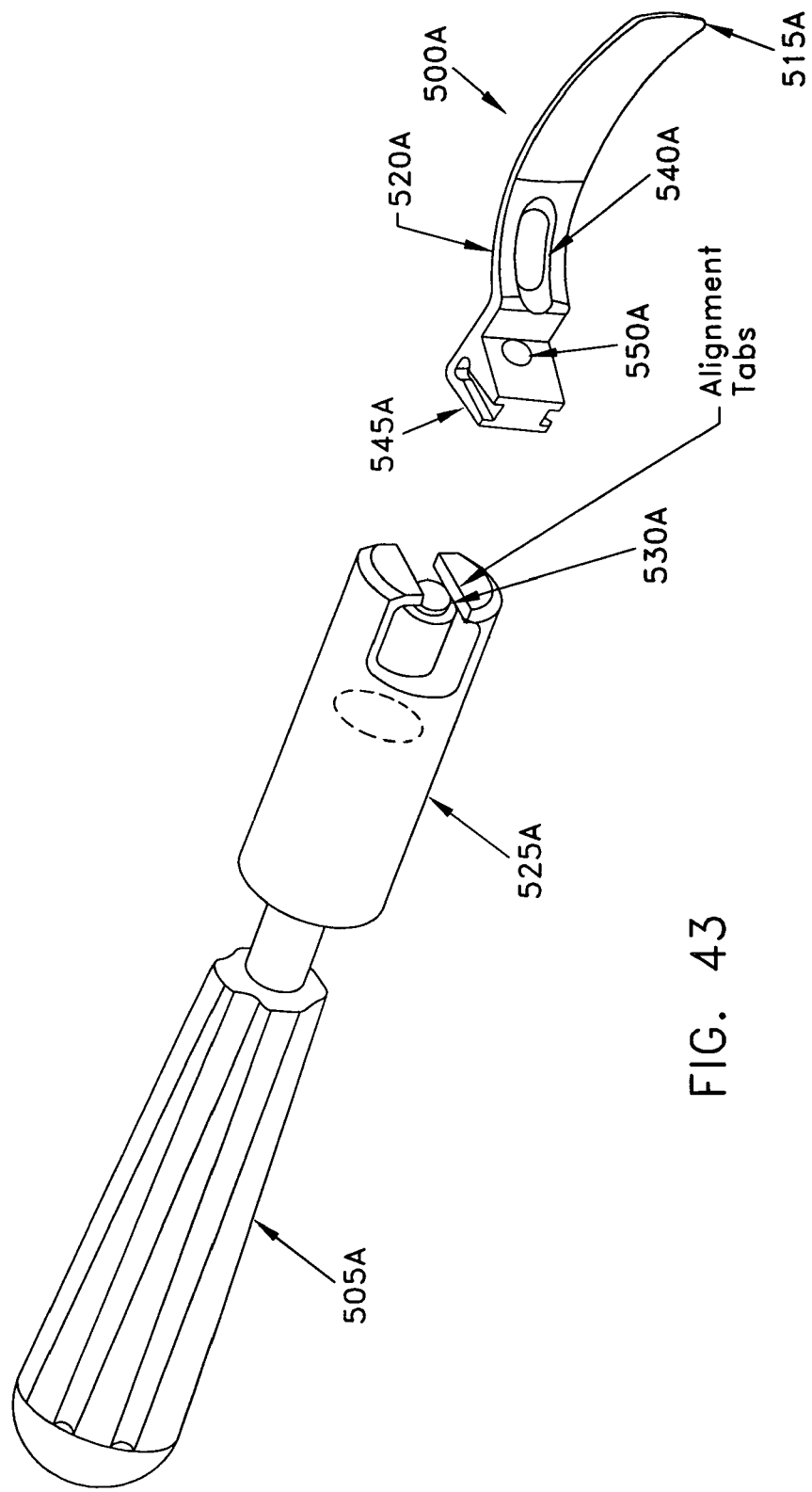

More particularly, and looking now at FIGS. 42 and 43, there is shown a posterior protector 500A which is intended to be used in conjunction with an introducer 505A having a clamping collar 525A and a plunger 530A. Posterior protector 500A includes a flexible far tip 515A and stiff curved portion 520A. A bore 540A extends through curved portion 520A. A base 545A is formed at the end of the curved portion 520A. Base 545A includes a bore 550A. Posterior protector 500A may be releasably secured to clamping collar 525A by positioning base 545A in clamping collar 525A and advancing plunger 530A against the proximal end of posterior protector 500A.

Figure 44:
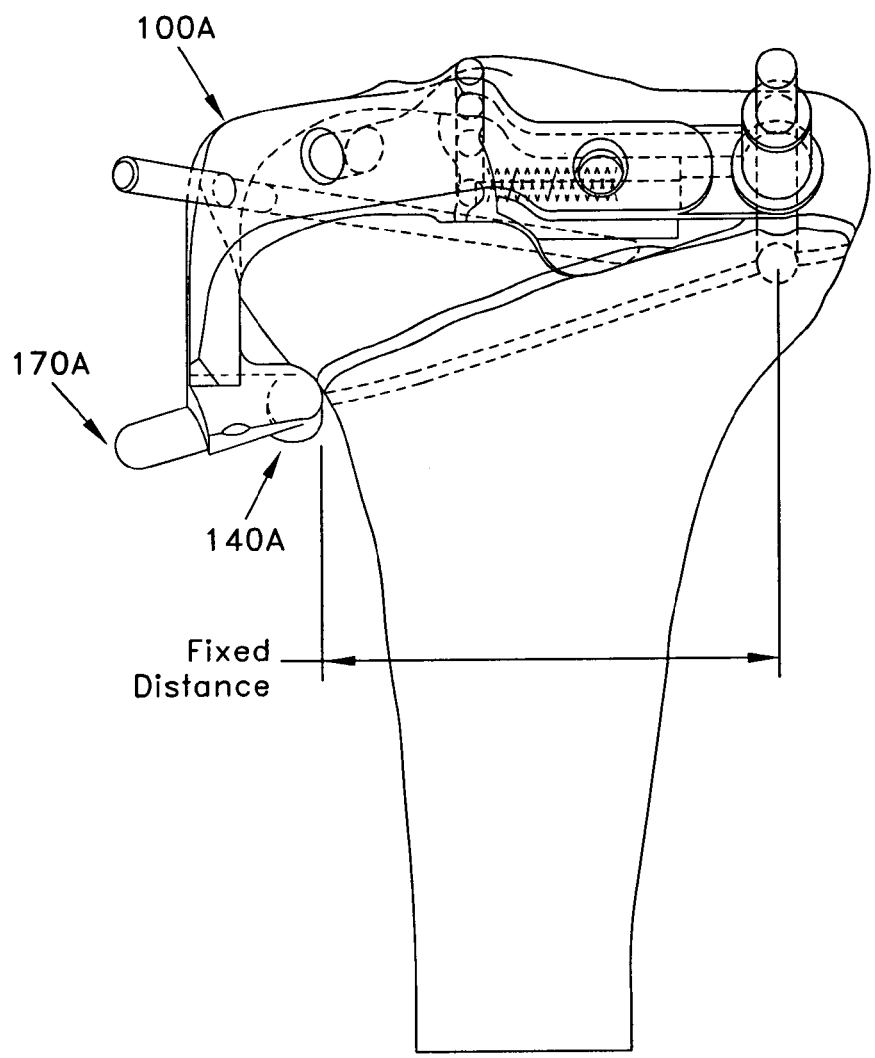
Figure 45:
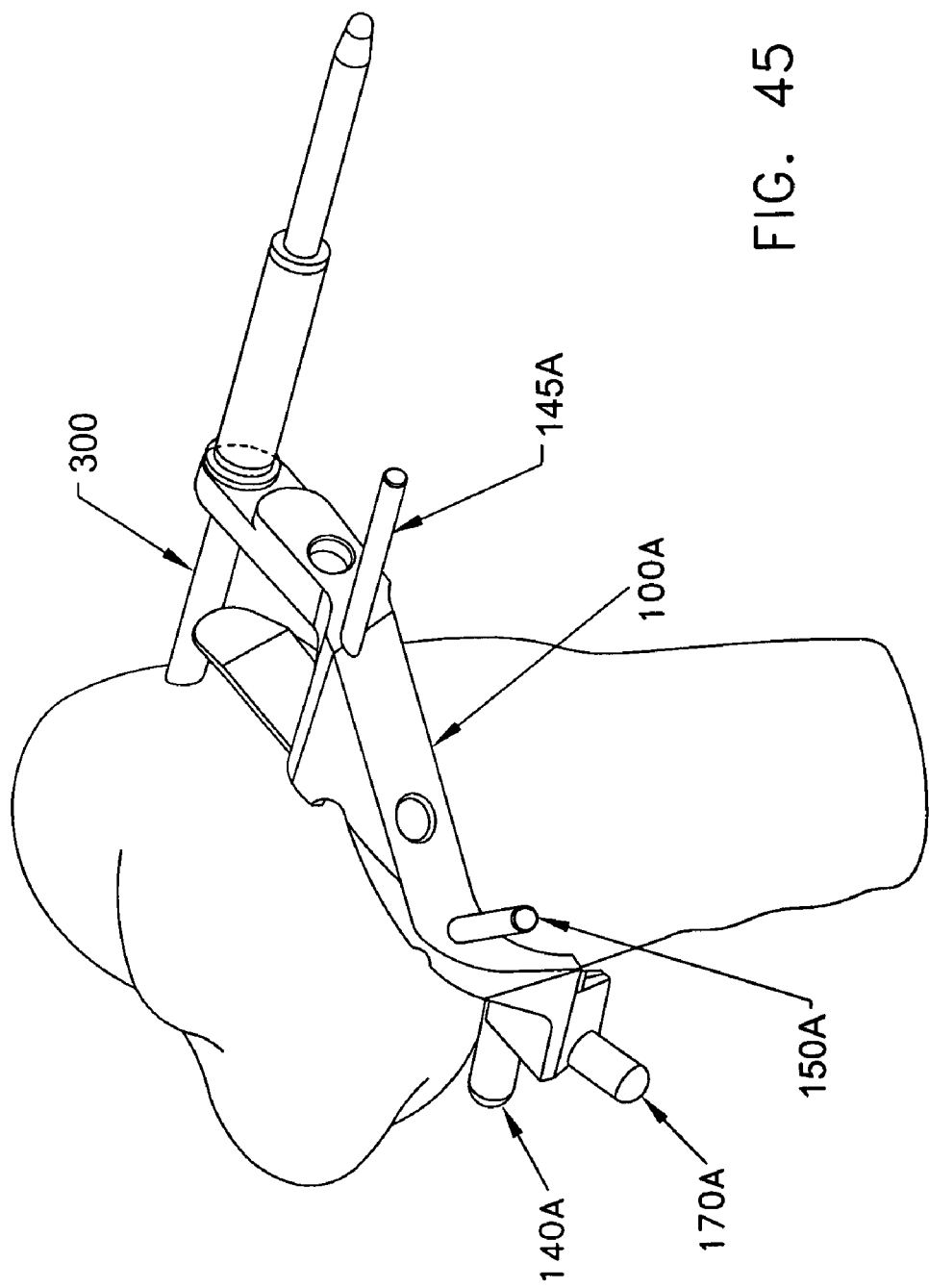
Figure 46:
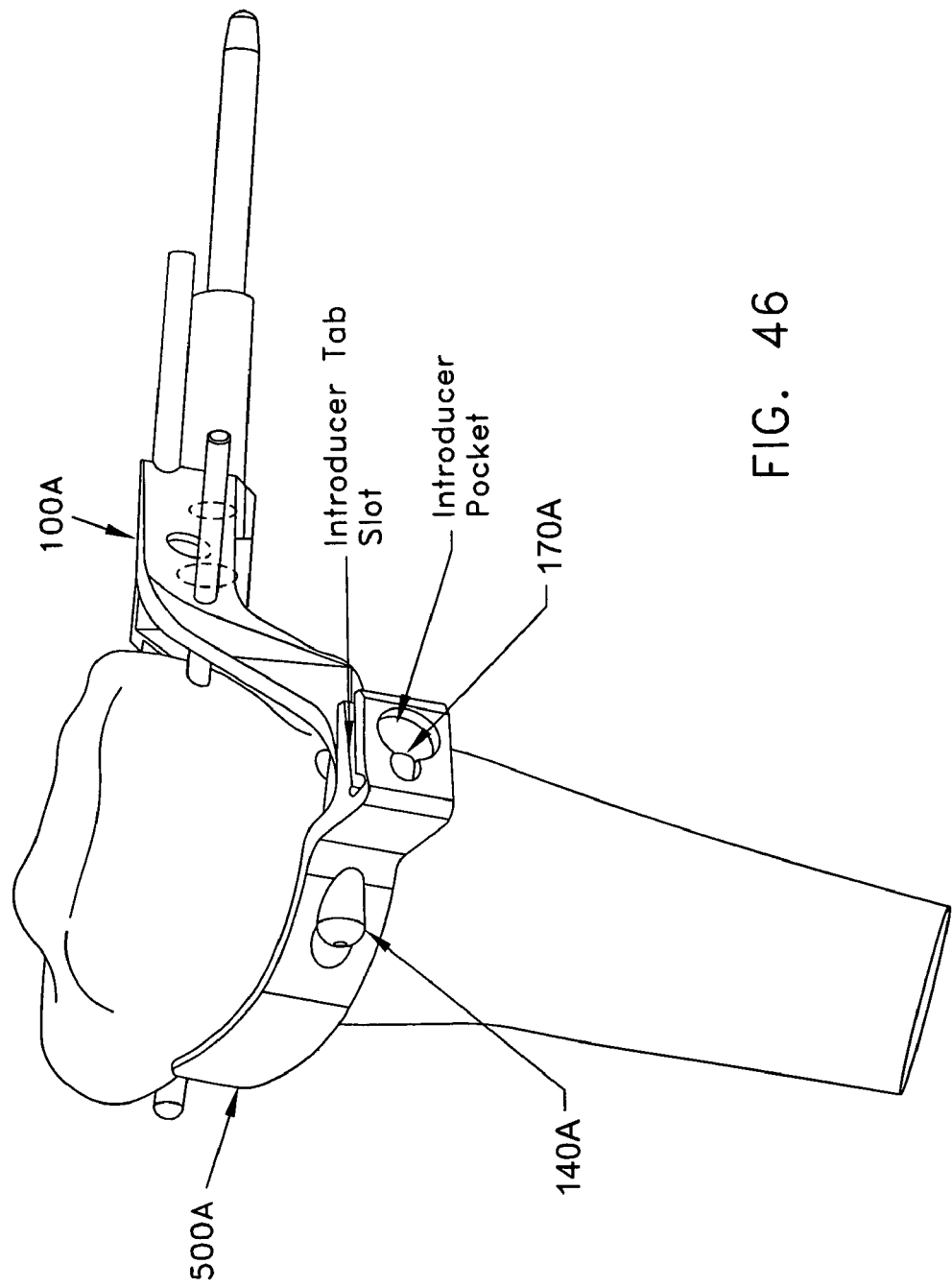
Figure 47:
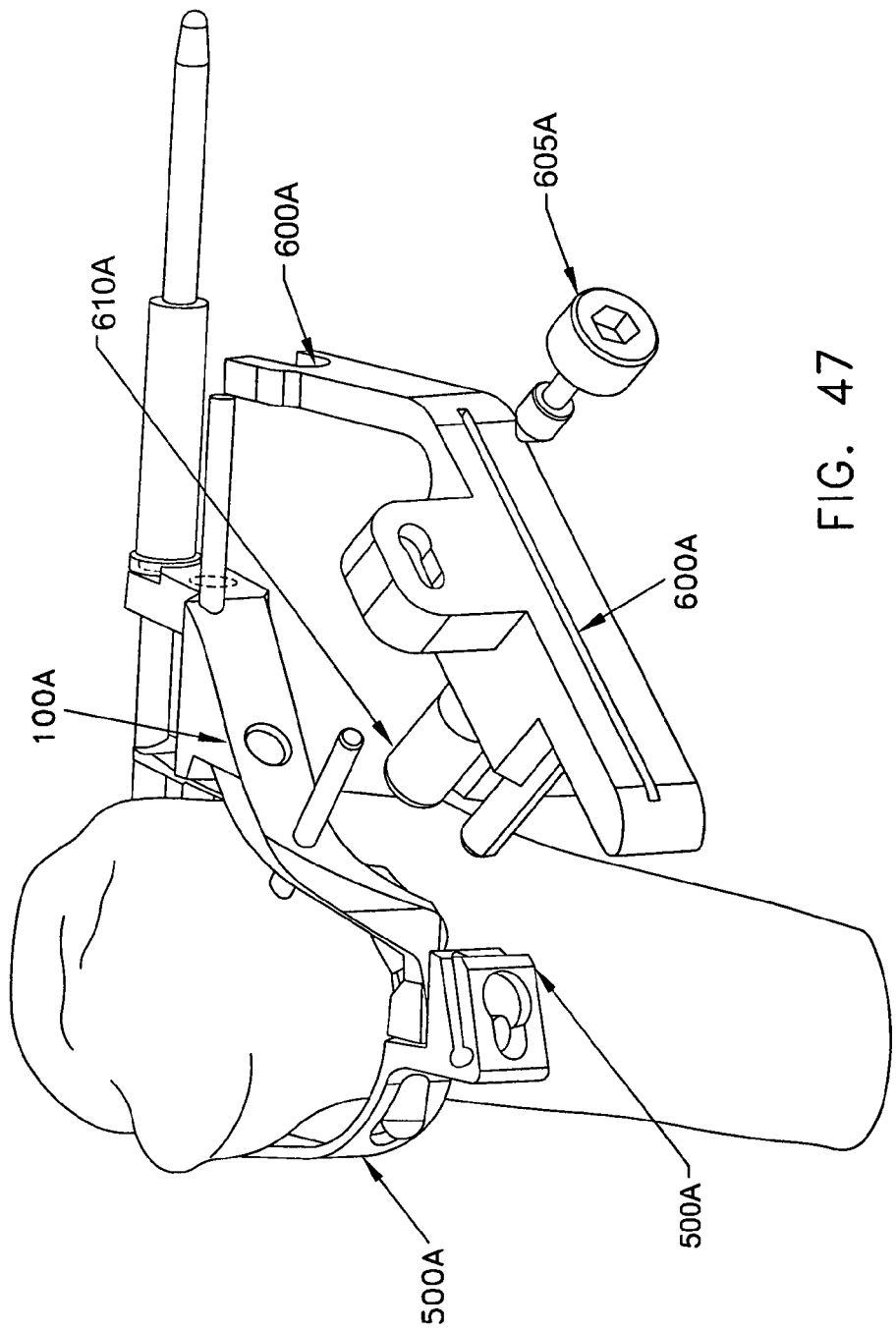
Figure 48:
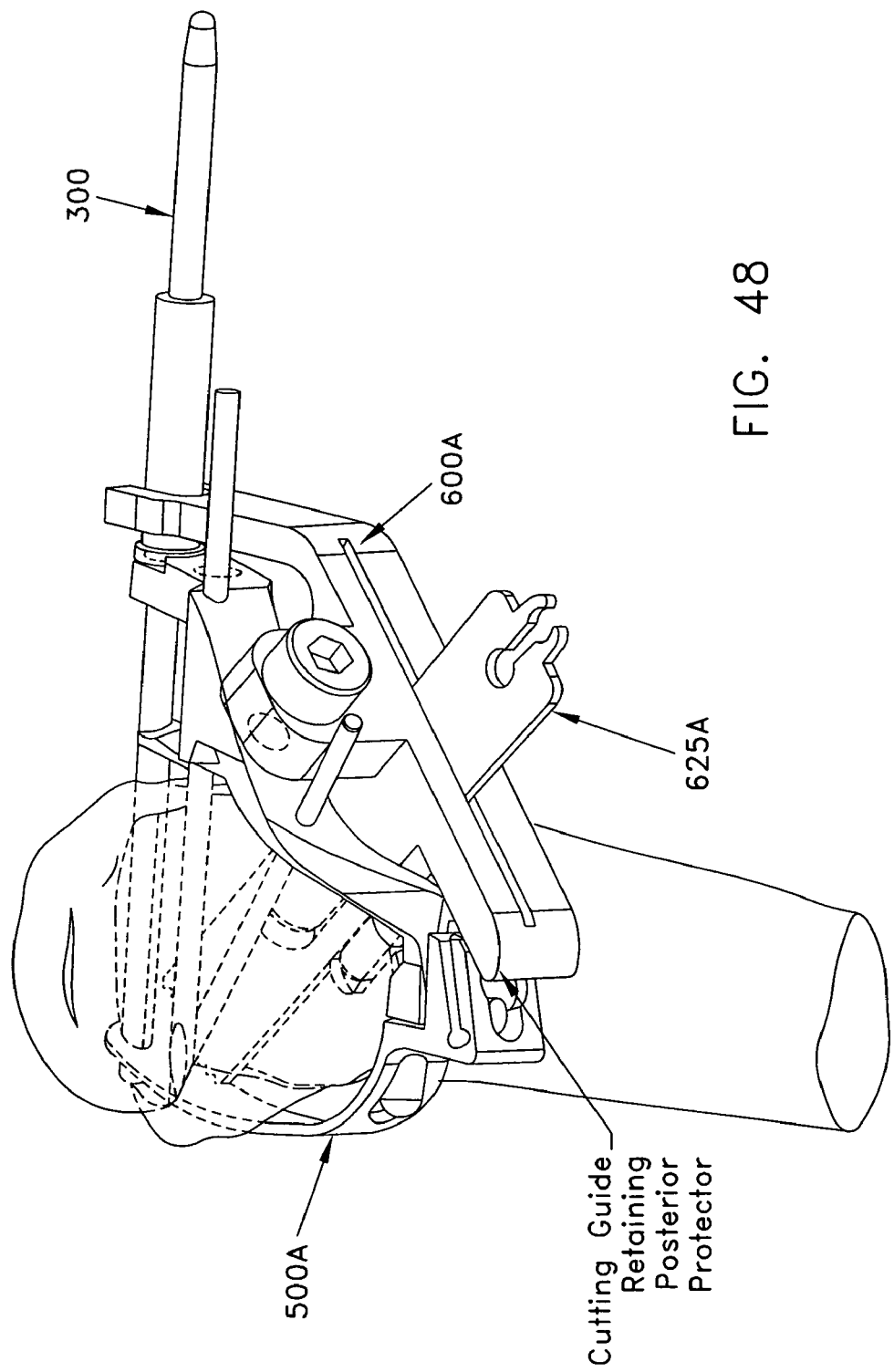

Posterior protector 500A may be used in conjunction with the positioning guide 100A shown in FIGS. 44 and 45. Positioning guide 100A includes, in addition to its normal elements, an introducer alignment pin 170A. Introducer alignment pin 170A preferably extends at a right angle to medial locating pin 140A. In use, and looking now at FIGS. 46-48, introducer 505A is used to position posterior protector 500A so that far tip 515A and curved portion 520A are properly positioned relative to the patient's anatomy, and so that medial locator pin 140A extends through bore 540A and introducer alignment pin 170A extends through bore 550A. Then introducer 505A is disengaged from posterior protector 500A (FIG. 46), leaving posterior protector 500A extending across the posterior cortex of the tibia, interposed between the tibia and the delicate neurological and vascular structures located at the back of the knee. Thereafter a cutting guide 600A may be secured to positioning guide 100A (FIG. 47), and saw blade 625A is used to form osteotomy cut 20.

Figure 49:
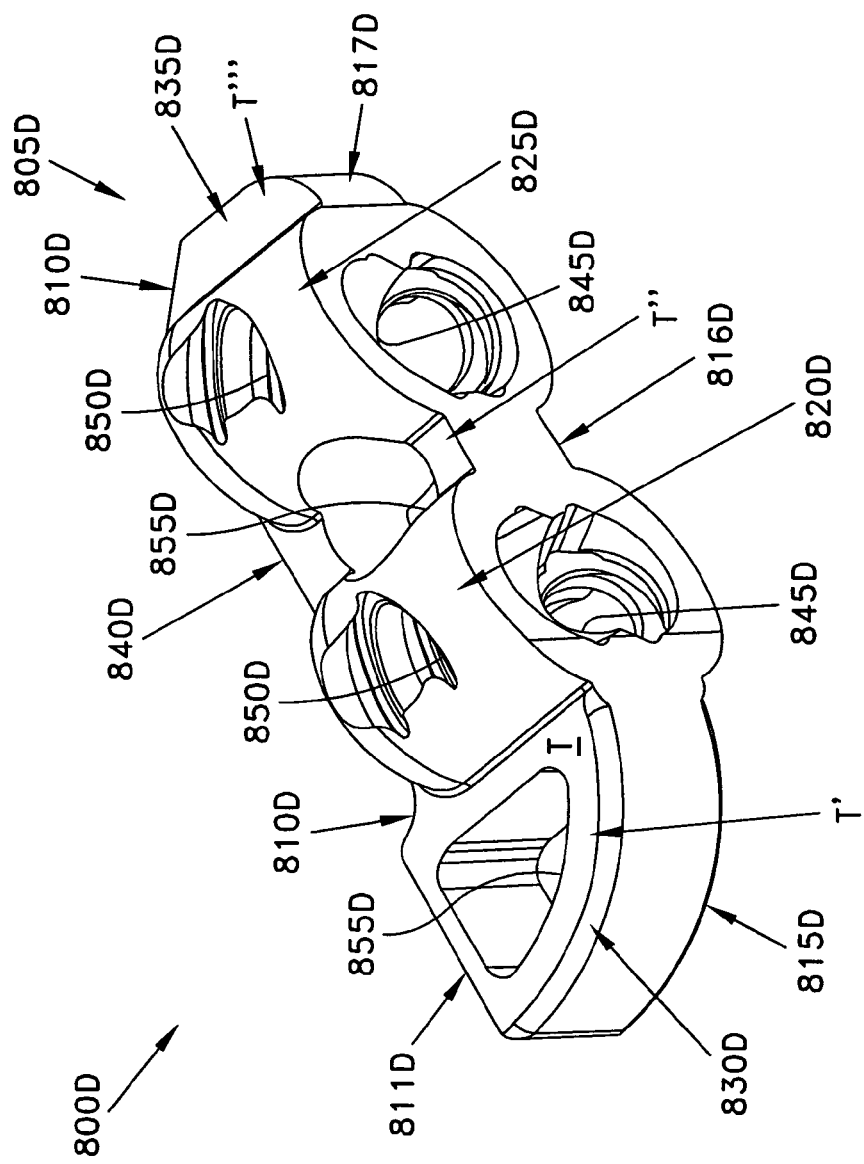
FIG. 49-56 are schematic views showing alternative single-body implant constructions.

Looking next at FIG. 49, there is shown a novel implant 800D also formed in accordance with the present invention. Implant 800D is generally characterized by: (i) a body for disposition within the wedge-shaped opening of the osteotomy and supporting the tibia while healing occurs, (ii) at least one key formed integral with the body for stabilizing the body relative to the tibia while healing occurs, and (iii) at least one fenestration extending through the body for permitting bone growth through the implant.

In one preferred construction, and looking now at FIG. 49, novel implant 800D comprises a beveled, J-shaped body 805D characterized by a curved leading face 810D, a flat leading face 811D, a curved trailing face 815D, a flat trailing face 816D, a second curved trailing face 817D, a top surface T, and a bottom surface B. Curved leading face 810D and flat leading face 811D are intended to be directed towards the oversized, circular diameter hole 95 at the base of the apex cut, while curved trailing face 815D, flat trailing face 816D and second curved trailing face 817D are intended to approximate the shape of the cortex of the proximal tibia, both medially and antero-medially.

Top surface T and bottom surface B are intended to engage the upper and lower portions of the tibia at the wedge-shaped osteotomy opening. To this end, top surface T and bottom surface B are preferably planar.

Furthermore, top surface T and bottom surface B may converge toward one another in the distal direction (e.g., toward the base of the apex cut), or they may be parallel to one another.

J-shaped implant body 805D also comprises a pair of keys 820D, 825D laterally spaced along its width in a "side-by-side" configuration. J-shaped implant body 805D further comprises a first, arcuate, lateral extension 830D extending adjacent to key 820D, and a second lateral extension 835D extending adjacent to key 825D.

Keys 820D, 825D extend between leading face 810D and trailing face 815D and are connected by a bridge 840D. Where implant 800D is provided with more than one key connected by a bridge, the keys subdivide top surface T and bottom surface B into a plurality of laterally-spaced surface segments, see for example, T', T'' and T''' in FIG. 49. Where top surface T and bottom surface B are subdivided into a plurality of laterally-spaced surface segments, these segments may each be planar and, if desired, coplanar with one another. Keys 820D, 825D preferably each include bores 845D, 850D. Bores 845D, 850D receive fixation screws 865D for fixing implant 800D to the tibia, with bores 845D directing the fixation screws downwardly and bores 850D directing the fixation screws upwardly. Bores 845D, 850D may be longitudinally aligned with the longitudinal axis of the keys 820D, 825D, respectively, in at least one dimension. By way of example but not limitation, and as shown in FIG. 49, bores 845D, 850D are preferably arranged so that they diverge from one another, downwardly and upwardly, respectively, so as to direct fixation screws 865D through top surface T and/or bottom surface B, and deeper into the adjacent portions of the tibia.

Furthermore, and looking still at FIG. 49, implant 800D may be provided with one or more fenestrations 855D. By way of example but not limitation, one fenestration 855D may be formed in first, arcuate, lateral extension 830D, while another fenestration 855D may be formed in between keys 820D, 825D through bridge 840D. Fenestrations 855D extend from top surface T through to bottom surface B and allow a path for bone growth and re-vascularization vertically through the implant. Fenestrations 855D may be filled prior to surgery with de-mineralized bone, synthetic graft material, etc., or may be filled with graft material during surgery.

For purposes of illustration, fenestrations are shown in FIG. 49 as each having specific geometries, however, it should be appreciated that the fenestrations can be formed having various geometric shapes in order to provide different re-growth and/or support advantages for the implant. The fenestrations may be configured, arranged and/or shaped in accordance with their desired function. By way of example but not limitation, the fenestrations may be configured so as to address one or more of the following: (i) optimizing bone re-growth, (ii) directing bone-growth in specific areas or directions, (iii) providing a specific effective modulus (or stiffness) in one or more directions during the healing period, and (iv) optimizing stiffness so as to provide an optimum strain rate in the osteotomy during the healing period, etc.

Providing implant 800D with a pair of keys 820D, 825D is generally preferred. However, in some circumstances, it may be desirable to omit one or the other of keys 820D, 825D. By way of example, in some circumstances it may be desirable to minimize the "footprint" of the implant in order to preserve the maximum amount of native bone. Similarly, it may be desirable to have the keys semi-merged or overlapped, thereby omitting bridge 840D therebetween.

Furthermore, in other circumstances, it may be desirable to provide more than two keys, e.g., to provide three keys.

Moreover, each of the keys 820D, 825D may include only one bore therethrough.

It should be appreciated that the provision of first, arcuate, lateral extension 835D and second lateral extension 840D replaces posterior graft containment arm and/or anterior graft containment arm as used with implant 800. Thus, in a preferred form of the invention, implant 800D comprises only J-shaped implant body 805D and omits both posterior graft containment arm (GCA) and anterior graft containment arm (GCA). However, if desired, posterior graft containment arm and/or anterior graft containment arm may be used with implant 800D.

It is also possible to provide implant 800D with more than two fenestrations 855D, or to provide implant 800D with additional fenestration configurations.

Looking next at FIG. 50, there is shown an implant 800E generally similar to implant 800D, except replacing the singular fenestration formed in the first, arcuate, lateral extension with additional fenestrations, as will hereinafter be discussed in further detail.

As in implant 800D, a fenestration 855E is formed through bridge 840E, between keys 820E, 825E.

Figure 50:
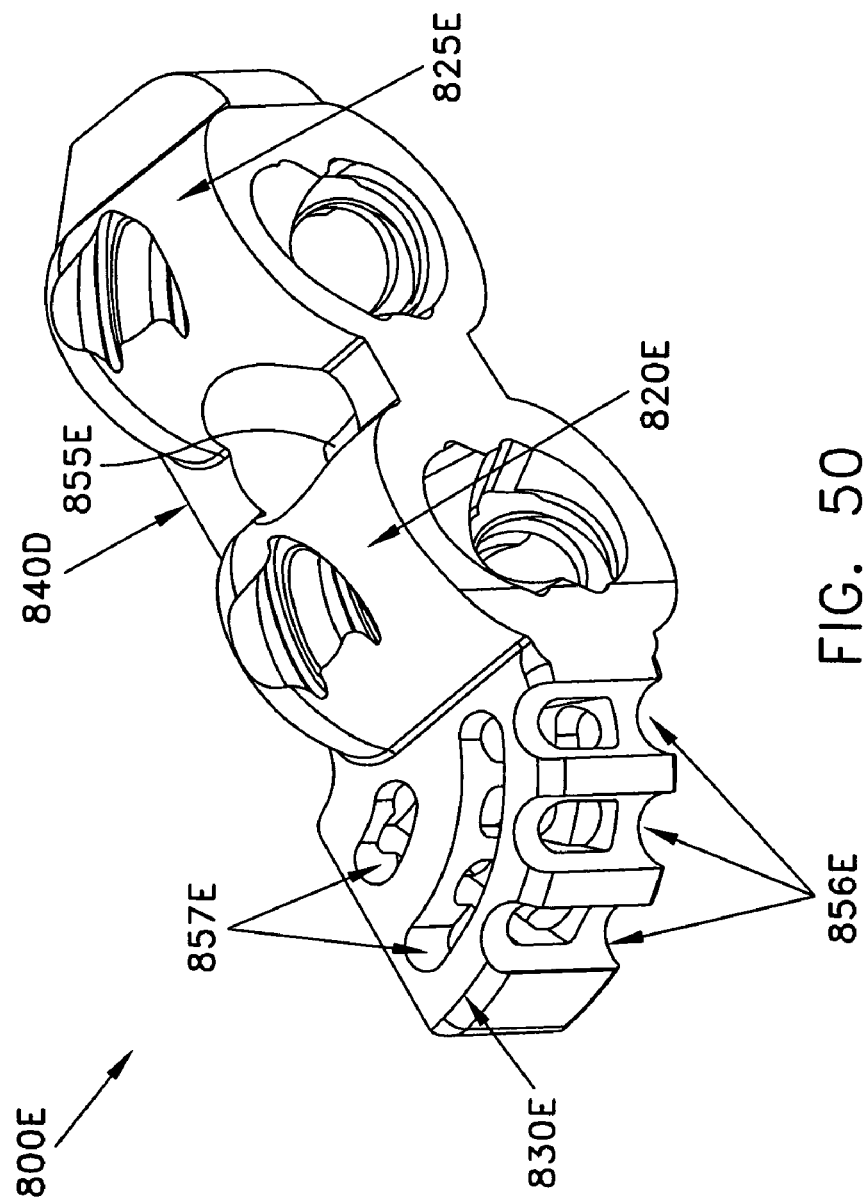

Furthermore, and looking still at FIG. 50, implant 800E may be provided with one or more different fenestration configurations. By way of example but not limitation, radial fenestrations 856E and axial fenestrations 857E may be formed in first, arcuate, lateral extension 830E.

Radial fenestrations 856E are formed along the curved trailing face portion of first, arcuate, lateral extension 830E and create intersecting openings with axial fenestrations 857E.

All fenestrations may extend from top surface T through bottom surface B and allow a path for bone growth and re-vascularization through the implant.

Fenestrations may be filled prior to surgery with de-mineralized bone, synthetic graft material, etc., or may be filled with graft material during the surgery.

Because bone will regrow into the openings throughout implant 800E formed by the fenestrations, providing implant 800E with multiple fenestrations increases surface area and direction for bone regrowth.

Figure 51:
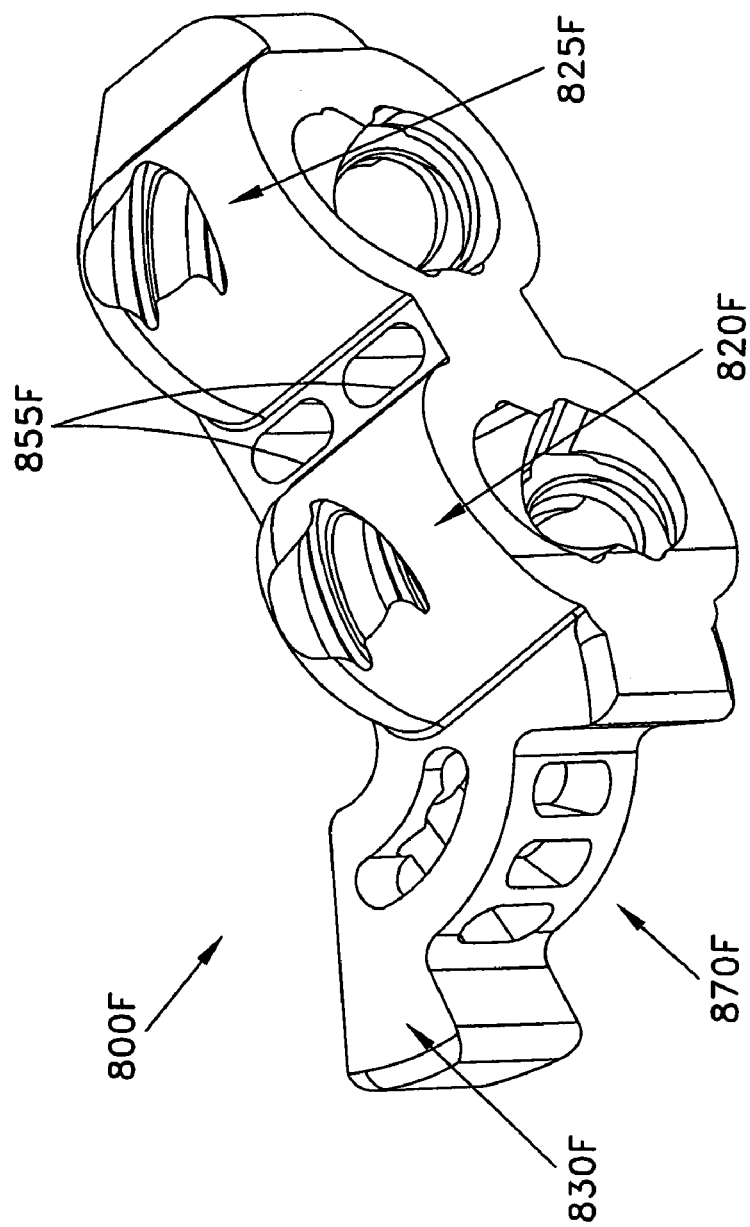

Looking next at FIG. 51, there is shown an implant 800F which is generally similar to implant 800E described above, except with an elongated first, arcuate, lateral extension 830F, which will hereinafter be discussed in further detail.

Elongated first, arcuate, lateral extension 830F extends further posteriorly and radially from key 820F than first, arcuate, lateral extension 830E of implant 800E. By elongating first, arcuate, lateral extension 830F, implant 800F provides additional support during healing. Elongated first, arcuate, lateral extension 830F preferably comprises radial and axial fenestrations generally similar to implant 800E.

Unlike implant 800E, however, in which one singular fenestration is formed in the bridge between the keys, two separate fenestrations 855F are formed through bridge 840F between keys 820F.

Furthermore, elongated first, arcuate, lateral extension 830F also comprises a perimeter recess 870F formed in trailing face 815F. Recess 870F allows cortical bone to regenerate during healing.

It may be desirable to form the implant of the present invention with an elongated first, arcuate, lateral extension having a leading face rib, in place of recess on the trailing face as will hereinafter be discussed in further detail.

Figure 52:
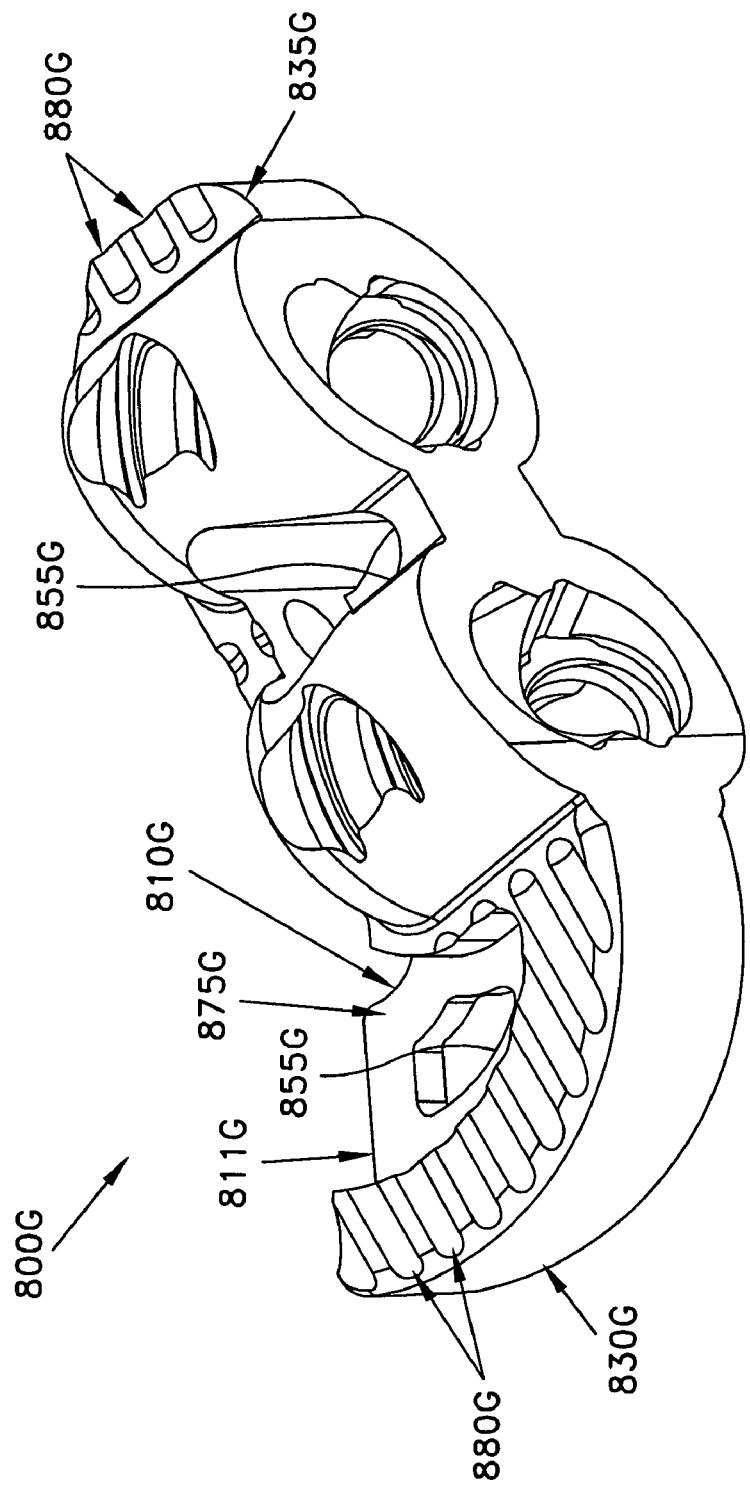

Looking next at FIG. 52, there is shown an implant 800G which is generally similar to implant 800F except that it comprises a rib 875G formed in first, arcuate, lateral extension extending along leading face 810G and flat leading face 811G. Implant 800G also omits the radial and axial fenestrations of 800F.

Rib 875G provides leading face 810G and flat leading face 811G with a minimal profile as it is positioned into place in the osteotomy, but provides substantial stability to first, arcuate, lateral extension 830G as well as implant 800G.

Furthermore, both first, arcuate, lateral extension 830G and/or second lateral extension 835G comprise external grooves 880G. External grooves 880G provide implant 800G with additional stability against shear forces within the osteotomy, and may be formed on the top and/or bottom surface of first, arcuate, lateral extension 830G and/or second lateral extension 835G.

Implant 800G is provided with two fenestrations 855G. As shown in FIG. 52, one fenestration 855G is formed in rib 875G and another fenestration 855G is formed in between keys 820G, 825G through bridge 840G. By way of example but not limitation, fenestration 855G through bridge 840G is shown having a triangular geometry.

Figure 53:
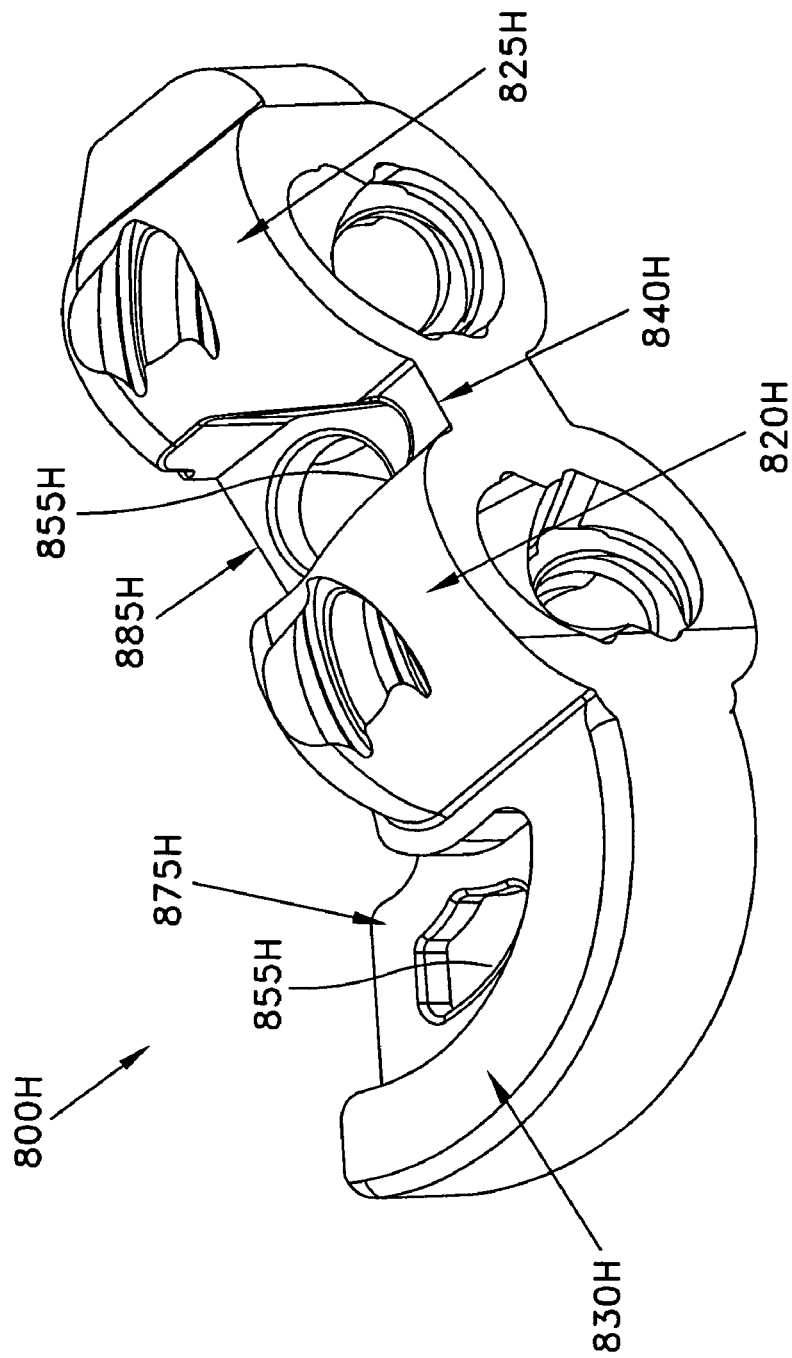

Looking next at FIG. 53, there is shown an implant 800H which is generally similar to implant 800G, except with a bridge rib 885H formed along the leading face of the bridge 840H which connects the keys as will hereinafter be discussed in further detail.

A portion of bridge 840H, between keys 820H, 825H, is removed so as to form a bridge rib 885H along the leading face 810H of implant 800H. Bridge rib 885H, in conjunction with rib 875H, provides leading face 810H with a minimal profile as it is positioned into place within the osteotomy, but still provides substantial stability to first, arcuate, lateral extension 830H as well as implant 800H. Fenestrations 855H are formed in both rib 875H and bridge rib 885H.

It should be appreciated that, depending on their placement, the afore-mentioned fenestrations may be enlarged to effectively evacuate or remove portions of the J-shaped implant, so as to re-tailor the periphery of the implant.

By way of example but not limitation, and looking next at FIGS. 54 and 55, there is shown an implant 800I which is generally similar to implant 800H but with enlarged fenestrations 855I formed along the leading face so as to essentially create evacuated portions from first, arcuate, lateral extension 830I, bridge 840I and second lateral extension 835I, as will hereinafter be discussed in further detail.

Figure 54:
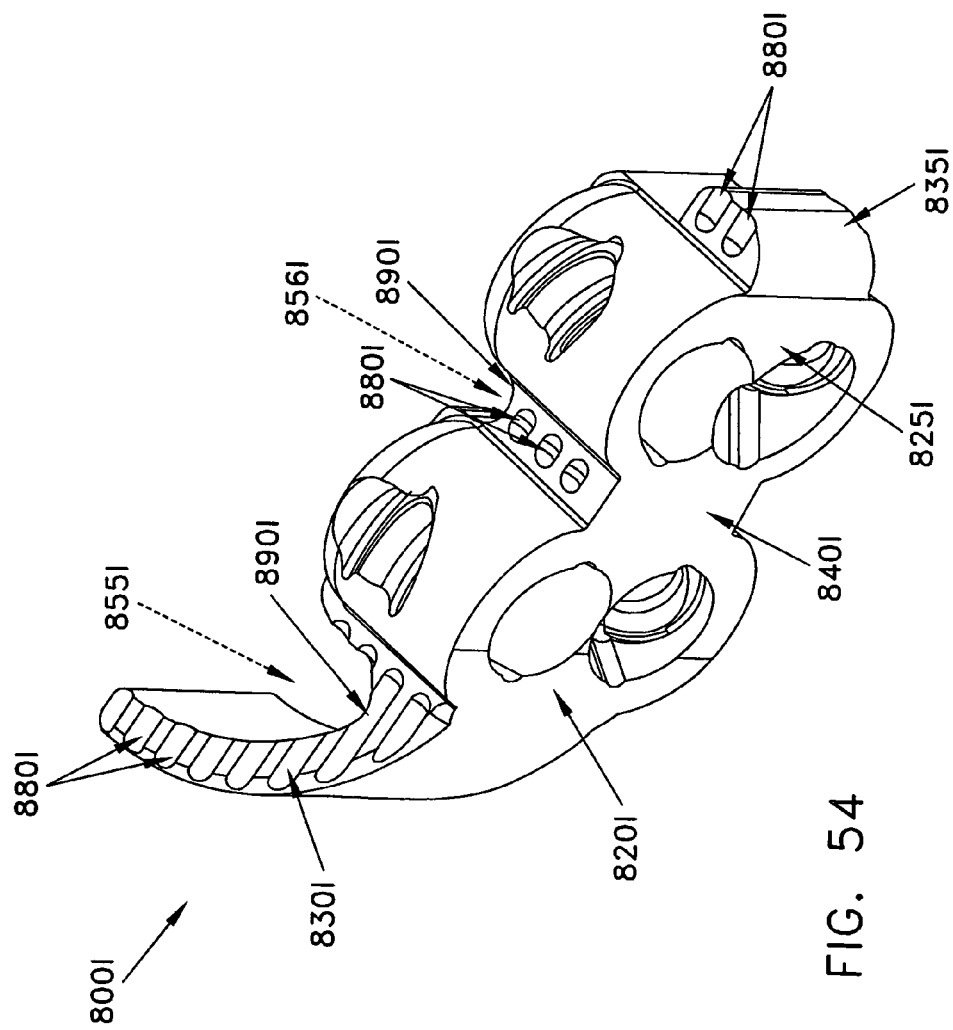
Figure 55:
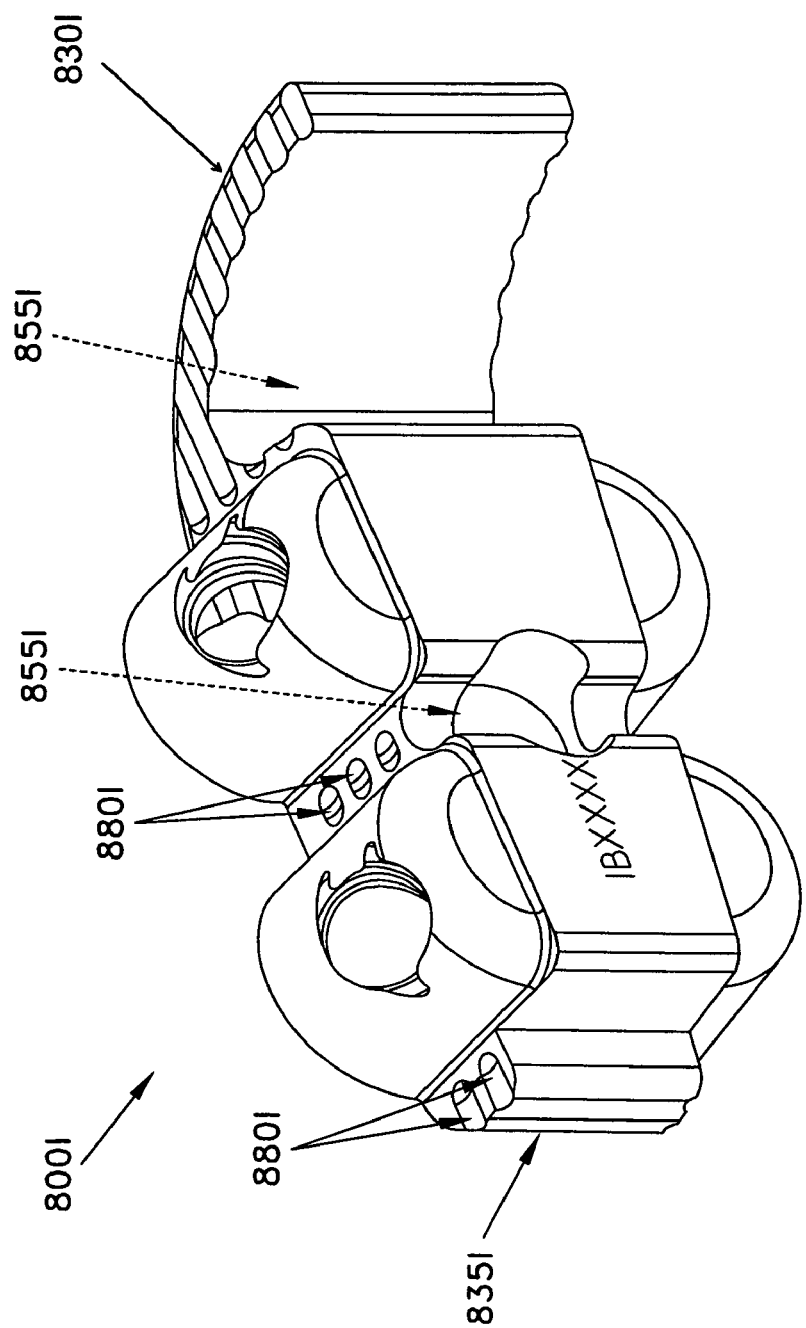

As shown in FIG. 54, fenestration 855I is positioned along the leading face and flat leading face of first, arcuate, lateral extension 830I so as to create a grooved recessed portion 890I. In this form of the present invention, first, arcuate, lateral extension 830I generally comprises a hook-shaped wall.

A second fenestration 856I created in the leading face of bridge 840I forms a grooved recessed portion 890I between keys 820I, 825I. Second lateral extension 835I is configured so as to also have a portion removed from its leading face, leaving a smaller, tab-shaped extension.

Implant 800I also comprises external grooves 880I formed first, arcuate, lateral extension 830I, second lateral extension 835I and bridge 840I.

By forming implant 800I with a reduced leading face, there is provided significant area for the placement of grafting material and/or bone regrowth.

It is generally desirable to form J-shaped implant with a construction that provides substantial structural stability during healing but still allows enough space for significant regrowth. In order to provide both structural stability and room for regrowth a hybrid or composite implant may be constructed.

Figure 56:
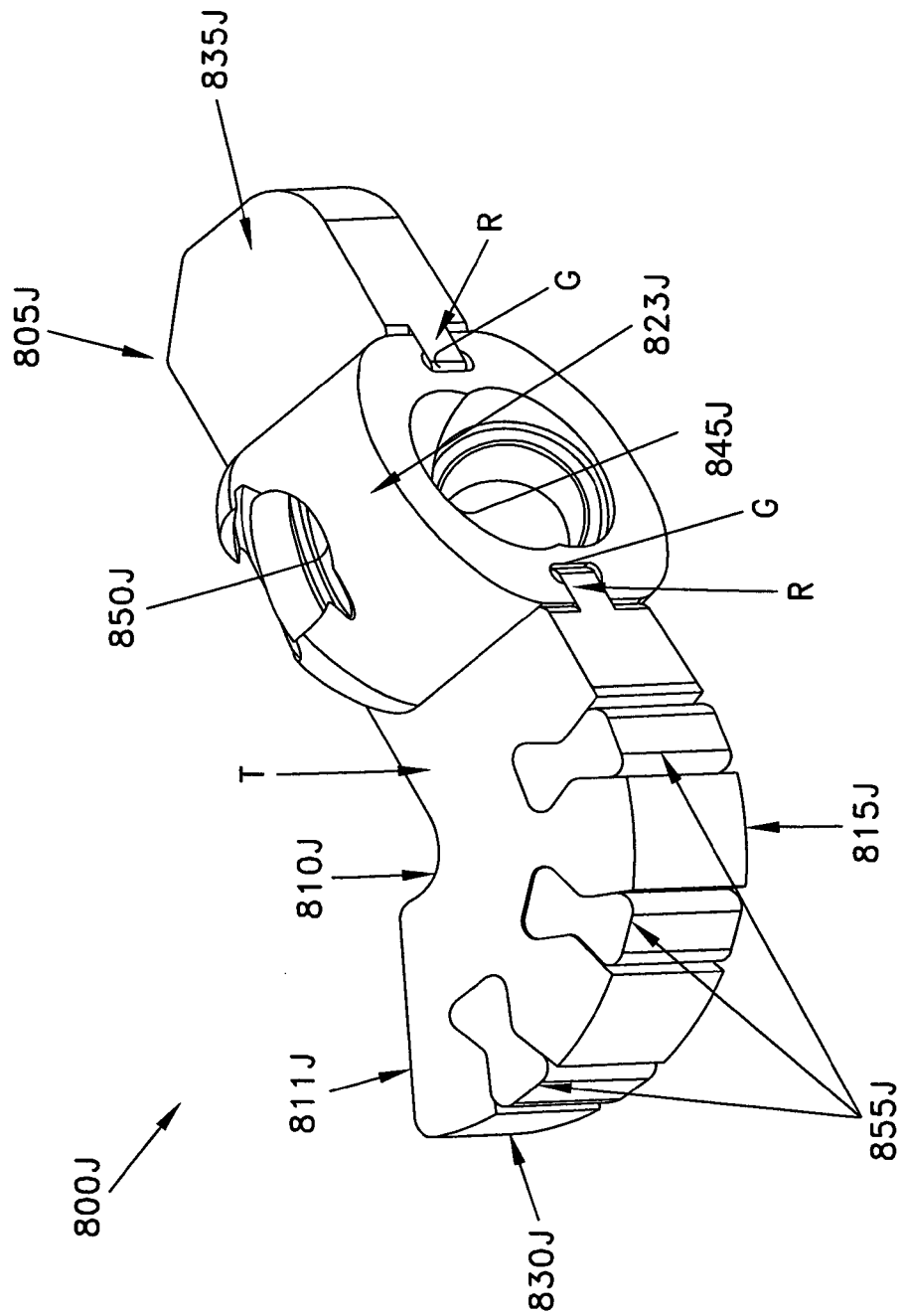

In accordance with the present invention, and looking next at FIG. 56, there is shown a composite implant 800J. Implant 800J is generally characterized by a body for disposition within the wedge-shaped opening of the osteotomy and supporting the tibia while healing occurs, and at least one key formed integral with the body for stabilizing the body relative to the tibia while healing occurs, wherein at least a portion of the body and the at least one key are formed out of a relatively strong, load-bearing material (e.g., PEEK) whereby to stabilize the tibia during healing, and further wherein at least a portion of the body is formed out of a bone growth-promoting material (e.g., allograft bone material) whereby to enhance bone healing.

In one preferred construction, and looking now at FIG. 56, novel implant 800J comprises a J-shaped body 805J and is formed out of multiple materials. Implant 800J comprises a curved leading face 810J, a flat leading face 811J, and a curved trailing face 815J. Implant 800J further comprises a top surface T and a bottom surface B.

J-shaped implant body 805J comprises a singular key 823J. By way of example but not limitation, key 823J may be formed of PEEK or another structural material, etc. This provides adequate shear strength and vertical support for the implant, while providing the structural integrity necessary to receive and fix fixation screws.

J-shaped implant body 805J further comprises a first, arcuate, lateral extension 830J extending adjacent to key 823J in a posterior direction, and a second lateral extension 835J extending adjacent to key 823J in an anterior direction. By way of example but not limitation, first, arcuate, lateral extension 830J and second lateral extension 835J may be formed of a resorbable or ceramic composite material, allograft bone material, etc. This provides adequate support for the compressive load during positioning of the implant, while also providing maximum bone re-growth in the healed construct.

Key 823J extends between leading face 810J and trailing face 815J and comprises a pair of diametrically-opposed grooves G for receiving rails R formed on first, arcuate lateral extension 830J and second lateral extension 835J, so as to connect key 823J to both first, arcuate lateral extension and second lateral extension.

Key 823J comprises a bores 845J, 850J for receiving a fixation screw 865J for fixing implant 800J to the tibia. Bores 845J, 850J may be longitudinally aligned with the longitudinal axis of keys 823J, in at least one dimension.

First, arcuate, lateral extension may also be formed with structural pillars 855J along the perimeter of trailing face 815J. Pillars 855J may be formed out of PEEK or other structural material, etc. so as to provide load-bearing strength to first, arcuate, lateral extension 830J and implant 800J.

For illustration purposes, pillars 855J are shown having a 'dog-bone' shape in FIG. 56, but it should be appreciated that pillars 855J may be formed with any geometrical cross-section. Pillars 855J may be formed as multiple distinct pillars or may be formed as a single load-bearing pillar.

Furthermore, it may be desirable to form implant 800J with more than one key. Where more than one key is provided in implant 800J, a bridge preferably formed of PEEK or other structural material would connect the two or more keys.

Key 823J may be connected to first, arcuate, lateral extension and/or second lateral extension using various joining means including dovetail rails, mortise-tenon joints, etc.

Anterio-Lateral Osteotomies

In the foregoing description, the present invention is discussed in the context of performing an open wedge osteotomy using an antero-medial approach so as to effect a medial opening wedge osteotomy. Of course, it should be appreciated that the present invention may also be used in antero-lateral approaches so as to effect a lateral opening wedge osteotomy, or in other approaches which will be well known to those skilled in the art.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A one piece osteotomy implant for disposition in a wedge-shaped osteotomy opening in a bone, the implant comprising:
    a body for disposition within the wedge-shaped osteotomy opening in the bone and adapted to support the bone while healing occurs, said body having a leading face, a trailing face, and a longitudinal axis extending transverse to said trailing face; and
    at least one key integral with said body for stabilizing said body relative to the adjacent bone while healing occurs, said at least one key extending longitudinally from said trailing face to said leading face and having an outwardly extending curved surface that is transverse to said longitudinal axis, and a bore extending therethrough.

2. An osteotomy implant according to claim 1 wherein said body is generally J-shaped.

3. An osteotomy implant according to claim 1 wherein said body comprises a top surface comprising a plurality of top surface segments separated by said at least one key, and further wherein the plurality of top surface segments are substantially coplanar with one another.

4. An osteotomy implant according to claim 3 wherein said body comprises a bottom surface comprising a plurality of bottom surface segments separated by said at least one key, and further wherein said plurality of bottom surface segments are substantially coplanar with one another.

5. An osteotomy implant according to claim 4 wherein said top and bottom surfaces converge toward one another in a substantially medial-to-lateral direction relative to a patient anatomy.

6. An osteotomy implant according to claim 1 wherein two keys are integral with said body, the two keys being connected to each other by a bridge.

7. An osteotomy implant according to claim 6 wherein said keys are provided with at least one bore extending therethrough.

8. An osteotomy implant according to claim 7 wherein the longitudinal axis of the at least one bores lies within the same plane as the longitudinal axis of the key.

9. An osteotomy implant according to claim 8 wherein said at least one key is provided with a plurality of bores extending therethrough, and further wherein the bores diverge from one another.

10. An osteotomy implant according to claim 1, further comprising at least one fenestration extending through said body.

11. An osteotomy implant according to claim 10 wherein said fenestration extends substantially transversely through said implant body.

12. An osteotomy implant according to claim 10 wherein the fenestration extends substantially radially through said implant body.

13. An osteotomy implant according to claim 10 wherein the fenestration extends substantially axially through said implant body.

14. A one piece osteotomy implant for disposition in a wedge-shaped osteotomy opening in a bone, the implant comprising:
    a body for disposition within the wedge-shaped osteotomy opening in the bone and adapted to support the bone while healing occurs, said body having a trailing face and an axis transverse to the trailing face; and
    at least one key integral with said body for stabilizing said body relative to the adjacent bone while healing occurs, said key having at least one bore extending therethrough and a protruding outer curved surface with a peak / valley that extends along said axis;
    wherein at least a portion of said body and said at least one key are formed of a relatively strong, load-bearing material, whereby to stabilize the bone during healing;
    and further wherein at least a portion of said body is formed of a bone growth-promoting material, whereby to enhance bone healing across the osteotomy opening in the bone.

15. An osteotomy implant according to claim 14 wherein said body is generally J-shaped.

16. An osteotomy implant according to claim 14 wherein said body comprises a top surface comprising a plurality of top surface segments separated by said at least one key, and further wherein said plurality of top surface segments are substantially coplanar with one another.

17. An osteotomy implant according to claim 16 wherein said body comprises a bottom surface comprising a plurality of bottom surface segments separated by said at least one key, and further wherein said plurality of bottom surface segments are substantially coplanar with one another.

18. An osteotomy implant according to claim 17 wherein said top and bottom surfaces converge toward one another in a substantially medial-to-lateral direction relative to a selected patient anatomy.

19. An osteotomy implant according to claim 14 wherein two keys are integral with said body, the two keys being connected to each other by a bridge.

20. An osteotomy implant according to claim 14 wherein each bore is longitudinally aligned with a longitudinal axis of said key.

21. An osteotomy implant according to claim 20 wherein each of said keys is provided with a plurality of bores extending therethrough, and further wherein the bores diverge from one another.

22. An osteotomy implant according to claim 14 wherein the load-bearing material comprises PEEK.

23. An osteotomy implant according to claim 14 wherein the bone growth-promoting material comprises allograft bone material.

* * * * *